US006806055B2

(12) United States Patent
Berman et al.

(10) Patent No.: US 6,806,055 B2
(45) Date of Patent: *Oct. 19, 2004

(54) HIV ENVELOPOLYPE PEPTIDES

(75) Inventors: Phillip W. Berman, Portola Valley, CA (US); Gerald R. Nakamura, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 207 days.

This patent is subject to a terminal disclaimer.

(21) Appl. No.: 09/966,931

(22) Filed: Sep. 27, 2001

(65) Prior Publication Data

US 2003/0064361 A1 Apr. 3, 2003

Related U.S. Application Data

(60) Division of application No. 09/492,739, filed on Jan. 27, 2000, now Pat. No. 6,331,404, which is a division of application No. 09/134,075, filed on Aug. 13, 1998, now Pat. No. 6,042,836, which is a division of application No. 08/448,603, filed as application No. PCT/US94/06036 on Jun. 7, 1994, now Pat. No. 5,864,027, which is a continuation-in-part of application No. 08/072,833, filed on Jun. 7, 1993, now abandoned.

(51) Int. Cl.[7] .................... G01N 33/53; A61K 39/21; A61K 39/00; C07K 17/00; C07H 21/04
(52) U.S. Cl. ............. 435/7.1; 424/188.1; 424/208.1; 424/184.1; 424/187.1; 530/350; 536/23.1
(58) Field of Search ............... 435/7.1; 424/188.1, 424/208.1, 184.1, 187.1; 530/350; 536/23.1

(56) References Cited

U.S. PATENT DOCUMENTS

| 4,725,669 A | 2/1988 | Essex et al. ............. 530/322 |
| 5,166,050 A | 11/1992 | Shriver et al. ............. 435/5 |
| 5,420,030 A | 5/1995 | Reitz, Jr. et al. ......... 435/235.1 |
| 5,576,000 A | 11/1996 | Reitz, Jr. et al. ......... 424/188.1 |
| 5,792,459 A | 8/1998 | Haigwood ............... 424/188.1 |

FOREIGN PATENT DOCUMENTS

| AU | A-33320/89 | 11/1989 |
| EP | 0 187 041 A1 | 7/1986 |
| EP | 0 327 180 A2 | 8/1989 |

(List continued on next page.)

OTHER PUBLICATIONS

Fox; No Winners against AIDS; BIO/Technology; vol. 12; p. 128, 1994.*
Haynes et al.; Update on the issues of HIV vaccine development; Ann. Med.; vol. 28, pp. 39–41, 1996.*
Baltimore et al.; HIV vaccines: prospects and challenges; Sci. Am.; pp. 98–103, 1998.*

(List continued on next page.)

Primary Examiner—Hankyel T. Park
(74) Attorney, Agent, or Firm—Emily M. Haliday; Quine Intellectual Property Law Group, P.C.

(57) ABSTRACT

A method for the rational design and preparation of vaccines based on HIV envelope polypeptides is described. In one embodiment, the method for making an HIV gp120 subunit vaccine for a geographic region comprises determining neutralizing epitopes in the V2 and/or C4 domains of gp120 of HIV isolates from the geographic region and selecting an HIV strain having gp120 a neutralizing epitope in the V2 or C4 domain which is common among isolates in the geographic region. In a preferred embodiment of the method, neutralizing epitopes for the V2, V3, and C4 domains of gp120 are determined. At least two HIV isolates having different neutralizing epitopes in the V2, V3, or C4 domain are selected and used.to make the vaccine. The invention also provides a multivalent HIV gp120 subunit vaccine. A DNA sequence encoding gp120 from preferred vaccine strains of HIV, $GNE_8$ and $GNE_{16}$, expression constructs comprising the $GNE_8$-gp120 and $GNE_{16}$-gp120 encoding DNA under the transcriptional and translational control of a heterologous promoter, and isolated $GNE_8$-gp120 and $GNE_{16}$-gp120 are also described.

45 Claims, 10 Drawing Sheets

FOREIGN PATENT DOCUMENTS

| | | |
|---|---|---|
| EP | 0 335 635 A1 | 10/1989 |
| EP | 0 339 504 A2 | 11/1989 |
| EP | 0 527 760 B1 | 2/1993 |
| EP | 0 394 386 B1 | 6/1995 |
| EP | 0 187 041 B1 | 5/1996 |
| EP | 0 279 688 B1 | 4/1997 |
| WO | WO 89/12095 | 12/1989 |
| WO | WO 90/02196 | 3/1990 |
| WO | WO 90/03984 | 4/1990 |
| WO | WO 91/04273 | 4/1991 |
| WO | WO 91/13906 | 9/1991 |
| WO | WO 91/15238 | 10/1991 |
| WO | WO 91/15512 | 10/1991 |
| WO | WO 92/06990 | 4/1992 |
| WO | WO 93/20104 | 10/1993 |
| WO | WO 94/28929 | 12/1994 |

OTHER PUBLICATIONS

Earl, Patricia et al., "Biological and Immunological Properties of Human Immunodeficiency Virus Type 1 Envelope Glycoprotein: Analysis of Proteins with Truncations and Deletions Expressed by Recombinant Vaccinia Viruses," *Journal of Virology* 65:1:31–41 (Jan. 1991).

Haigwood, Nancy L. et al., "Importance of Hypervariable Regions of HIV–1 gp120 in the Generation of Virus Neutralizing Antibodies," *Aids Reseach and Human Retroviruses* 6:7:855–869 (1990).

McElrath, et al., "Human immunodeficiency virus type 1 infection despite prior immunization with a recombinant envelope vaccine regimen," *Proc. Natl. Acad. Sci. USA* 93:3972–3977 (Apr. 1996).

Moore, "Enhanced: Coreceptors—Implications for HIV Pathogenesis and Therapy," *Science* 276:51 (Apr. 4, 1997).

Bhat, S., et al.: "The Galatosyl Ceramide/Sulfatide Receptor Binding Region of HIV–1 gp120 Maps to Amino Acids 206–275" *AIDS Research and Human Retroviruses*, 9:2:175–181, XP002139997 (Feb. 1993).

Linsley, P.S., et al., "Effects of Anti–gp120 Monoclonal Antibodies on CD4 Receptor Binding by the env Protein of Human Immunodeficiency Virus Type 1" *Journal of Virology*, 62:10:3695–3702, XP000579292 (Oct. 1988).

Berman, et al. "Genetic and Immunologic Characterization of Viruses Infecting MN–rgp120 Vaccinated Volunteers," One World, One Hope: XI International Conference on AIDS, 10:3:10 (Jul. 7–12, 1996).

Butini et al; Comparative analysis of HIV–specific CTL activity in lymphoid tissue and peripheral blood; J. Cellular Biochemistry; Sup. 18B J 306.

Cohen; Jitters jeopardize AIDS vaccine trial; Science; vol. 262 pp. 980–981.

Haynes et al.; Scientific and social issues of human immunodeficiency virus vaccine development; Scinec; vol. 260; pp. 1279–1286.

Kahn et al. Clinical, immunologic, and virologic observations related to human immunodeficiency virus (HIV) type 1 infection in a volunteer in an HIV–1 vaccine clinical trial. Journal of Infectious Diseases (May 1995) vol. 171. pp. 1343–1350.

McCutchan et al; Genetic variants of HIV–1 Thailand; AIDS Research and Human Retroviruses; vol. 8, No. 11; pp. 1887–1896.

Allan et al., "Major Glycoprotein Antigens that Induce Antibodies in AIDS Patients are Encoded by HTLV–III," *Science* 228, pp. 1091–1094 (May 31, 1985).

Anderson et al., "Effect of Dose and Immunization Schedule on Immune Response of Baboons to Recombinant Glycoprotein 120 of HIV–1," *The Journal of Infectious Diseases* 160(6), pp. 960–969 (Dec. 1989).

Arthur et al., "Challenge of Chimpanzees (*Pan troglodytes*) Immunized with Human Immunodeficiency Virus Envelope Glycoprotein gp120," *Journal of Virology* 63(12), pp. 5046–5053 (Dec. 1989).

Arthur, Larry O., "Serological Responses in Chimpanzees Inoculated With Human Immunodeficiency Virus Glycoprotein (gp120) Subunit Vaccine," *Proc. Natl. Acad. Sci. USA* 84, pp. 8583–8587 (Dec. 1987).

Barin et al., "Virus Envelope Protein of HTLV–III Represents Major Target Antigen For Antibodies in AIDS Patients," *Science* 228, pp. 1094–1096 (May 31, 1985).

Barrett et al., "Large–Scale Production and Purification of a Vaccinia Recombinant–Derived HIV–1 gp160 and Analysis of Its Immunogenicity," *AIDS Research And Human Retroviruses* 5(2), pp. 159–171 (1989).

Berkower et al., "A Predominant Group–Specific Neutralizing Epitope of Human Immunodeficiency Virus Type 1 Maps to Residues 342 to 511 of the Envelope Glycoprotein gp120," *Journal of Virology* 65(13), pp. 5983–5990 (Nov. 1991).

Berman et al., "Genetic and Immunologic Characterization of Viruses Infecting MN–rgp120–Vaccinated Volunteers," *The Journal of Infectious Diseases* 176, pp. 384–397 (Aug. 1997).

Berman et al., "Protection from Genital Herpes Simplex Virus Type 2 Infection by Vaccination with Cloned Type 1 Glycoprotein D," *Science* 227, pp. 1490–1492 (Mar. 1985).

Berman et al., "Human Immunodeficiency Virus Type 1 Challenge of Chimpanzees Immunized with Recombinant Envelope Glycoprotein gp120," *Proc. Natl. Acad. Sci. USA* 85, pp. 5200–5204 (Jul. 1988).

Berman et al., "Expression and Immunogenicity of the Extracellular Domain of the Human Immunodeficiency Virus Type–1 Envelope Glycoprotein gp160," *Journal of Virology* 63(8), pp. 3489–3498 (Aug. 1989).

Berman, P., et al., "Protection of Chimpanzees From Infection by HIV–1 After Vaccination with Recombinant Glycoprotein gp120 But Not gp160," *Nature* 345(6276), pp. 622–625 (Jun. 14, 1990).

Berman, P., et al., "Neutralization of Multiple Laboratory and Clinical Isolates of Human Immunodeficiency Virus Type 1 (HIV–1) by Antisera Raised Against gp120 from the MN Isolate of HIV–1," *Journal of Virology* 66(7), pp. 4464–4469 (Jul. 1992).

Broliden, P., et al., "Identification of Human Neutralization–inducing Regions of the Human Immunodeficiency Virus Type 1 Envelope Glycoproteins," *Proc. Natl. Acad. Sci. USA* 89, pp. 461–465 (Jan. 1992).

Bruck, Claudine, et al., "HIV–1 Envelope–elicited Neutralizing Antibody Titres Correlate With Protection and Virus Load In Chimpanzees,"*Vaccine* 12(12), pp. 1141–1148 (1994).

Chakrabarti et al., "Expression of the HTLV–III Envelope Gene by a Recombinant Vaccinia Virus," *Nature* 320, pp. 535–540 (Apr. 10, 1986).

Clements et al., "The V3 Loops of the HIV–1 and HIV–2 Surface Glycoproteins Contain Proteolytic Cleavage Sites: A Possible Function in Viral Fusion?" *AIDS Research and Human Retroviruses* 7(1), pp. 3–16 (1991).

Clements, *Certificate of Analysis*, Celltech Limited, 2 pages (Jan. 23, 1990).

Desrosiers et al., "Vaccine Protection Against Simian Immunodeficiency Virus Infection," *Proc. Natl. Acad. Sci. USA* 86, pp. 6353–6357 (Aug. 1989).

Eichberg, J.W., "Experience With Seventeen HIV Vaccine Efficacy Trials in Chimpanzees," Southwest Foundation for Biomedical Research, San Antonio, TX 7(2), p. 88 (Jun. 1991).

Fahey, J. L., and Schooley, R., "Status of Immune–based Therapies in HIV Infection and AIDS," *Clin. exp. Immunol* 88, pp. 1–5 (1992).

Fast, Patricia, "Phase I and II Trials of Candidate HIV–1 Vaccines: Current Status and Future Directions," *Neuvieme Colloque Des Cent Gardes* pp. 293–299 (1994).

NIH Conference, "Development and Evaluation of a Vaccine for Human Immunodeficiency Virus (HIV) Infection," *Annals of Internal Medicine* 110(5), pp. 373–385 (Anthony S. Fauci, moderator, Mar. 1, 1989).

Fung et al., "Identification and Characterization of a Neutralization Site within the Second Variable Region of Human Immunodeficiency Virus Type 1 gp120," *Journal of Virology* 66(2), pp. 848–856 (Feb. 1992).

Girard et al., "Immunization of Chimpanzees Confers Protection Against Challenge With Human Immunodeficiency Virus," *Proc. Natl. Acad. Sci. USA* 88, pp. 542–546 (Jan. 1991).

Gurgo, et al., "Short Communications: Envelope Sequences of Two New United States HIV–1 Isolates," *Virology* 164, pp. 531–536 (1988).

Haigwood, Nancy L., et al., "Native But Not Denatured Recombinant Human Immunodeficiency Virus Type 1 and gp120 Generates Broad–Spectrum Neutralizing Antibodies in Baboons," *Journal of Virology* 66, pp. 172–182 (Jan. 1992).

Ho et al., "Another discontinous epitope on glycoprotein gp120 that is important in human immunodeficiency virus type 1 neutralization is identified by a monoclonal antibody," *Proc. Natl. Acad. Sci. USA* 88, pp. 8949–8952 (Oct. 1991).

Homsy et al., "The Fc and Not CD4 Receptor Mediates Antibody Enhancement of HIV Infection in Human Cells," *Science* 244, pp. 1357–1360 (Jun. 16, 1989).

Hu, S.L., et al., "Expression of AIDS Virus Envelope Gene in Recombinant Vaccinia Viruses," *Nature* 320, pp. 537–540 (Apr. 10, 1986).

Hu et al., "Effect of Immunization with a Vaccinia–HIV env Recombinant of HIV Infection of Chimpanzees," *Nature* 328, pp. 721–723 (Aug. 20, 1987).

Ichimura, H., et al., "Biological, Serological, and Genetic Characterization of HIV–1 Subtype E Isolates from Northern Thailand," *AIDS Research and Human Retroviruses* 10(3), pp. 263–269 (1994).

Javaherian, K., et al., "Principal Neutralizing Domain of the Human Immunodeficiency Virus Type 1 Envelope Protein", *Proc. Natl. Acad. Sci. USA* 86, pp. 6768–6772 (Sep. 1989).

Kitchen et al., "Aetiology of AIDS—Antibodies to Human T–cell Leukaemia Virus (Type III) in Haemophiliacs," *Nature* 312, pp. 367–369 (Nov. 22, 1984).

Klein, M., et al., "Immunogenicity of Synthetic HIV–1 T–B Tandem Epitopes," *Septieme Colloque Des Cent Gardes*, pp. 169–174 (1992).

Krust et al., "Characterization of a Monoclonal Antibody Specific for the HIV–1 Precursor Glycoprotein," *AIDS* 2(1), pp. 17–24 (1988).

LaRosa, G., et al., "Conserved Sequence and Structural Elements in the HIV–1 Principal Neutralizing Determinant," *Science* 249, pp. 932–935 (Aug. 24, 1990).

Lasky et al., "Neutralization of the AIDS Retrovirus by Antibodies to a Recombinant Envelope Glycoprotein," *Science* 233, pp. 209–212 (Jul. 11, 1986).

Lasky et al., "Delineation of a Region of the Human Immunodeficiency Virus Type 1 gp120 Glycoprotein Critical for Interaction with CD4 Receptor," *Cell* 50, pp. 975–985 (Sep. 11, 1987).

Lasky, "Current Status of the Development of an AIDS Vaccine," *Critical Reviews in Immunology* 9(3), pp. 153–172 (1989).

Letvin et al., "AIDS–like Disease in Macaque Monkeys Induced by Simian Immunodeficiency Virus: A Vaccine Trial," *Vaccines*, pp. 209–213 (1987).

Looney et al., "Type–restricted Neutralization of Molecular Clones of Human Immunodeficiency Virus," *Science* 241, pp. 357–359 (Jul. 15, 1988).

Matsushita et al., "Characterization of a Human Immunodeficiency Virus Neutralizing Monoclonal Antibody and Mapping of the Neutralizing Epitope," *Journal of Virology* 62(6), pp. 2107–2114 (Jun. 1988).

Modrow, S., et al., "Computer–assisted Analysis of Envelope Protein Sequences of Seven Human Immunodeficiency Virus Isolates: Prediction of Antigenic Epitopes in Conserved and Variable Regions," *Journal of Virology* 61(2), pp. 570–578 (Feb. 1987).

Moore et al., "Immunochemical Analysis of the gp120 Surface Glycoprotein of Human Immunodeficiency Virus Type 1: Probing the Structure of the C4 and V4 Domains and the Interaction of the C4 Domain with the V3 Loop," *Journal of Virology* 67(8), pp. 4785–4796 (Aug. 1993).

Moore et al., "Probing the Structure of the Human Immunodeficiency Virus Surface Glycoprotein gp120 with a Panel of Monoclonal Antibodies," *Journal of Virology* 68(1), pp. 469–484 (Jan. 1994).

Moore et al., "Probing the Structure of the V2 Domain of Human Immunodeficiency Virus Type 1 Surface Glycoprotein gp120 with a Panel of Eight Monoclonal Antibodies: Human Immune Response to the V1 and V2 Domains," *Journal of Virology* 67(10), pp. 6136–6151 (Oct. 1993).

Murphey–Corb et al., "A Formalin–inactivated Whole SIV Vaccine Confers Protection in Macaques," *Science* 246, pp. 1293–1297 (Dec. 8, 1989).

Nakamura, Gerald, R., et al., "Monoclonal Antibodies to the Extracellular Domain of HIV–1$_{IIIB}$ gp160 that Neutralize Infectivity, Block Binding to CD4, and React with Diverse Isolates," *AIDS Research and Human Retroviruses* 8(11), pp. 1875–1885 (1992).

Nakamura, G., et al., "Strain Specificity and Binding Affinity Requirements of Neutralizing Monoclonal Antibodies to the C4 Domain of gp120 from Human Immunodeficiency Virus Type I," *Journal of Virology* 67(10), pp. 6179–6191 (Oct. 1993).

Newmark, "Receding Hopes of AIDS Vaccines," *Nature* 333, p. 699 (Jun. 23, 1988).

Palker et al., "Type–specific Neutralization of the Human Immunodeficiency Virus with Antibodies to env–encoded Synthesis Peptides," *Proc. Natl. Acad. Sci. USA* 85, pp. 1932–1936 (Mar. 1988).

Potts, K., et al., "Genetic Heterogeneity of the V3 Region of the HIV–1 Envelope Glycoprotein in Brazil," *AIDS* 7(9), pp. 1191–1197 (1993).

Prince et al., "Failure of a Human Immunodeficiency Virus (HIV) Immune Globulin to Protect Chimpanzess Against Experimental Challenge with HIV," *Proc. Natl. Acad. Sci. USA* 85, pp. 6944–6948 (Sep. 1988).

Putney, Scott D., et al., "HIV Vaccine Development: Lessons Learned to Date," *Biotechnology Therepeutics* 2(1–2), pp. 1–7 (1991).

Putney, Scott D., et al., "Features of the HIV Envelope and Development of a Subunit Vaccine," *AIDS Vaccine Research and Clinical Trials*, Marcel Dekker, Inc., New York, pp. 3–61 (1990).

Robey et al., "Characterization of Envelope and Core Structural Gene Products of HTLV–III with Sera from AIDS Patients," *Science* 228, pp. 593–595 (May 3, 1985).

Robey et al., "Prospect for Prevention of Human Immunodeficiency Virus Infection: Purified 120–kDa Envelope Glycoprotein Induces Neutralizing Antibody," *Proc. Natl. Acad. Sci. USA* 83, pp. 7023–7027 (Sep. 1986).

Robinson et al., "Antibody–Dependent Enhancement of Human Immunodeficiency Virus Type 1 Infection," *The Lancet*, pp. 790–794 (Apr. 9, 1988).

Robinson et al., "Human Monoclonal Antibodies to the Human Immunodeficiency Virus Type 1 (HIV–1) Transmembrane Glycoprotein gp41 Enhance HIV–1 Infection in vitro," *Proc. Natl. Acad. Sci. USA* 87, pp. 3185–3189 (Apr. 1990).

Rusche et al., "Antibodies that Inhibit Fusion of Human Immunodeficiency Virus–infected Cells Bind a 24–amino Acid Sequence of the Viral Envelope, gp120," *Proc. Natl. Acad. Sci. USA* 85, pp. 3198–3202 (May 1988).

Salk, "Prospects for the Control of AIDS by Immunizing Seropositive Individuals," *Nature* 327, pp. 473–476 (Jun. 11, 1987).

Salk and Salk, "Control of Influenz and Poliomyelitis With Killed Virus Vaccines," *Science* 195, pp. 834–847 (Mar. 4, 1977).

Scandella, Carol, J., et al., "Nonaffinity Purification of Recombinant gp120 for Use in AIDS Vaccine Development," *AIDS Research and Human Retroviruses* 9(12), pp. 1233–1244 (1993).

Shafferman, A., et al., "Patterns of Antibody Recognition of Selected Conserved Amino Acid Sequences from the HIV Envelope in Sera from Different Stages of HIV Infection," *AIDS Research and Human Retroviruses* 5(1), pp. 33–39 (1989).

Stephens et al., "A Chink in HIV's Armour?" *Nature* 343, p. 219 (Jan. 18, 1990).

Sullivan et al., "Effect of Amino Acid Changes in the V1/V2 Region of the Human Immunodeficiency Virus Type 1 gp120 Glycoprotein on Subunit Association, Syncytium Formation, and Recognition by a Neutralizing Antibody," *Journal of Virology* 67(6), pp. 3674–3679 (Jun. 1993).

Thali, M., et al., "Discontinuous, Conserved Neutralization Epitopes Overlapping the CD4–Binding Region of Human Immunodeficiency Virus Type 1 gp120 Envelope Glycoprotein," *Journal of Virology* 66(9), pp. 5635–5641 (Sep. 1992).

van Eedenburg et al., "Cell–mediated Immune Proliferative to HIV–1 of Chimpanzees Vaccinated with Different Vaccinia Recombinant Viruses," *AIDS Research and Human Retoviruses* 5(1), pp. 41–50 (1989).

Vandenbark et al., "Immunization with a Synthetic T–Cell Receptor V–region Peptide Protects Against Experimental Autoimmune Encephalomyelitis," *Nature* 341, pp. 541–544 (Oct. 12, 1989).

Veronese et al., "Characterization of gp41 as the Transmembrane Protein Coded by the HTLV–III/LAV Envelope Gene," *Science* 229, pp. 1402–1405 (Sep. 27, 1985).

Wyatt et., "Relationship of the Human Immunodeficiency Virus Type 1 gp 120 Third Variable Loop to a Component of the CD4 Binding Site in the Fourth Conserved Region," *Journal of Virology* 66(12), pp. 6997–7004 (Dec. 1992).

Yoshiyama et al., "Characterization of Mutants of Human Immunodeficiency Virus Type 1 That Have Escaped Neutralization by a Monoclonal Antibody to the gp120 V2 Loop," *Journal of Virology* 68(2), pp. 974–978 (Feb. 1994).

Zagury et al., "Immunization Against AIDS in Humans," *Nature* 326, pp. 249–250 (Mar. 19, 1987).

Zagury et al., "A Group Specific Anamnestic Immune Reaction Against HIV–i Induced by a Candidate Vaccine Against AIDS," *Nature* 332, pp. 728–731 (Apr. 21, 1988).

Zarling et al., "T–cell Responses to Human AIDS Virus in Macaques Immunized with Recombinant Vaccinia Viruses," *Nature* 323, pp. 344–346 (Sep. 25, 1986).

* cited by examiner

```
418                    445
CKIKQIINMWQKGKAMYAPPIEGQIRC   MN_GNE               (SEQ.ID.NO.3)
---------E----------------    MN_1984              (SEQ.ID.NO.4)
-R-------E-------K--------    JRCSF                (SEQ.ID.NO.5)
-R-------E-----------N----    Z6                   (SEQ.ID.NO.6)
-R----R--E-----I----------    NY5                  (SEQ.ID.NO.7)
-R-------E----------S-----    Z321                 (SEQ.ID.NO.8)
-R----V--E----K-V-K-------    A244                 (SEQ.ID.NO.9)
---------GA-Q-------S-T-N-    LAI_IIIB, LAI_BRU, LAI_HXB3  (SEQ.ID.NO.10)
-R----F--E----------S-----    LAI_HXB2             (SEQ.ID.NO.11)
------I--------K----S-----    LAI_BH10, LAI_HXB3   (SEQ.ID.NO.12)
-R----I--E----------S-----    MN_1984              (SEQ.ID.NO.13)
---------E----------------
```

FIG. 4

```
418                    445
CKIKQIINMWQKVGKAMYAPPIEGQIRC    MN_GNE              (SEQ.ID.NO.3)
-----------E---------------    MN.429E             (SEQ.ID.NO.15)
-----------A---------------    MN.429A             (SEQ.ID.NO.16)
-A-------------------------    MN.419A             (SEQ.ID.NO.17)
---A-----------------------    MN.421A             (SEQ.ID.NO.18)
--------------A------------    MN.432A             (SEQ.ID.NO.19)
----------------------A----    MN.440A             (SEQ.ID.NO.20)
-R-----F-----S-------------    LAI_IIIB            (SEQ.ID.NO.21)
-------F-------------------    MN.423F             (SEQ.ID.NO.22)
-------F---E---------------    MN.423F,429E        (SEQ.ID.NO.23)
```

FIG. 5

HIV ENVELOPOLYPE PEPTIDES

CROSS-REFERENCE TO RELATED APPLICATIONS

This application is a divisional of application Ser. No. 09/492,739, filed Jan. 27, 2000 now U.S. Pat. No. 6,331,404, which is a divisional of application Ser. No. 09/134,075, filed Aug. 13, 1998, now U.S. Pat. No. 6,042,836, which is a divisional of application Ser. No. 08/448,603, filed Oct. 10, 1995, now U.S. Pat. No. 5,864,027 which is a 35 U.S.C. 371 of PCT/US94/06036, filed Jun. 7, 1994, which is a continuation-in-part of application Ser. No. 08/072,833, filed Jun. 7, 1993 now abandoned, all of which are hereby incorporated by reference in their entirety.

FIELD OF THE INVENTION

This invention relates to the rational design and preparation of HIV vaccines based on HIV envelope polypeptides and the resultant vaccines. This invention further relates to improved methods for HIV serotyping and immunogens which induce antibodies useful in the serotyping methods.

BACKGROUND OF THE INVENTION

Acquired immunodeficiency syndrome (AIDS) is caused by a retrovirus identified as the human immunodeficiency virus (HIV). There have been intense effort to develop a vaccine. These efforts have focused on inducing antibodies to the HIV envelope protein. Recent efforts have used subunit vaccines where an HIV protein, rather than attenuated or killed virus, is used as the immunogen in the vaccine for safety reasons. Subunit vaccines generally include gp120, the portion of the HIV envelope protein which is on the surface of the virus.

The HIV envelope protein has been extensively described, and the amino acid and RNA sequences encoding HIV envelope from a number of HIV strains are known (Myers, G. et al., 1992. Human Retroviruses and AIDS. A compilation and analysis of nucleic acid and amino acid sequences. Los Alamos National Laboratory, Los Alamos, N. Mex.). The HIV envelope protein is a glycoprotein of about 160 kd (gp160) which is anchored in the membrane bilayer at its carboxyl terminal region. The N-terminal segment, gp120, protrudes into the aqueous environment surrounding the virion and the C-terminal segment, gp41, spans the membrane. Via a host-cell mediated process, ap160 is cleaved to form gp120 and the integral membrane protein gp41. As there is no covalent attachment between gp120 and gp41, free gp120 is released from the surface of virions and infected cells.

The gp120 molecule consists of a polypeptide core of 60,000 daltons which is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence, and the positions of 13 of the approximately 24 N-linked glycosylation sites in the gp120 sequence are common to all gp120 sequences. The hypervariable domains contain extensive amino acid substitutions, insertions and deletions. Sequence variations in these domains result in up to 30% overall sequence variability between gp120 molecules from the various viral isolates. Despite this variation, all gp120 sequences preserve the virus's ability to bind to the viral receptor CD4 and to interact with gp41 to induce fusion of the viral and host cell membranes.

gp120 has been the object of intensive investigation as a vaccine candidate for subunit vaccines, as the viral protein which is most likely to be accessible to immune attack. gp120 is considered to be a good candidate for a subunit vaccine, because (i) gp120 is known to possess the CD4 binding domain by which HIV attaches to its target cells, (ii) HIV infectivity can be neutralized in vitro by antibodies to gp120, (iii) the majority of the in vitro neutralizing activity present in the serum of HIV infected individuals can be removed with a gp120 affinity column, and (iv) the gp120/gp41 complex appears to be essential for the transmission of HIV by cell-to-cell fusion.

The identification of epitopes recognized by virus neutralizing antibodies is critical for the rational design of vaccines effective against HIV-1 infection. One way in which antibodies would be expected to neutralize HIV-1 infection is by blocking the binding of the HIV-1 envelope glycoprotein, gp120, to its cellular receptor, CD4. However, it has been surprising that the CD4 blocking activity, readily demonstrated in sera from HIV-1 infected individuals (31, 44) and animals immunized with recombinant envelope glycoproteins (1–3), has not always correlated with neutralizing activity (2, 31, 44). Results obtained with monoclonal antibodies have shown that while some of the monoclonal antibodies that block the binding of gp120 to CD4 possess neutralizing activity, others do not (4, 7, 16, 26, 33, 35, 43, 45). When the neutralizing activity of CD4 blocking monoclonal antibodies are compared to those directed to the principal neutralizing determinant (PND) located in the third variable domain (V3 domain) of gp120 (10, 39), the CD4 blocking antibodies appear to be significantly less potent. Thus, CD4 blocking monoclonal antibodies typically exhibit 50% inhibitory concentration values ($IC_{50}$) in the 1–10 µg/ml range (4, 16, 26, 33, 35, 43, 45) whereas PND directed monoclonal antibodies typically exhibit $IC_{50}$ values in the 0.1 to 1.0 µg/ml range (23, 33, 42).

Subunit vaccines, based on gp120 or another viral protein, that can effectively induce antibodies that neutralize HIV are still being sought. However, to date no vaccine has not been effective in conferring protection against HIV infection.

DESCRIPTION OF THE BACKGROUND ART

Recombinant subunit vaccines are described in Berman et al., PCT/US91/02250 (published as number WO91/15238 on Oct. 17, 1991). See also, e.g. Hu et al., *Nature* 328:721–724 (1987) (vaccinia virus-HIV envelope recombinant vaccine); Arthur et al., *J. Virol.* 63(12): 5046–5053 (1989) (purified gp120); and Berman et al., *Proc. Natl. Acad. Sci. USA* 85:5200–5204 (1988) (recombinant envelope glycoprotein gp120).

Numerous sequences for gp120 are known. The sequence of gp120 from the IIIB substrain of HIV-1$_{LAI}$ referred to herein is that determined by Muesing et al., "Nucleic acid structure and expression of the human AIDS/lymphadenopathy retrovirus, *Nature* 313:450–458 (1985). The sequences of gp120 from the NY-5, Jrcsf, Z6, Z321, and HXB2 strains of HIV-1 are listed by Myers et al., "Human Retroviruses and AIDS; A compilation and analysis of nucleic acid and amino acid sequences," Los Alamos National Laboratory, Los Alamos, N. Mex. (1992). The sequence of the Thai isolate A244 is provided by McCutchan et al., "Genetic Variants of HIV-1 in Thailand," *AIDS Res. and Human Retroviruses* 8:1887–1895 (1992). The $MN_{1984}$ clone is described by Gurgo et al., "Envelope sequences of two new United States HIV-1 isolates," *Virol.* 164: 531–536 (1988). The amino acid sequence of this MN clone differs by approximately 2% from the MN-gp120 clone ($MN_{GNE}$) disclosed herein and obtained by Berman et al.

Each of the above-described references is incorporated herein by reference in its entirety.

SUMMARY OF THE INVENTION

The present invention provides a method for the rational design and preparation of vaccines based on HIV envelope polypeptides. This invention is based on the discovery that there are neutralizing epitopes in the V2 and C4 domains of gp120, in addition to the neutralizing epitopes in the V3 domain. In addition, the amount of variation of the neutralizing epitopes is highly constrained, facilitating the design of an HIV subunit vaccine that can induce antibodies that neutralize a plurality of HIV strains for a given geographic region.

In one embodiment, the present invention provides a method for making an HIV gp120 subunit vaccine for a geographic region in which a neutralizing epitope in the V2 and/or C4 domains of gp120 of HIV isolates from the geographic region is determined and an HIV strain having gp120 which has a neutralizing epitope in the V2 or C4 domain which is common among isolates in the geographic region is selected and used to make the vaccine.

In a preferred embodiment of the method, neutralizing epitopes for the V2, V3, and C4 domains of gp120 from HIV isolates from the geographic region are determined. At least two HIV isolates having different neutralizing epitopes in the V2, V3, or C4 domain are selected and used to make the HIV gp120 subunit vaccine. Preferably, each of the selected isolates have one of the most common neutralizing epitopes for the V2, V3, or C4 domains.

The invention also providesa multivalent HIV gp120 subunit vaccine. The vaccine comprises gp120 from two isolates of HIV having at least one different neutralizing epitope. Preferably, the isolates have the most common neutralizing epitopes in the geographic region for one of the domains.

A DNA sequence of less than 5 kilobases encoding gp120 from preferred vaccine strains of HIV, $GNE_8$ and $GNE_{16}$, expression construct comprising the $GNE_8$-gp120 and $GNE_{16}$-gp120 encoding DNA under the transcriptional and translational control of a heterologous promoter, and isolated $GNE_8$-gp120 and $GNE_{16}$-gp120 are also provided. The invention further provides improved methods for HIV serotyping in which epitopes in the V2 or C4 domains of gp120 are determined and provides immunogens (truncatec gp120 sequences) which induce antibodies useful in the serotyping methods.

BRIEF DESCRIPTION OF THE DRAWINGS

FIG. 4 shows a C4 domain sequence comparison (SEQ. ID. Nos. 3–13). The C4 domain amino acid sequences of recombinant and virus derived gp120s used for monoclonal antibody binding studies were aligned starting the amino terminal cysteine. Amino acid positions are designated with respect to the sequence of MN-rgp120. Sequences of the LAI substrains, IIIB, BH10, Bru, HXB2, and HXB3 are shown for purposes of comparison.

FIG. 5 shows sequences of C4domain mutants of MN-rgp120 (SEQ. ID. Nos. 3 and 15–23). Nucleotide substitutions, resulting in the amino acid sequences indicated, were introduced into the C4 domain of MN-rgp120 gene using recombinant PCR. The resulting variants were assembled into the expression plasmid, pRK5, which was then transfected into 293 s cells. The binding of monoclonal antibodies to the resulting C4 domain variants was then analyzed (Table 5) by ELISA.

DETAILED DESCRIPTION OF THE INVENTION

Figure 1:
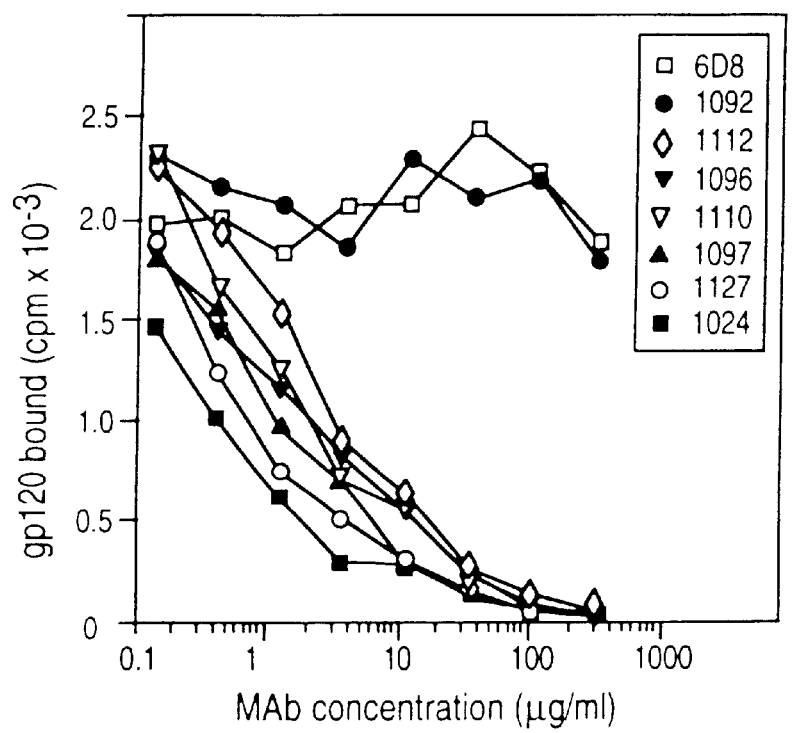
FIG. 1 describes inhibition of CD4 binding by monoclonal antibodies to recombinantly produced gp120 from the MN strain of HIV (MN-rgp120). Mice were immunized with MN-rgp120 and the resulting splenocytes were fused with the NP3×63.Ag8.653 cell line as described in Example 1. Thirty-five stable hybridoma clones, reactive with MN-rgp120 were identified by ELISA. Secondary screening revealed seven cell lines (1024, 1093, 1096, 1097, 1110, 1112, and 1027) secreting antibodies able to inhibit the binding of MN-rgp120 to biotin labeled recombinantly produced CD4 (rsCD4) in a ELISA using HRPO-strepavadin. Data obtained with monoclonal antibodies from the same fusion (1026, 1092, 1126) that failed to inhibit MN-rgp120 binding to CD4 is shown for purposes of comparison.

The present invention provides a method for the rational design and preparation of vaccines based on HIV envelope polypeptides. This invention is based on the discovery that there are neutralizing epitopes in the V2 and C4 domains of gp120, in addition to the neutralizing epitopes in the V3 domain. Although the amino acid sequences of the neutralizing epitopes in the V2, V3, and C4 domains are variable, it has now been found that the amount of variation is highly constrained. The limited amount of variation facilitates the design of an HIV subunit vaccine that can induce antibodies that neutralize the most common HIV strains for a given geographic region. In particular, the amino acid sequence of neutralizing epitopes in the V2, V3, and C4 domains for isolates of a selected geographic region is determined. gp120 from isolates having the most common neutralizing epitope sequences are utilized in the vaccine.

The invention also provides a multivalent gp120 subunit vaccine wherein gp120 present in the vaccine is from at least two HIV isolates which have different amino acid sequences for a neutralizing epitope in the V2, V3, or C4 domain of gp120. The invention further provides improved methods for HIV serotyping in which epitopes in the V2 or C4 domains of gp120 are determined and provides immunogens which induce antibodies useful in the serotyping methods.

The term "subunit vaccine" is used herein, as in the art, to refer to a viral vaccine that does not contain virus, but rather contains one or more viral proteins or fragments of viral proteins. As used herein, the term "multivalent" means that the vaccine contains gp120 from at least two HIV isolates having different amino acid sequences for a neutralizing epitope.

Vaccine Design Method

The vaccine design method of this invention is based on the discovery that there are neutralizing epitopes in the V2 and C4 domains of gp120, in addition to those found in the principal neutralizing domain (PND) in the V3 domain. Selecting an HIV isolate with appropriate neutralizing epitopes in the V2 and/or C4 domains provides a vaccine that is designed to induce immunity to the HIV isolates present in a selected geographic region. In addition, although the amino acid sequence of the V2, V3, and C4 domains containing the neutralizing epitopes is variable, the amount of variation is highly constrained, facilitating the design of a multivalent vaccine which can neutralize a plurality of the most common HIV strains for a given geographic region.

The method for making an HIV gp120 subunit vaccine depends on the use of appropriate strains of HIV for a selected geographic region. Appropriate strains of HIV for the region are selected by determining the neutralizing epitopes for HIV isolates and the percentage of HIV infections attributable to each strain present in the region. HIV strains which have the most common neutralizing epitopes in the V2 or C4 domains in the geographic region are selected. Preferably, isolates that confer protection against the most common neutralizing epitopes in the V2, V3, and C4 domains for a geographic region are selected.

One embodiment of the method for making an HIV gp120 subunit vaccine from appropriate strains of HIV for a geographic region comprises the following steps. A neutralizing epitope in the V2 or C4 domain of gp120 of HIV isolates from the geographic region is determined. An HIV strain having gp120 with a neutralizing epitope in the V2 or C4 domain that is common among HIV isolates in the geographic region is selected. gp120 from the selected isolate is used to make an HIV gp120 subunit vaccine.

In another embodiment of the method, the neutralizing epitopes in the V2, V3, and C4 domains of gp120 from HIV isolates from the geographic region are determined. At least two HIV isolates having different neutralizing epitopes in the V2, V3, or C4 domain are selected and used to make an HIV gp120 subunit vaccine. Preferably, the vaccine contains gp120 from at least the two or three HIV strains having the most common neutralizing epitopes for the V2, V3, or C4 domains. More preferably, the vaccine contains gp120 from sufficient strains so that at least about 50%, preferably about 70%, more preferably about 80% or more of the neutralizing epitopes for the V2, V3, and C4 domains in the geographic region are included in the vaccine. The location of the neutralizing epitopes in the V3 region are well known. The location of the neutralizing epitopes in the V2 and C4 regions are described hereinafter.

Each of the steps of the method are described in detail below.

Determining Neutralizing Epitopes

The first step in designing a vaccine for a selected geographic region is to determine the neutralizing epitopes in the gp120 V2 and/or C4 domains. In a preferred embodiment, neutralizing epitopes in the V3 domain (the principal neutralizing domain) are also determined. The location of neutralizing epitopes in the V3 domain is well known. Neutralizing epitopes in the V2 and C4 domains have now been found to be located between about residues 163 and 200 and between about residues 420 and 440, respectively. In addition, the critical residues for antibody binding are residues 171, 173, 174, 177, 181, 183, 187, and 188 in the V2 domain and residues 429 and 432 in the C4 domain, as described in detail in the Examples.

The neutralizing epitopes for any isolate can be determined by sequencing the region of gp120 containing the neutralizing epitope. Alternatively, when antibodies specific for the neutralizing epitope, preferably monoclonal antibodies, are available the neutralizing epitope can be determined by serological methods as described hereinafter. A method for identification of additional neutralizing epitopes in gp120 is described hereinafter.

Figure 9:
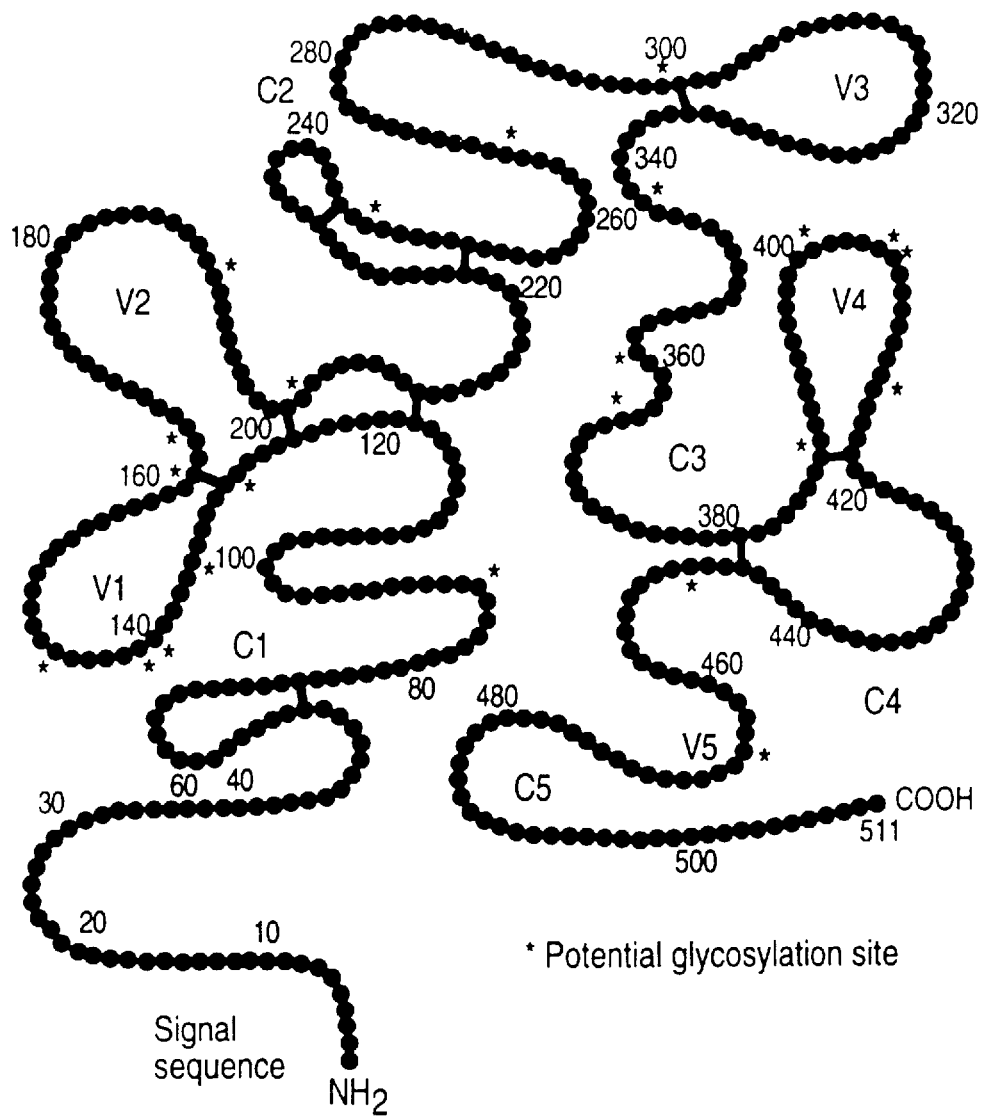
FIG. 9 depicts the amino acid sequence of the mature envelope glycoprotein (gp120) from the $MN_{GNE}$ clone of the MN strain of HIV-1 (SEQ. ID. NO. 1). Hypervariable domains are from 1–29 (signal sequence), 131–156, 166–200,305–332, 399–413, and 460–469. The V and C regions are indicated (according to Modrow et. al., *J. Virology* 61(2):570 (1987). Potential glycosylation sites are marked with a (*).
Figure 10:
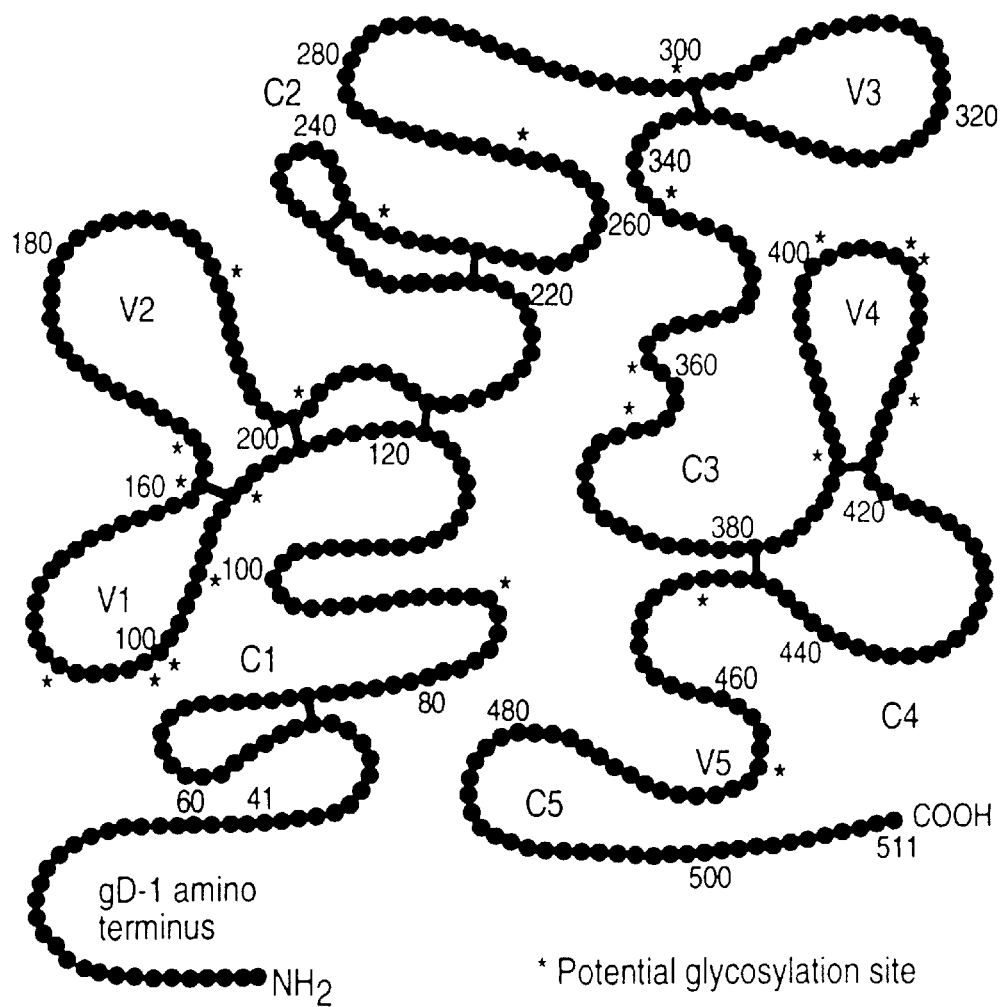
FIG. 10 depicts the amino acid sequence of a fusion protein of the residues 41–511 of the mature envelope glycoprotein (gp120) from the MN clone of the MN strain of HIV-1, and the gD-1 amino terminus from the herpes simplex glycoprotein gD-1. (SEQ. ID. NO. 2). The V and C regions are indicated (according to Modrow et al., *J. Virology* 61(2):570 (1987). Potential glycosylation sites are marked with a (*).

When discussing the amino acid sequences of various isolates and strains of HIV, the most common numbering system refers to the location of amino acids within the gp120 protein using the initiator methionine residue as position 1. The amino acid numbering reflects the mature HIV-1 gp120 amino acid sequence as shown by FIGS. 9 and FIG. 10 [SEQ. ID Nos. 1 and 2]. For gp120 sequences derived from other HIV isolates and which include their native HIV N-terminal signal sequence, numbering may differ. Although the nucleotide and amino acid residue numbers may not be applicable in other strains where upstream deletions or insertions change the length of the viral genome and gp120, the region encoding the portions of gp120 is readily identified by reference to the teachings herein. The variable (V) domains and conserved (C) domains of gp120 are specified according to the nomenclature of Modrow et al. "Computer-assisted analysis of envelope protein sequences of seven human immunodeficiency virus isolates: predictions of antigenic epitopes in conserved and variable regions," *J. Virol*. 61:570–578 (1987).

The first step in identifying the neutralizing epitopes for any region of gp120 is to immunize an animal with gp120 to induce anti-gp120 antibodies. The antibodies can be polyclonal or, preferably, monoclonal. Polyclonal antibodies can be induced by administering to the host animal an immunogenic composition comprising gp120. Preparation of immunogenic compositions of a protein may vary depending on the host animal and the protein and is well known. For example, gp120 or an antigenic portion thereof can be conjugated to an immunogenic substance such as KLH or BSA or provided in an adjuvant or the like. The induced antibodies can be tested to determine whether the composition is specific for gp120. If a polyclonal antibody composition does not provide the desired specificity, the antibodies can be fractionated by ion exchange chromatography and immunoaffinity methods using intact gp120 or various fragments of gp120 to enhance specificity by a variety of conventional methods. For example, the composition can be fractionated to reduce binding to other substances by contacting the composition with gp120 affixed to a solid substrate. Those antibodies which bind to the substrate are retained. Fractionation techniques using antigens affixed to a variety of solid substrates such as affinity chromatography materials including Sephadex, Sepharose and the like are well known.

Monoclonal anti-gp120 antibodies can be produced by a number of conventional methods. A mouse can be injected with an immunogenic composition containing gp120 and spleen cells obtained. Those spleen cells can be fused with a fusion partner to prepare hybridomas. Antibodies secreted by the hybridomas can be screened to select a hybridoma wherein the antibodies neutralize HIV infectivity, as described hereinafter. Hybridomas that produce antibodies of the desired specificity are cultured by standard techniques.

Infected human lymphocytes can be used to prepare human hybridomas by a number of techniques such as fusion with a murine fusion partner or transformation with EBV. In addition, combinatorial libraries of human or mouse spleen can be expressed in *E. coli* to produce the antibodies. Kits for preparing combinatorial libraries are commercially available. Hybridoma preparation techniques and culture methods are well known and constitute no part of the present invention. Exemplary preparations of monoclonal antibodies are described in the Examples.

Following preparation of anti-gp120 monoclonal antibodies, the antibodies are screened to determine those antibodies which are neutralizing antibodies. Assays to determine whether a monoclonal antibody neutralizes HIV infectivity are well known and are described in the literature. Briefly, dilutions of antibody and HIV stock are combined and incubated for a time sufficient for antibody binding to the virus. Thereafter, cells that are susceptible to HIV infection are combined with the virus/antibody mixture and cultured. MT-2 cells or H9 cells are susceptible to infection by most HIV strains that are adapted for growth in the laboratory. Activated peripheral blood mononuclear cells (PBMCS) or macrophages can be infected with primary isolates (isolates from a patient specimens which have not been cultured in T-cell lines or transformed cell lines). Daar et al, *Proc. Natl. Acad. Sci.* USA 87:6574–6578 (1990) describe methods for infecting cells with primary isolates.

After culturing the cells for about five days, the number of viable cells is determined, as by measuring metabolic conversion of the formazan MTT dye. The percentage of inhibition of infectivity is calculated to determine those antibodies that neutralize HIV. An exemplary preferred procedure for determining HIV neutralization is described in the Examples.

Those monoclonal antibodies which neutralize HIV are used to map the epitopes to which the antibodies bind. To determine the location of a gp120 neutralizing epitope, neutralizing antibodies are combined with fragments of gp120 to determine the fragments to which the antibodies bind. The gp120 fragments used to localize the neutralizing epitopes are preferably made by recombinant DNA methods as described hereinafter and exemplified in the Examples. By using a plurality of fragments, each encompassing different, overlapping portions of gp120, an amino acid sequence encompassing a neutralizing epitope to which a neutralizing antibody binds can be determined. A preferred exemplary determination of the neutralizing epitopes to which a series of neutralizing antibodies binds is described in detail in the Examples.

This use of overlapping fragments can narrow the location of the epitope to a region of about 20 to 40 residues. To confirm the location of the epitope and narrow the location to a region of about 5 to 10 residues, site-directed mutagenicity studies are preferably performed. Such studies can also determine the critical residues for binding of neutralizing antibodies. A preferred exemplary site-directed mutagenicity procedure is described in the Examples.

To perform site-directed mutagenicity studies, recombinant PCR techniques can be utilized to introduce single amino acid substitutions at selected sites into gp120 fragments containing the neutralizing epitope. Briefly, overlapping portions of the region containing the epitope are amplified using primers that incorporate the desired nucleotide changes. The resultant PCR products are annealed and amplified to generate the final product. The final product is then expressed to produce a mutagenized gp120 fragment. Expression of DNA encoding gp120 or a portion thereof is described hereinafter and exemplified in the Examples.

In a preferred embodiment described in Example 1, the gp120 fragments are expressed in mammalian cells that are capable of expression of gp120 fragments having the same glycolsylation and disulfide bonds as native gp120. The presence of proper glycolsylation and disulfide bonds provides fragments that are more likely to preserve the neutralizing epitopes than fragments that are expressed in *E. coli*, for example, which lack disulfide bonds and glycosylation or are chemically synthesized which lack glycolsylation and may lack disulfide bonds.

Those mutagenized gp120 fragments are then used in an immunoassay using gp120 as a control to determine the mutations that impair or eliminate binding of the neutralizing antibodies. Those critical amino acid residues form part of the neutralizing epitope that can only be altered in limited ways without eliminating the epitope. Each alteration that preserves the epitope can be determined. Such mutagenicity studies demonstrate the variations in the amino acid sequence of the neutralizing epitope that provide equivalent or diminished binding by neutralizing antibodies or eliminate antibody binding. Although the amino acid sequence of gp120 used in the vaccine preferably is identical to that of a selected HIV isolate for the given geographic region, alterations in the amino acid sequence of neutralizing epitope that are suitable for use in a vaccine can be determined by such studies.

Once a neutralizing epitope is localized to a region of ten to twenty amino acids of gp120, the amino acid sequence of corresponding neutralizing epitopes of other HIV isolates can be determined by identifying the corresponding portion of the gp120 amino acid sequence of the isolate.

Once the neutralizing epitopes for a given region of gp120 are determined, the amino acid sequence of HIV isolates for the geographic region are determined. The complete amino acid sequence for numerous isolates has been determined and is available from numerous journal articles and in databases. In such cases, determination of the amino acid sequence of HIV isolates for the geographic region involves looking up the sequence in an appropriate database or journal article. However, for some isolates, the amino acid sequence information does not include the sequence of the V2 or C4 domains.

When the amino acid sequence of a region of interest for a given isolate is not known, the amino acid sequence can be determined by well known methods. Methods for determining the amino acid sequence of a protein or peptide of interest are well known and are described in numerous references including Maniatis et al., Molecular Cloning—A laboratory Manual, Cold Spring Harbor Laboratory (1984). In addition, automated instruments which sequence proteins are commercially available.

Alternatively, the nucleotide sequence of DNA encoding gp120 or a relevant portion of gp120 can be determined and the amino acid sequence of gp120 can be deduced. Methods for amplifying gp120-encoding DNA from HIV isolates to provide sufficient DNA for sequencing are well known. In particular, Ou et al, *Science* 256:1165–1171 (1992); Zhang et al. *AIDS* 5:675–681 (1991); and Wolinsky *Science* 255:1134–1137 (1992) describe methods for amplifying gp120 DNA. Sequencing of the amplified DNA is well known and is described in Maniatis et al., Molecular Cloning—A Laboratory Manual, Cold Spring Harbor Laboratory (1984), and Horvath et al., An Automated DNA Synthesizer Employing Deoxynucleoside 3'-Phosphoramidites, Methods in Enzymology 154: 313–326, (1987), for example. In addition, automated instruments that sequence DNA are commercially available.

In a preferred embodiment, the isolate is a patient isolate which has not been passaged in culture. It is known that following passage in T-cells, HIV isolates mutate and isolates best suited for growth under cell culture conditions are selected. For example, cell culture strains of HIV develop the ability to form syncytia. Therefore, preferably the amino acid sequence of gp120 is determined from a patient isolate prior to growth in culture. Generally, DNA from the isolate is amplified to provide sufficient DNA for sequencing. The deduced amino acid sequence is used as the amino acid sequence of the isolate, as described hereinbefore.

To determine the percentage each isolate constitutes of total HIV that infects individuals in the geographic region, standard epidemiological methods are used. In particular, sufficient isolates are sequenced to ensure confidence that the percentage of each isolate in the geographic region has been determined. For example, Ichimura et al, *AIDS Res. Hum. Retroviruses* 10:263–269 (1994) describe an epidemiological study in Thailand that determined that there are two strains of HIV present in the region. HIV strains have only recently been present in Thailand and Thailand, therefore has the most homogenous population of HIV isolates known to date. The study sequenced 23 isolates from various parts of the country and determined that only two different amino acid sequences were present in the isolates.

In contrast, HIV has been infecting individuals in Africa for the longest period of any geographic region. In Africa, each of the most common isolates probably constitutes about 5% of the population. In such cases, more isolates would need to be sequenced to determine the percentage each isolate constitutes of the population. Population studies for determining the percentage of various strains of HIV, or other viruses, present in a geographic region are well known and are described in, for example, Ou et al, Lancet 341:1171–1174 (1993); Ou et al, AIDS Res. Hum. Retroviruses 8:1471–1472 (1992); and McCutchan et al., *AIDS Res. Hum. Retroviruses* 8:1887–1895 (1992).

In the United States and western Europe, probably about two to four different neutralizing epitopes in each of the V2, V3, and C4 domains constitute 50 to 70% of the neutralizing epitopes for each domain in the geographic region, as described more fully hereinafter.

Selection Method

Once the amino acid sequence of neutralizing epitopes for strains in a region are determined, gp120 from an HIV strain having gp120 that has an amino acid sequence for a neutralizing epitope in the V2 or C4 domain which sequence is one of the most common in the geographic region is selected. One of the most common neutralizing epitope amino acid sequences means that the strain has an amino acid sequence for at least one neutralizing epitope that is occurs among the most frequently for HIV isolates in the geographic region and thus is present as a significant percentage of the population. For example, if there are three sequences for a neutralizing epitope that constitute 20, 30, and 40 percent of the sequences for that epitope in the region and the remainder of the population is comprised by 2 to 4 other sequences, the three sequences are the most common. Therefore, in African countries, if each of several amino acid sequences constitute about 5% of the sequences for a neutralizing epitope and the remainder of the sequences each constitute less than 1% of the population, the isolates that constitute 5% of the population are the most common.

Preferably, isolates having the most common amino acid sequences for a neutralizing epitope are chosen. By the most common is meant that the sequences occur most frequently in the geographic region. For example, in the United States, the MN isolate has a C4 neutralizing epitope that comprises at least about 45% of the population. The $GNE_8$ isolate has a C4 neutralizing epitope that comprises at least about 45% of the population. Thus either isolate has the most common C4 neutralizing epitope in the region. When gp120 from each isolate is combined in a vaccine, greater than about 90% of the C4 neutralizing epitope sequences are present in the vaccine. In addition, the amino acid sequences for the V3 neutralizing epitope in the MN and $GNE_8$ isolates are substantially similar and comprise about 60% of the population. Therefore, those strains have the two most common neutralizing epitopes for the V3 domain. In the V2 region, the MN isolate amino acid sequences comprises about 10% of the population, and the $GNE_8$ isolate amino acid sequences comprises about 60% of the population. Therefore, the $GNE_8$ strain has the most common neutralizing epitope for the region and the two strains together comprise the two most common neutralizing epitopes for the region. A multivalent gp120 subunit vaccine containing the two isolates contains amino acid sequences for epitopes that constitute about 70% of the V2 domain, about 60% of the V3 domain, and about 90% of the C4 domain for the United States.

In a preferred embodiment of the method, one or more HIV isolates having an amino acid sequence for a neutralizing epitope in the V2 and/or C4 domains that constitute at least about 50% of the population for a selected geographic region are selected. In a more preferred embodiment, isolates having the most common neutralizing epitopes in the V3 domain are also included in the vaccine.

As is clear, once the most common amino acid sequences for the neutralizing epitopes in the V2, V3, and C4 domains are known, an isolate having a common epitope for each region is preferably selected. That is, when only two or three isolates are used for the vaccine, it is preferable to select the isolate for common epitopes in each region, rather than selecting an isolate by analysis of a single region.

In a more preferred embodiment, gp120 from isolates having epitopes that constitute at least 50% of the population for the geographic region for V2, V3, and C4 domains are present in the vaccine. More preferably, the isolates have epitopes that constitute at least 60% of the population for the geographic region for the three domains. Most preferably, 70% or more are included.

In another preferred embodiment, the entire amino acid sequence of the V2 and C4 domains is determined in the selection process. In addition to selecting common sequences for the neutralizing epitopes, isolates having unusual polymorphisms elsewhere in the region are preferably not used for the vaccine isolates.

Vaccine Preparation gp120 from the selected HIV isolate(s) is used to make a subunit vaccine, preferably a multivalent subunit vaccine. Preparation of gp120 for use in a vaccine is well known and is described hereinafter. With the exception of the use of the selected HIV isolate, the gp120 subunit vaccine prepared in the method does not differ from gp120 subunit vaccines of the prior art.

As with prior art gp120 subunit vaccines, gp120 at the desired degree of purity and at a sufficient concentration to induce antibody formation is mixed with a physiologically acceptable carrier. A physiologically acceptable carrier is nontoxic to a recipient at the dosage and concentration employed in the vaccine. Generally, the vaccine is formulated for injection, usually intramuscular or subcutaneous injection. Suitable carriers for injection include sterile water, but preferably are physiologic salt solutions, such as normal saline or buffered salt solutions such as phosphate buffered saline or ringer's lactate. The vaccine generally contains an adjuvant. Useful adjuvants include QS21 which stimulates cytotoxic T-cells and alum (aluminum hydroxide adjuvant). Formulations with different adjuvants which enhance cellular or local immunity can also be used.

Addition excipients that can be present in the vaccine include low molecular weight polypeptides (less than about 10 residues), proteins, amino acids, carbohydrates including glucose or dextrans, chelating agents such as EDTA, and other excipients.

The vaccine can also contain other HIV proteins. In particular, gp41 or the extracellular portion of gp41 can be present in the vaccine. Since gp41 has a conserved amino acid sequence, the gp41 present in the vaccine can be from any HIV isolate. gp160 from an isolate used in the vaccine can replace gp120 in the vaccine or be used together with gp120 from the isolate. Alternatively, gp160 from an isolate having a different neutralizing epitope than those in the vaccine isolates can additionally be present in the vaccine.

Vaccine formulations generally include a total of about 300 to 600 μg of gp120, conveniently in about 1.0 ml of carrier. The amount of gp120 for any isolate present in the vaccine will vary depending on the immunogenicity of the gp120. For example, gp120 from the Thai strains of HIV are much less immunogenic than gp120 from the MN strain. If the two strains were to be used in combination, empirical titration of the amount of each virus would be performed to determine the percent of the gp120 of each strain in the vaccine. For isolates having similar immunogenicity, approximately equal amounts of each isolate's gp120 would be present in the vaccine. For example, in a preferred embodiment, the vaccine includes gp120 from the MN, $GNE_8$, and $GNE_{16}$ strains at concentrations of about 300 μg per strain in about 1.0 ml of carrier. Methods of determining the relative amount of an immunogenic protein in multivalent vaccines are well known and have been used, for example, to determine relative proportions of various isolates in multivalent polio vaccines.

The vaccines of this invention are administered in the same manner as prior art HIV gp120 subunit vaccines. In particular, the vaccines are generally administered at 0, 1, and at 6, 8 or 12 months, depending on the protocol. Following the immunization procedure, annual or bi-annual boosts can be administered. However, during the immunization process and thereafter, neutralizing antibody levels can be assayed and the protocol adjusted accordingly.

The vaccine is administered to uninfected individuals. In addition, the vaccine can be administered to seropositive individuals to augment immune response to the virus, as with prior art HIV vaccines. It is also contemplated that DNA encoding the strains of gp120 for the vaccine can be administered in a suitable vehicle for expression in the host. In this way, gp120 can be produced in the infected host, eliminating the need for repeated immunizations. Preparation of gp120 expression vehicles is described hereinafter.

Production of gp120 gp120 in the vaccine can be produced by any suitable means, as with prior art HIV gp120 subunit vaccines. Recombinantly-produced or chemically synthesized gp120 is preferable to gp120 isolated directly from HIV for safety reasons. Methods for recombinant production of gp120 are described below.

DNA Encoding $GNE_8$ and $GNE_{16}$ gp120 and the Resultant Proteins

The present invention also provides novel DNA sequences encoding gp120 from the $GNE_8$ and $GNE_{16}$ isolates which can be used to express gp120 and the resultant gp120 proteins. A nucleotide sequence of less than about 5 kilobases (Kb), preferably less than about 3 Kb having the nucleotide sequence illustrated in Tables 1 and 2, respectively, encodes gp120 from the $GNE_8$ and $GNE_{16}$ isolates. The sequences of the genes and the encoded proteins are shown below in Tables 1–3. In particular, Table 1 illustrates the nucleotide sequence (SEQ. ID. NO. 27) and the predicted amino acid sequence (SEQ. ID. NO. 28) of the $GNE_8$ isolate of HIV. The upper sequence is the coding strand. The table also illustrates the location of each of the restriction sites.

TABLE 1

```
                                                                        hgiCI
                                                                        banI
                                                                        bsp1286
                                                                        bmyI                    styI
  1    ATGATAGTGA  AGGGATCAG   GAAGAATTGT  CAGCACTTGT  GGAGATGGGG  CACCATGCTC  CTTGGGATGT  TGATGATCTG  TAGTGCTGCA  GAAAAATTGT
       TACTATCACT  TCCCTAGTC   CTTCTTAACA  GTCGTGAACA  CCTCTACCCC  GTGGTACGAG  GAACCCTACA  ACTACTAGAC  ATCACGACGT  CTTTTTAACA
  1    M  I  V  K      G  I  R     K  N  C     Q  H  L  W     R  W  G     T  M  L     L  G  M  L     M  I  C     S  A  A     E  K  L  W
                              kpnI
                              hgiCI
                              banI                                                                        scfI
                              asp718                                                                      pstI
                              acc65I                                                                      bsgI
 101   GGGTCACAGT  CTATTATGGG  GTACCTGTGT  CAGCACCTCC  AACCACCACT  CTATTTTGTG  CATCAGATGC  TAAAGCATAT  GATACAGAGG  TACATAATGT
       CCCAGTGTCA  GATAATACCC  CATGGACACA  GTCGTGGAGG  TTGGTGGTGA  GATAAAACAC  GTAGTCTACG  ATTTCGTATA  CTATGTCTCC  ATGTATTACA
 35    V  T  V     Y  Y  G     V  P  V  W     Q  H  L  P     T  T  T     L  F  C  A     S  D  A     K  A  Y     D  T  E  V     H  N  V
              nspI                                                                  ndeI
              nspHI                                                                                     nspI
                                                                                                        nspHI
                                                                             apoI                       aflIII
 201   TTGGGCCACA  CATGCCTGTG  TACCCACAGA  CCCCAACCCA  CAAGAAATAG  GATTGGAAAA  TGTAACAGAA  AATTTTAACA  TGTGGAAAAA  TAACATGGTA
       AACCCGGTGT  GTACGGACAC  ATGGGTGTCT  GGGGTTGGGT  GTTCTTTATC  CTAACCTTTT  ACATTGTCTT  TTAAAATTGT  ACACCTTTTT  ATTGTACCAT
 68    W  A  T     H  A  C  V     P  T  D     P  N  P     Q  E  I  G     L  E  N     V  T  E     N  F  N  M     W  K  N     N  M  V
              ppu10I                                     hindIII        draIII                         ahaII/draI
              nsiI/avaII
 301   GAACAGATGC  ATGCCGGATAT  AATCAGTTTA  TGGGATCATA  GCTTAAAGCC  TTAACCCCAC  TATGTGTTAC  TTTAAATTGC  ACTGATTTGA
       CTTGTCTACG  TACTCCTATA  TTAGTCAAAT  ACCCTAGTAT  CGAATTTCGG  AATTGGGGTG  ATACACAATG  AAATTTAACG  TGACTAAACT
 101   E  Q  M  H     E  D  I     I  S  L     W  D  Q  S     L  K  P     L  T  P  L     C  V  T     L  N  C     T  D  L  K
                              pvuII
                              nspBII
                        speI
 401   AAAATGCTAC  TAATACCACT  AGTAGCAGCT  GGGAAAGAT  GGAGAGAGGA  GAAATAAAAA  ACTGCTCTTT  CAATGCTCACC  ACAAGTATAA  GAGATAAGAT
       TTTTACGATG  ATTATGGTGA  TCATCGTCGA  CCCCTTTCTA  CCTCTCTCCT  CTTTATTTTT  TGACGAGAAA  GTTACGAGTG  TGTTCATATT  CTCTATTCTA
 135   N  A  T     N  T  T     S  S  S  W     G  K  M     E  R  G     E  I  K  N     C  S  F     N  V  T     T  S  I  R     D  K  M
                                                                             scfI
 501   GAAGAATGAA  TATGCACTTT  TTTATAAACT  TGATGTAGTA  CCAATAGATA  ATGATAATAC  TAGCTATAGG  TTGATAAGTT  GTAACACCTC  AGTCATTACA
       CTTCTTACTT  ATACGTGAAA  AAATATTTGA  ACTACATCAT  GGTTATCTAT  TACTATTATG  ATCGATATCC  AACTATTCAA  CATTGTGGAG  TCAGTAATGT
 168   K  N  E     Y  A  L  F     Y  K  L     D  V  V     P  I  D  N     D  N  T     S  Y  R     L  I  S  C     V  T     V  I  T
              stuI                                              bsp1407I
              haeI                                              bmyI         haeI
 601   CAGGCCTGTC  CAAAGGTGTC  CTTTGAGCCA  ATTATTGTGC  ATTCCCATAC  TTTGCGATTC  TAAAGTGTAG  GTAACACCTC  AGATAAAAAG  TTCAACGGAA
       GTCCGGACAG  GTTTCCACAG  GAAACTCGGT  TAATAACACG  TAAGGGTATG  AAACGCTAAG  ATTTCACATC  CATTGTGGAG  TCTATTTTTC  AAGTTGCCTT
 201   Q  A  C  P     K  V  S     F  E  P     I  P  I  H     Y  C  A     F  A  I  L     K  C  R     D  K  K     F  N  G  T
              bsp1407I
 701   CAGGACCATG  TACAAATGTC  AGCACAGTAC  CCAGTAGTAT  ATGATAATGTGTT  GCTGTTAAAT  CAACTCAACT  GGCAGTTTAG  CAGAAGAAGA
       GTCCTGGTAC  ATGTTTACAG  TCGTGTCATG  GGTCATCATA  TTACATGTACACAA  CGACAATTTA  GTTGAGTTGA  CCGTCAAATC  GTCTTCTTCT
 235   G  P  C     T  N  V     S  T  V  Q     P  V  V  S     M  M  N     L  L  N     T  Q  L     G  S  L  A     E  E  E  E
```

TABLE 1-continued

| | | | | | | | | | |
|---|---|---|---|---|---|---|---|---|---|
| | | | bstYI/xhoII bglII | | | pvuII nspBII | | bsp1407I aseI/asnI/vspI | |
| 801 | AGTAGTAATT TCATCATTAA V V I | CAATGCTAAA GTTACGATTT N A K | ATTTCTCGGA TAAAGAGCCT F S D | AGATCTGCCA TCTAGACGGT R S A N | ACCATAATAG TGGTATTATC T I I V | TACAGCTGAA ATGTCGACTT Q L N | CGAATCTGTA GCTTAGACAT E S V | GAAATTAATT CTTTAATTAA E I N C | GTACAAGACC CATGTTCTGG T R P | CAACAACAAT GTTGTTGTTA N N N |
| 268 | | | | bst1107I accI | | | scfI | | | |
| 901 | ACAAGAAGAA TGTTCTTCTT T R R S | AGAGCATTTT TCTCGTAAAA R A F Y | GTATACATAT CATATGTATA I H I | AGGACCAGGG TCCTGGTCCC G P G | ATGCAACAGG TACGTTGTCC A T G | AGAATAATA TCTTTATTAT E I I T | CCTCCGTATT CCTCGTATT G D I R | GACAAGCACA CTGTTCGTGT Q A H | TTGTAACCTT AACATTGGAA C N L | AGTAGCACAA TCATCGTGTT S S T K |
| 301 | | | ahaIII/draI | | | | | eco81I bsu36I/mstII/sauI | ppuMI eco0109I/draII | |
| 1001 | AATGGAATAA TTACCTTATT W N N | TACTTTAAAA ATGAAATTT T L K | CAGATAGTTA GTCTATCAAT Q I V T | CAAAATTAAG GTTTTAATTC K L R | AGAACATTTT TCTTGTAAAA E H F | AATAAAACAA TTATTTTGTT N K T I | TAGTCTTTAA ATCAGAAATT V F N | TCACTCCTCA AGTGAGGAGT H S S | GGAGGGGACC CCTCCCCTGG G G D P | CAGAAATTGT GTCTTTAACA E I V |
| 335 | | | apoI | | scaI | | | | | eco57I |
| 1101 | AATGCACAGT TTACGTGTCA M H S | TTTAATTGTG AAATTAACAC F N C G | GAGGGAATT CTCCCCTTAA G E F | TTTCTACTGT AAAGATGACA F Y C | CACTGTTTAA GTGACAAATT L F N | AATACAACAC TTATGTTGTG N T T P | TAGTACTTGG ATCATGAACC S T W | AATTATACTT TTAATATGAA N Y T Y | ATACTTGAAA TATGAACTT T W N | TAATACTGAA ATTATGACTT N T E |
| 368 | | | | | | nspI nspHI afIIII | | | | |
| 1201 | GGGTCAAATG CCCAGTTTAC G S N D | ACACTGGAAG TGTGACCTTC T G R | AAATATCACA TTTATAGTGT N I T | CTCCAATGCA GAGGTTACGT L Q C R | GAATAAAACA CTTATTTTGT I K Q | AATTATAAAC TTAATATTTG I I N | ATGTGGCAGG TACACCGTCC M W Q E | AAGTAGGAAA TTCATCCTTT V G K | AGCAATGTAT TCGTTACATA A M Y | GCCCCTCCA CGGGGAGGGT A P P I |
| 401 | | | mamI bsaBI | | | | | | bstYI/xhoII bglII | gsuI/bpmI ecoNI |
| 1301 | TAAGAGGACA ATTCTCCTGT R G Q | AATTAGATGC TTAATCTACG S S N I | TTACAGGGCT AATGTCCCGA T G L | ATATAAATAT TATATTTATA Y K Y | GCTATTAACA CGATAATTGT L L T | AAAGTAGTAA TTTCATCATT K V V K | AGAGATGTG TCTCTACCAC R D G G | GTAATAACAC CATTATTGTG N N S | CGAAACCGA GCTTTGGCTC E T E | ATCTTCAGAC TAGAAGTCTG I F R P | CTGGAGAGG GACCTCCTCC G G G |
| 435 | | | | | | | | | styI | earI/ksp632I |
| 1401 | AGATATGAGG TCTATACTCC D M R | GACAATTGGA CTGTTAACCT D N W R | GAAGTGAATT CTTCACTTAA S E L | ATATAAATAT TATATTTATA I E P | AAATTGAACC TTTAACTTGG I E P | | GCACCCACCA CGTGGGTGGT A P T K | AGGCAAAGA TCCGTTTCT A K R | AAGAGTGATG TTCTCACTAC R V M | | |
| 468 | | | | | | | | | | alwNI |
| 1501 | CAGAGAGAAA GTCTCTCTTT Q R E K | AAAGAGGAGT TTTCTCCTCA R G S | GCTGTGTTCC CGACACAAGG A V F L | TTTGGGTTCTT AAACCAAGAA G F L | CAATTTGCTG GTTAAACGAC Q F A | GGGAGCAGCA CCCTCGTCGT G A A | GGAAAGCACTA CCTTCGTGAT G S T M | TGGGCCGAGC ACCCGGCTCG S V T | GTCCAGTGACG CAGTCACTGC L T V Q | |
| 501 | haeI | | | | | | | | | |
| 1601 | AGGCCAGACT TCCGGTCTGA | AATTATTGTCT TTAATAACAGA | GGTATATGCT CCATATCACG | AACAGCAGAA TTGTCGTCTT | CAATTTGCTG GTTAAACGAC | AGGGCTATTG TCCCGATAAC | AGGCCGAACA TCCGGCTTGT | GCATCTGTTG CGTAGACAAC | CAACTCACAG GTTGAGTGTC | TCTGGGGCAT AGACCCCGTA |

TABLE 1-continued

| | | | | | | | | | | | |
|---|---|---|---|---|---|---|---|---|---|---|---|
| 535 | A R L | L L S | G I V Q | Q Q N | N L L | R A I E | A E Q | H L L | Q L T V | W G I | |
| | | gsuI/bpmI | | | | alwNI | | | | | |
| 1701 | CAAGCAGCTC | CAGGCAAGAG | TCCTGCTCTGT | GGAGAGATAC | CTAAAGGATC | AACAGCTCCT | GGGGATTTGG | GGTTGCTCTG | GAAAACTTCAT | CTGCACCACT | |
| | GTTCGTCGAG | GTCCGTTCTC | AGGACCGACA | CCTCTCTATG | GATTTCCTAG | TTGTCGAGGA | CCCCTAAACC | CCAACGAGAC | CTTTTGAGTA | GACGTGGTGA | |
| 568 | K Q L | Q A R V | L A V | E R Y | L K D Q | Q L L | G I W | G C S G | K L I | C T T | |
| | styI | bsmI | | | | | | | | | hindIII |
| 1801 | GCTGTGCCTT | GGAATGCTAG | TTGGACTAAT | AAATCTCTGG | ATAAGATTTG | GGATAACATG | ACCTGGATGG | AGTGGGAAAG | AGAAATTGAC | AATTACACAA | |
| | CGACACGGAA | CCTTACGATC | AACCTGATTA | TTTAGAGACC | TATTCTAAAC | CCTATTGTAC | TGGACCTACC | TCACCCTTTC | TCTTTAACTG | TTAATGTGTT | |
| 601 | A V P W | N A S | W S N | K S L D | K I W | D N M | T W M E | W E R | E I D | N Y T S | |
| 1901 | GCTTAATATA | CAGCTTAATT | GAAGAATCGC | AGAACCAACA | AGAAAAAAAT | GAACAGAGAAT | TATTGGAATT | AGATAAATGG | GCAAGTTTGT | GGAATTGGTT | |
| | CGAATTATAT | GTCGAATTAA | CTTCTTAGCG | TCTTGGTTGT | TCTTTTTTTA | CTTGTTCTTA | ATAACCTTAA | TCTATTTACC | CGTTCAAACA | CCTTAACCAA | |
| 635 | L I Y | S L I | E E S Q | N Q Q | E K N | L E L | L E L | D K W | A S L W | N W F | |
| | | | | sspI | | | | | scfI | | |
| 2001 | TGACATAACA | AAATGGCTGT | GGTATATAAA | AATATTCATA | ATGATAGTAG | AGGCCTTGGT | AGGTTTAAGA | ATAGTTTTTA | CTGTACTTTC | TATAGTGAAT | |
| | ACTGTATTGT | TTTACCGACA | CCATATATTT | TTATAAGTAT | TACTATCATC | TCCGGAACCA | TCCAAATTCT | TATCAAAAAT | GACATGAAAG | ATATCACTTA | |
| 668 | D I T | K W L W | Y I K | I F F I | M I V G | G L V | G L R | I V F T | V L S | I I V N | |
| 2101 | AGAGTTAGGA | AGGGATACTC | ACCATTATCG | TTCCAGACCC | ACCTCCCAGC | CCCGAGGGGA | CTCGACAGGC | CCGAAGGAAC | CGAAGAAGAA | GGTGGAGAGC | |
| | TCTCAATCCT | TCCCTATGAG | TGGTAATAGC | AAGGTCTGGG | TGGAGGGTCG | GGGCTCCCCT | GAGCTGTCCG | GGCTTCCTTG | GCTTCTTCTT | CCACCTCTCG | |
| 701 | R V R K | G Y S | P L S | F Q T H | L P A | P R G | L D R P | E G T | E E E E | G G E R | |
| | | xcmI | | | | bspMI | | | eco57I | | |
| | | bstYI/xhoII | | | | salI | | | earI/ksp632I | | |
| | | | | | | hincII/hindII | | | | | |
| | | | | | | accI | | | | | |
| 2201 | GAGACAGAGA | CAGATCCAGT | CGATTAGTGA | ATGGATTCTT | AGCAATTGTC | TGGGGAGCCT | TGCGGAGGCT | GTGCCTCTTC | AGCTACCACC | GCTTGAGAGA | |
| | CTCTGTCTCT | GTCTAGGTCA | GCTAATCACC | TACCTAAGAA | TCGTTAACAG | ACCCAGCTGG | ACGCCTCCGA | CACGGAGAAG | TCGATGGTGG | CGAACTCTCT | |
| 735 | D R D | R S S | R L V D | G F L | A I V | W V D L | R S L | C L F | S Y H R | L R D | |
| | | | | | munI | | | sspI | | scfI | |
| 2301 | CTTACTCTTG | ATTGCAGCGA | GGATTGTGGA | ACTTCTGGGA | CGCAGGGGT | GGGAACCCCT | TGAGGGAACA | TGGAATCTCC | TACAGTATTG | GATTCAGGAA | |
| | GAATGAGAAC | TAACGTCGCT | CCTAACACCT | TGAAGACCCT | GCGTCCCCCA | CCCTTCGGGA | ACTCCCTTGT | ACCTTAGAGG | ATGTCATAAC | CTAAGTCCTT | |
| 768 | L L L | I A A R | I V E | L L G | R R G W | E A L | E G T | W N L L | Q Y W | I Q E | |
| | | | | | | | | alwNI | | | |
| 2401 | CTAAAGAATA | GTGCTGTTAG | CTTGCTCAAT | GCCACAGCCA | TGAGGGAACA | GATAGGGTTA | TAGCAGTAGC | TAGAAATAGT | ACAAAGAGCT | TATAGAGCTA | |
| | GATTTCTTAT | CACGACAATC | GAACGAGTTA | CGGTGTCGGT | ACTCCCTTGT | CTATCCCAAT | ATCGTCATCG | ATCTTTATCA | TGTTTCTCGA | ATATCTCGAT | |
| 801 | L K N S | A V S | L L N | A T A I | E G T | D R V I | A V A | E I V | Q R A | Y R A I | |
| 2501 | TTCTCCACAT | ACCCACACGA | ATAAGACAGG | GCTTTGGAAAG | TGAGGGAACA | TAA | | | | | |
| | AAGAGGTGTA | TGGGTGTGCT | TATTCTGTCC | CGAACCTTTC | ACTCCCTTGT | ATT | | | | | |
| 835 | L H I | P T R | I R Q G | L E R | A L L | O | | | | | |

Table 2 illustrates the nucleotide sequence and the predicted amino acid sequence of the $GNE_{16}$ isolate of HIV. The upper sequence is the coding strand. The table also illustrates the location of each of the restriction sites. The first four pages of the table are from one clone of the gene and the second three pages of the table are from another clone of the gene. The sequences of the clones differ by about 2%. (The nucleotide sequences are SEQ. ID. NOs. 29 and 31 respectively. The amino acid sequences are SEQ. ID. NOs. 30, 32, and 33) It is noted that each of the sequences includes a stop codon. A gene sequence that encodes full length gp120 can be made by rep

TABLE 2

```
                                                                   hgiCI
                                                                   banI
                                                                   bsp1286
                                                                   bmyI                               scfI
                                                                              styI                    pstI
                                                                                          scfI        bsgI
  1  ATGAGAGTGA  AGGGGATCAG  GAGGAATTAT  CAGCACTTGT  GGAGATGGGG  CACCATGCTC  CTTTGGATAT  TGATGATCTG  TAGTGCTGCA  GGGAAATTGT
     TACTCTCACT  TCCCCTAGTC  CTCCTTAATA  GTCGTGAACA  CCTCTACCCC  GTGGTACGAG  GAACCCTATA  ACTACTAGAC  ATCACGACGT  CCCTTTAACA
  1  M  R  V  K    R  G  I  R    R  N  Y    Q  H  L  W    R  W  G    T  M  L    L  G  I  L    M  I  C    S  A  A    G  K  L  W kpnI
                        hgiCI
                        banI
                        asp718
                        acc65I
101  GGGTCACAGT  CTATTATGGG  GTACCTGTGT  GGAAAGAAAC  CTATTTTGTG  AACCACACCT  CATCAGATGC  TAAAGCATAT  GATACAGAGA  TACATAATGT
     CCCAGTGTCA  GATAATACCC  CATGGACACA  CCTTTCTTTG  GATAAAACAC  TTGGTGTGGA  GTAGTCTACG  ATTTCGTATA  CTATGTCTCT  ATGTATTACA
 35  V  T  V    Y  Y  G    V  P  V  W    K  E  T    L  F  C  A    T  T  T    S  D  A    K  A  Y    D  T  E  I    H  N  V nspI                                                                                            ndeI
              nspHI
201  TTGGGCCACA  CATGCCCTGTG  TACCCACAGA  CCCCAACCCA  TATTGGAAAA  CAAGAAGTAG  TGTGACAGAA  TAAAGCATAT  TAAAGCATAT  TAACATGGTG
     AACCCGGTGT  GTACGGGACAC  ATGGGTGTCT  GGGGTTGGGT  ATAACCTTTT  GTTCTTCATC  ACACTGTCTT  ATTTCGTATA  ATTTCGTATA  ATTGTACCAC
 68  W  A  T    H  A  C  V    P  T  D    P  N  P    L  E  N    Q  E  V  V    V  T  E    N  F  N  M    W  K  N  V ppu10I
         nsiI/avaII                                  ahaIII/draI                                                   draI
301  GAACAGATGC  ATGAGGATAT  AATCAGTTTA  TGGGATCAAA  GTTTAAAGCC  ATGTGTAAAA  TGTGACAGAA  TTAACCCCAC  TCTGTGTTAT  ACTGATGCGG
     CTTGTCTACG  TACTCCTATA  TTAGTCAAAT  ACCCTAGTTT  CAAATTTCGG  TACACATTTT  ACACTGTCTT  AATTGGGGTG  AGACACAATG  TGACTACGCC
101  E  Q  M  H    E  D  I    I  S  L    W  D  Q  S    L  K  P    C  V  K    L  T  P  L    C  V  T    T  D  A  G gsuI/bpmI
401  GGAATACTAC  TAATACCAAT  AGTAGTAGCA  GGGAAAAGCT  GGGAAAAGGA  CCTCTTTCCT  GAGAGAAGAT  ACAAGCGTGA  CAATATCACC  GAGATAAGAT
     CCTTATGATG  ATTATGGTTA  TCATCATCGT  CCCTTTTCGA  CCCTTTTCCT  GGAGAAAGGA  CTCTCTTCTA  TGTTCGCACT  GTTATAGTGG  CTCTATTCTA
135  N  T  T    N  T  N    S  S  S  R    E  K  L    E  K  G    E  I  K  N    T  S  V  R    N  I  T    D  K  M
                        421, reverse scfI
501  GCAGAAAGAA  ACTGCACTTT  ACAGGCCTGT  TTAATAAACT  TGATATAGTA  CCAATAGATG  ATGATGATAG  AGGAATAGTA  CATTTCTGTA  GTTGATAAGT
     CGTCTTTCTT  TGACGTGAAA  TGTCCGGACA  AATTATTTGA  ACTATATCAT  GGTTATCTAC  TACTACTATC  TCCTTATCAT  GTAAAGACAT  CAACTATTCA
168  Q  K  E    T  A  L  F    Q  A  C    N  K  L    D  I  V    P  I  D  D    D  D  R    R  N  S  T    H  F  C  T    L  I  S
         43r2, reverse                                                                                     scaI stuI
                haeI                                                           bsp1407I                     haeI
601  TGTAACACCT  CAGTCAATTAC  ACAGGCCTGT  CCAAAGGTAT  CATTTGAGCC  AATTCCCATA  CATTTCTGTA  CCCCGGCTGG  TTTTGCCCTT  CTAAAGTGTA
     ACATTGTGGA  GTCAGTAATG  TGTCCGGACA  GGTTTCCATA  GTAAACTCGG  TTAAGGGTAT  GTAAAGACAT  GGGGCCGACC  AAAACGGGAA  GATTTCACAT
201  C  N  T  S    V  I  T    Q  A  C    P  K  V  S    F  E  P    I  A  P  I    H  F  C  T    P  A  G    F  A  L    L  K  C  N 701  ATAATAAGAC  GTTCAATGGA  GTTCAAGTTACCT  TCAGGACCAT  CAGCACAGTA  ATGGAATTAG  GCCAGTAGTA  TCAACTCAAC  AGTTGAGTTG  TGCTGTTAAA
     TATTATTCTG  CAAGTTACCT  CAAGTTCCTGGA  AGTCCTGGTA  GTCGTGTCAT  TACCTTAATC  CGGTCATCAT  AGTTGAGTTG  TCAACTCAAC  ACGACAATTT
```

TABLE 2-continued

| | | | | | | | | | | | | |
|---|---|---|---|---|---|---|---|---|---|---|---|---|
| 235 | N | K | T | F | N | G | S | G | P | C | K N V | S T V | Q C T H | G I R | P V V | S T Q L | L L N |
| | | | | | | | | | | | bstYI/xhoII bglII apoI | | | pvuII nspII | | aseI/asnI/vspI |
| 801 | TGGCAGTCTA | ACCGTCACAT | TGTACAAGAC | GCAGAAGGAG | CGTCTTCCTC | AGGTAGTAAT | TCCATCATTA | TAGATCTGAA | AATTTCACGA | ACAATGCTAA | ACACCATAATA | AACCATATAA | CAGAACCAGT | GTCTTGGTCA | AAAAATTAAT |
| | | | | | | | | | | | TAAAGTGCT | TGTTACGATT | TTGGTACTAT | CATGTCGACT | GTCTTGGTCA | TTTTTAATTA |
| 268 | G S L | | | A E G E | | V V I | | R S | | N F T N | | N A K | T I I | V Q L T | E P V | K I N |
| | | | | | | | | | | | | | | ˆf1,forward | | |
| | bsp1407I | | | | | | | bst1107I | | | | | | | | |
| | | | | | | | | accI scfI | | | | | | | | |
| 901 | TGTACAAGAC | CCAACAACAA | TACAAGAAAA | AGTATACCTA | TAGGACCAGG | ATCCTGGTCC | GAGAGCATTT | CTCTCGTAAA | TATGCAACAG | ATACGTTGTC | GAGACATAAT | TCCTTTATAT | AGGAAATATA | AGACAAGCAC | TCTGTTCCTG |
| 301 | C T R P | N N N | T R K | S I P I | G P G | | | R A F | Y A T G | | D I H | G N I | R Q A H |
| | | | | ˆ875,reverse | | | | | | | | | | | |
| | | | | | | | | | | | | | eco81I | | |
| | | | | | | | | | | | | | bsu36I/mstII/sauI | | |
| 1001 | ATTGTAACCT | TAGTAGAACA | GACTGGAATA | ACACTTTAGG | ACAGATAGTT | GAAAAATTAA | CTCTTGTTAA | TGGGAATAAA | ACAATAATCT | TTAATCACTC |
| | TAACATTGGA | ATCATCTTGT | CTGACCTTAT | TGTGAAATCC | TGTCTATCAA | CTTTTTAATT | GAGAACAATT | ACCCTTATTT | TGTTATTAGA | AATTAGTGAG |
| 335 | C N L | S R T | D W N N | T L G | Q I V | E K L R | E Q F | G N K | T I I F | N H S |
| | ppuMI | | | | | | apoI | | | scaI | |
| | eco0109I/draII | | | | | | | | | | |
| 1101 | CTCAGGAGGG | GACCCAGAAA | TTGTAATGCA | CAGTTTTAAT | TGTAGAGGGG | AATTTTTCTA | CTGTAATACA | ACACAATTGT | TTGACAGTAC | TTTGGGATAAT |
| | GAGTCCTCCC | CTGGGTCTTT | AACATTACGT | GTCAAAATTA | ACATCTCCCC | TTAAAAAGAT | GACATTATGT | TGTGTTAACA | AACTGTCATG | AACCCTATTA |
| 368 | S G G | D P E I | V M H | S F N | C R G E | F F F Y | C N T | T Q L F | D S T | W D N |
| | | | | | | | | | nspI | | |
| | | | | | | | | | nspHI | | |
| | earI/ksp632I | | | | | | | | afIII | | |
| | eco57I | | | | | | | | | | |
| 1201 | ACTAAAGTGT | CAAATGGCAC | TAGCACTGAA | GAGAATAGCA | CCCATGCAGA | ATAAAGCAAA | TATTTCGTTT | GTGGCAGGAA | CACCGTCTT | GTAGGAAAAG |
| | TGATTTCACA | GTTTACCGTG | ATCGTGACTT | CTCTTATCGT | GGGTACGTCT | TATTTCGTTT | ATAAAGCAAA | CACCGTCCTT | CATCCTTTTC |
| 401 | T K V S | N G T | S T E | E N S T | P C R | I K Q I | V N M | W Q E | V G K A |
| | gsuI/bpmI | | | | sspI | | | | | bsaI |
| | ecoNI | | | | | | | | | |
| 1301 | CCCTCCCATC | AGAGGACAAA | CCCTCCTGTT | TTAGATGTTC | ATCAAATATT | ACAGGGTTGC | TATTAACAAG | AGATGGAGGT | AGTAACAACA | GCATGAATGA |
| | GGGAGGGTAG | TCTCCTGTTT | GGACCTCAAG | AATCTACAAG | TAGTTTATAA | TGTCCCAACG | ATAATTGTTC | TCTACCTCCA | TCATTGTGT | CGTACTTACT |
| 435 | P P I | R G Q I | R C S | F N | S N I | T G L L | L T R | D G G | S N N S | M N E |
| | ˆ2,16.7f3,forward | | | | | | | | | |
| | earI/ksp632I | | munI | | | | | | | |
| 1401 | GACCTTCAGA | CCTGGAGGAG | GAGATATGAG | GGACAATTGG | AGAAGTGAAT | TAAAGTAGTA | AAAATTGAAC | TTGTAAACAT | CATTAGGAGT | AGCACCCACC |
| | CTGGAAGTCT | GGACCTCCTC | CTCTATACTC | CCTGTTAACC | TCTTCACTTA | ATTTCATCAT | TTTTAACTTG | AACATTTGTA | GTAATCCTCA | TCGTGGGTGG |
| 468 | T F R | P G G | D M R | D N W | R S E L | Y K V V | K I E P | V N M | L G V | A P T |
| | c4rev4,reverse | | | | | | | | | |
| | | | | | styI | | | | | styI |
| 1501 | AAGGCAAAGA | GAAGAGTGGT | GCAGAGAGAA | AAAAGAGCAG | TGGGAATAGG | AGCTGTGTTC | CTTGGGTTCT | TAGGAGCAGC | AGGAAGCACT | ATGGGCGCAG |
| | TTCCGTTTCT | CTTCTCACCA | CGTCTCTCTT | TTTTCTCGTC | ACCCTTATCC | TCGACACAAG | GAACCCAAG | ATCCTCGTCG | TCCTTCGTGA | TACCCGCGTC |

TABLE 2-continued

| | | | | | | | | | | | | | |
|---|---|---|---|---|---|---|---|---|---|---|---|---|---|
| 501 | K A K R | R V V | Q R E | K R A V | G I G | A V F | L G F L | G A A | G S T | M G A A | | | |
| 1601 | CGTCAATAAC | GCTGACGGTA | CAGGCCAGAC | TATTATTGTC | TGGTATAGTG | CAACAGCAGA | ACAATTTGCT | GAGGGCTATT | GAGGCGCAAC | AGCATCTGTT | | | |
| | GCAGTTATTG | CGACTGCCAT | GTCCGGTCTG | ATAATAACAG | ACCATATCAC | GTTGTCGTCT | TGTTAAACGA | CTCCCGATAA | CTCCGCGTTG | TCGTAGACAA | | | |
| 535 | S I T | L T V | Q A R L | L L S | G I V | Q Q Q N | N L L | R A I | E A Q Q | H L L | | | |
| | | | haeI | ^43f5,forward | | | | | alwNI | | | | |
| | | | | | | | | | ^43r3,reverse | | | | |
| 1701 | GCAACTCATA | GTCTGGGGCA | TCAAGCAGCT | CCAGGCAAGA | GTCCTGCTG | TGGAAAGATA | CCTAAGGGAT | CAACAGCTCC | TGGGGATTTG | GGGTTGCTCT | | | |
| | CGTTGAGTAT | CAGACCCCGT | AGTTCGTCGA | GGTCCGTTCT | CAGGACGAC | ACCTTTCTAT | GGATTCCCTA | GTTGTCGAGG | ACCCCTAAAC | CCCAACGAGA | | | |
| 568 | Q L I | V W G I | K Q L | Q A R | V L A V | E R Y | L R D | Q Q L L | G I W | G C S | | | |
| | | | gsuI/bpmI | | | | eco81I | alwNI | | | | | |
| | | | | | | | bsu36I/mstII/sauI | | | | | | |
| 1801 | GGAAAACTCA | TTTGCACCAC | CTCAGTGCCT | TGGAATGCTA | GTTGGAGTAA | TAAATCTCTA | GATAAGATTT | GGATAACAAC | GACCTGAATG | GAGTGGGAAA | | | |
| | CCTTTTGAGT | AAACGTGGTG | GAGTCACGGA | ACCTTACGAT | CAACCTCATT | ATTTAGAGAT | CTATTCTAAA | CCCTATTGTA | CTGGACTTAC | CTCACCCTTT | | | |
| 601 | G K L I | C T T | S V P | W N A S | W S N | K S L | D K I W | D N M | T W M | E W E R | | | |
| | | hindIII | styI | | | xbaI | | | | | | | |
| 1901 | GAGAAATTGA | GAATTACACA | AGCTTAATAT | ACACCTTAAT | TGAAGAATCG | CAGAACCAAC | AAGAAAAGAA | TGAACAAGAC | TTATTGGAAT | TGGATCAATG | | | |
| | CTCTTTAACT | CTTAATGTGT | TCGAATTATA | TGTGGAATTA | ACTTCTTAGC | GTCTTGGTTG | TTCTTTTCTT | ACTTGTTCTG | AATAACCTTA | ACCTAGTTAC | | | |
| 635 | E I E | N Y T | S L I Y | T L I | E E S | Q N Q Q | E K N | E Q D | L L E L | D Q W | | | |
| | scfI | | | | | sspI | | | | | | | |
| 2001 | GGCAAGTCTG | TGGAATTCGT | TTAGCATAAC | AAAATGGCTG | TGGTATATAA | AAATATTCAT | AATGATAGTT | GGAGGCTTGG | TAGGTTTAAG | AATAGTTTTT | | | |
| | CCGTTCAGAC | ACCTTAACCA | AATCGTATTG | TTTTACCGAC | ACCATATATT | TTTATAAGTA | TTACTATCAA | CCTCCGAACC | ATCCAAATTC | TTATCAAAAA | | | |
| 668 | A S L | W N W F | S I T | K W L | W Y I K | I F F I | M I V | G G L V | G L R | I V F | | | |
| | | | ^43f6,forward | | | | | | aval bsaI | | | | |
| | | | | ^2000,reverse | | | | | | | | | |
| 2101 | GCTGTACTTT | CTATAGTGAA | TAGAGTTAGG | CAGGGATACT | CACCATTATC | GTTTCAGACC | CGCCTCCCAG | CCCCGAGGAG | ACCCGACAGG | CCCGAAGGAA | | | |
| | CGACATGAAA | GATATCACTT | ATCTCAATCC | GTCCCTATGA | GTGGTAATAG | CAAAGTCTGG | GCGGAGGGTC | GGGGCTCCTC | TGGGCTGTCC | GGGCTTCCTT | | | |
| 701 | A V L S | I V N | R V R | Q G Y S | P L S | F Q T | R L P A | P R R | P D R | P E G I | | | |
| | | | | | | bstYI/xhoII | | | | eco57I | | | |
| | | | | | | xcmI | | | | earI/ksp632I | | | |
| 2201 | TCGAAGAAGA | AGGTGGAGAG | CAAGGACAGAG | ACAGATCCAT | TCGCTTAGTG | GATGGATTCT | AACTTCTGGG | CTGGGACGAC | CTACGGAGCC | TGTGCCTCTT | | | |
| | AGCTTCTTCT | TCCACCTCTC | GTTCCTGTCT | TGTCTAGGTA | AGCGAATCAC | CTACCTAAGA | TTGAAGACCC | GACCCTGCTG | GATGCCTCGG | ACACGGAGAA | | | |
| 735 | E E E | G G E | Q G R D | R S I | R L V | D G F L | L L G | W D D | L R S L | C L F | | | |
| 2301 | CAGCTACCAC | CGCTTGAGAG | ACTTACTCTT | GATTGCAACG | AGGATTGTGG | AACTTCTGGG | ACGCAGGGGG | TGCGTCCCCC | TGGGAAGCCC | GTGGAATCTC | | | |
| | GTCGATGGTG | GCGAACTCTC | TGAATGAGAA | CTAACGTTGC | TCCTAACACC | TTGAAGACCC | TGCGTCCCCC | ACGCAGGGGG | ACCCTTCGGG | CACCTTAGAG | | | |
| 768 | S Y H | R L R D | L L L | I A T | R I V E | L L G | R R G | W E A L | K Y W | W N L | | | |
| | scfI | | | | | | | | sspI | | | | |
| 2401 | CTACAGTATT | GATGTCATAA | GGATTCAGGA | ACTAAAGAAT | GCTTGCTTAA | AGTGCTGTTA | CTGAGGGGAC | CTGAGGGGAC | AGATAGGGTT | TTAGAAGTAT | | | |
| | GATGTCATAA | CTACAGTATT | CCTAAGTCCT | TGATTTCTTA | CGAACGAATT | TCACGACAAT | ACAGTGTCGG | GACTCCCCTG | TCTATCCCAA | AATCTTCATA | | | |
| 801 | L Q Y W | I Q E | L K N | S A V S | V T A | E G T | D R V | L E V L | | | | | |

TABLE 2-continued

```
2501  TACAAAGAGC  TTATAGAGCT  ATTCTCCACA  TACCTACAAG  AATAAGACAG  GGCTTGGAAA  GGGCTTTGCT  ATAA
      ATGTTTCTCG  AATATCTCGA  TAAGAGGTGT  ATGGATGTTC  TTATTCTGTC  CCGAACCTTT  CCCGAAACGA  TATT
835    Q  R  A    Y  R  A     I  L  H  I    P  T  R     I  R  Q     G  L  E  R    A  L  L    O hgiCI                                    scfI
                  earI/ksp632I                                                 banI                                    pstI
                                                                               bsp1286                                 bsgI
                                                                               bmyI                      styI          scfI
  1   ATGAGAGTGA  AGAGGATCAG  GAGGAATTAT  CAGCACTTGT  GGAAATGGGG  CACCATGCTC  CTTGGGATGT  TGATGATCTG  TAGTGCTGCA  GGAAAATTGT
      TACTCTCACT  TCTCCTAGTC  CTCCTTAATA  GTCGTGAACA  CCTTTACCCC  GTGGTACGAG  GAACCCTACA  ACTACTAGAC  ATCACGACGT  CCTTTTAACA
  1    M  R  V  K    R  I  R    R  N  Y     Q  H  L  W    K  W  G    T  M  L     L  G  M  L     M  I  C       S  A  A     G  K  L  W kpnI
                              hgiCI
                              banI
                              asp718
                              acc65I
                                                                                         ndeI
101   GGGTCACAGT  CTATTATGGG  GTACCTGTGT  TACCCACAGA  AACCCACCACT  CAAGAGTAG  CTATTTTGTG  TAAAGCATAT  GATACAGAGA  TACATAATGT
      CCCAGTGTCA  GATAATACCC  CATGGACACA  ATGGGTGTCT  TTGGTGGTGA  GTTCTTCATC  GATAAAACAC  ATTTCGTATA  CTATGTCTCT  ATGTATTACA
 35    V  T  V    Y  Y  G     V  P  V  W     P  T  D      T  T  T    Q  E  V  V    L  F  C  A     K  A  Y       D  T  E  I       H  N  V nspI
                nspHI                                                                      nspI
                                                                                           nspHI
                ppu10I                                                            apoI     afIIII
                nsiI/avaIII
201   TTTGGCCACA  CATGCCCTGT  TACCCACAGA  TAATTGGAAA  CAAGAGTAG  CCCCAACCCA  TGTGCAGAA  AATTTTAACA  TGTGAAAAAA  TAACATGGTG
      AACCCGGTGT  GTACGGACAC  ATGGGTGTCT  ATAACCTTTT  GTTCTTCATC  GGGTTGGGT  ACACTGTCTT  TTAAAATTGT  ACACCTTTTT  ATTGTACCAC
 68    W  A  T    H  A  C  V    P  T  D       L  E  N     Q  E  V  V    P  N  P      V  T  E      N  F  N  M      W  K  N      N  M  V draIII
301   GAACAGATGC  TAATACCAAT  AGTAGTAGCG  AATCAGTTTA  TGGGATCAAA  GTCTAAAGCC  ACTGCTCTTT  TTAACCCCAC  TTTAAATTGC  ACTGATGCGG
      CTTGTCTACG  ATTATGGTTA  TCATCATCGC  TTAGTCAAAT  ACCCTAGTTT  CAGATTTCGG  TGACGAGAAA  AATTGGGGTG  AAATTTAACG  TGACTACGCC
101    E  Q  M  H      N  T  N      S  S  S  G      I  S  L       W  D  Q  S     L  K  P       L  T  P  L        C  V  T      L  N  C      T  D  A  G gsuI/bpmI
                                                                                                     ahaIII/draI
401   GAAACAGAAGCT  GGAGAAAGA  TGATATAGTA  TTAATAAACT  GGGAAAAGCT  GGAGAAAGA  CTCCTTTCCT  ACTGCTCTTT  TTTAAATTGC  ACTGATGCGG
      CTTTGTCTTCGA  CCTCTTTCT  ACTATATCAT  AATTATTTGA  CCCTTTTCGA  CCTCTTTCT  GAGGAAAGGA  TGACGAGAAA  AAATTTAACG  TGACTACGCC
135    N  T  T        N  T  N       D  I  V        N  K  L        E  K  G       E  K  G         C  S  F          T  S  M  R        D  K  M scfI
                                                                                           scaI     ctaactatag
501   GCAGAGAGAA  ACTGCACTTT  TTAATAAACT  TGATATAGTA  ACTATATCAT  CCAATGATG  GGTTTCCATA  AGGAATAGTA  CTAACTATAG  GTTGATAAGT
      CGTCTCTCTT  TGACGTGAAA  AATTATTTGA  ACTATATCAT  TGATATAGTA  GGTTACTAC  CCAAAGGTAT  TCCTTATCAT  GATTGATATC  CAACTATTCA
168    Q  R  E    T  A  L  F      N  K  L       D  I  V       I  D  D        P  I  D  D       P  K  V  S        R  N  S  T        N  Y  R        L  I  S stuI
                  haeI
601   TGTAACACCT  CAGTCATTAC  ACAGGCCTGT  CCAAAGGTAT  CATTTGAGCC  AATTCCCATA  CATTTCTGTA  CCCCGGCTGG  TTTTGCGCTT  CTAAAGTGTA
      ACATTGTGGA  GTCAGTAATG  TGTCCGGACA  GGTTTCCATA  GTAAACATCG  TTAAGGGTAT  GTAAAGACAT  GGGGCCGACC  AAAACGCGAA  GATTTCACAT
201    C  N  T  S      V  I  T      Q  A  C       P  K  V  S      F  E  P         I  P  I        H  F  C  T         P  A  G       F  A  L       L  K  C  N esp3I                        scaI               bsp1407I              haeI
701   ATAATGAGAC  GTTCAATGGA  TCAGGACCAT  CAGTCATTAC  GCAAAAATGT  CAGCACAGTA  CTATGTACAC  ATGGAATTAG  GCCAGTAGTA  TCAACTCAAC
                                                                                                                       TGCTGTTAAA
```

TABLE 2-continued

```
 235  TATTACTCTG CAAGTTACCT AGTCCTGGTA CGTTTTTACA GTCGTGTCAT GATACATGTG TACCTTAATC CGGTCATCAT AGTTGAGTTG ACGACAATTT
      N   E   T    F   N   G    S   G   P   C    K   N   V    S   T   V    L   C   T   H    G   I   R    P   V   V    S   T   Q   L    L   L   N
                                             bstYI/xhoI                                                                            aseI/asnI/vspI
                                             bglII  apoI
 801  TGGCAGTCTA GCAGGAGAAG AGGTAGTAAT TAGATCTGAA AATTTCACGA ACAATGCTAA GAAAAATATA AAGAACCAGT GTACAGCTCA AAAAATTAAT
      ACCGTCAGAT CGTCCTCTTC TCCATCATTA ATCTAGACTT TTAAAGTGCT TGTTACGATT CTTTTTATAT TCTTGGTCA CATGTCGAGT TTTTTAATTA
      G   S   L    A   G   E    E   V   V   I    R   S   E    N   F   T   N    N   A   K    E   P   V    V   Q   L   K    K   I   N
               earI/ksp632I
                                                 bstI107I
                                                 accI scfI
 901  TGTACAAGAC CCAACAACAA TACAAGAAAA AGTATACCTA TAGGACCAGG ATCCTGTCC GCCACATAAT TCCTTTATAT AGGAAATATA AGACAAGCAC
      ACATGTTCTG GGTTGTTGTT ATGTTCTTTT TCATATGGAT TCCTGGTCC CGGTCGTAAT AGGAAATATA TCCTTTATATAT TCCTTTATAT TCTGTTCGTG
      C   T   R   P    N   N   N    T   R   K    S   I   P   I    G   P   G    R   A   F    Y   A   T   G    D   I   H    R   Q   A   H
      bsp1407I
                                                                                                                          eco81I
                                                                                                                          bsu36I/mstII/sauI
1001  ATTGTAACCT TAGTAGAACA GACTGAATA ACACTTTAAG ACAGATAGCT GAAAAATTAA CTTTTGTAAT ACATAATCT TTAATCACTC
      TAACATTGGA ATCATCTTGT CTGACCTTAT TGTGAAATTC TGTCTATCGA CTTTTTAATT GAAACATTA TGTTATTAGA AATTAGTAG
      C   N   L    S   R   T    D   W   N   N    T   L   R    Q   I   A    E   K   L   R    K   Q   F    T   I   I   F    N   H   S
           ppuMI
           eco0109I/draII
                                                                      apoI                                        scaI
1101  CTCAGGAGGG GACCCAGAAA TTGTAATGCA CAGTTTTAAT TGTAGAGGGG AATTTTTCTA CTGTGATACA AAACAAATT ACACAATTGT TTAACAGTAC TTGGAATGCA
      GAGTCCTCCC CTGGGTCTTT AACATTACGT GTCAAAATTA ACATCTCCCC TTAAAAAGAT GACACTATGT TTTGTTAA TGTGTTAACA AATTGTCATG AACCTTACGT
      S   G   G    D   P   E   I    V   M   H    S   F   N    C   R   G   E    F   F   Y    C   D   T    K   Q   F    N   S   T    W   N   A
                                                                                                              munI
                                                                                                              nspI
                                                                                                              nspHI
                                                                                                              aflIII
1201  AATAGCACAC CACTAAAGAG TCACACTCCC AGTGTAGGG ATGCAGAATA AAACAAATTG TAACACATGTG GCAGGAAGTA GGAAAAGCAA
      TTATCGTGTT GTGATTTCTC AGTGTGAGGG TCACATCCC TACGTCTTAT TTTGTTTAAC ATTTGTACAC CGTCCTTCAT CCTTTTCCTT
      N   N   T   E    R   N   S    T   L   P    C   R   I    K   Q   I   V    N   M   W    Q   E   V    G   K   A   M
                                          sspI                                                                                      bsaI
1301  TGTATGCCCC TCCCATCAGA GGACAAATTA GATGTTCATC AAATATTACA GGGTTGCTAT CCCAACGATA TAACAAATG AGCAACAGCA TGGAGGTAGT TTGAATGAGAC
      ACATACGGGG AGGGTAGTCT CCTGTTTAAT CTACAAGTAG TTTATAAATGT CCCAACGATA ATTGTGTCT ATTGTTTAAC TCGTTGTCGT ACCTCCATCA ACTTACTCTG
      Y   A   P    P   I   R    G   Q   I   R    C   S   S    N   I   T    G   L   L   L    T   R   D    S   N   S   M    N   E   T
                mamI
                bsaBI
             gsuI/bpmI                          munI
             eco57I  ecoNI
1401  CTTCAGACCT GGAGGAGAG ATATGAGGAG CAATTGGAA AGTGAATTAT ACAAATATAA AGTAGTAAAA TAGGAGTAGC ACCCACCAAG
      GAAGTCTGGA CCTCCTCCTC TATATCTCCC GTTAACCTTT TCACTTAATA TGTTTATATT TCATCATTTT ATCCTCATCG TGGGTGGTTC
      F   R   P    G   G   G   D    M   R   D    N   W   R    S   E   L   Y    K   Y   K    V   V   K    G   V   A    P   T   K
              earI/ksp632I                                                                      styI
1501  GCAATGAGAA GAGTGGTGCA GAGAGAAAAA GAGAGCAGAG TGTGTTCCTT ACAAGGAGAG ATTGAACCAT AAGCACTATG GCCGCAGCAG
      CGTTACTCTT CTCACCACGT CTCTCTTTTT CTCTCGTCTC ACACAAGGAA TGTTCCTCTC TAACTTGGTA TTCGTGATAC CGGCGTCGTC
      A   M   R   R    V   V   Q    R   E   K    A   V   G    V   F   L    G   F   L   G    A   A   G    S   T   M    G   A   A   S
      haeI                                                                                                alwNI
```

| | | | | | | | | |
|---|---|---|---|---|---|---|---|---|
| 1601 | CAATAACGCT<br>GTTATTGCGA<br>I I T L | GACGGTACAG<br>CTGCCATGTC<br>T V Q | GCCAGACTAT<br>CGGTCTGATA<br>A R L L | TATTGTCTGG<br>ATAACAGACC<br>L S G | TATAGTGCAA<br>ATATCACGTT<br>I V Q | CAGCAGAACA<br>GTCGTCTTGT<br>Q Q N N | ATTTGCTGAG<br>TAAACGACTC<br>L L R | GGCTATTGAG<br>CCGATAACTC<br>A I E | GGCCAACAGC<br>CCGGTTGTCG<br>A Q Q H | ATCTGTTGCA<br>TAGACAACGT<br>L L Q |
| 535 | | | | | | eco81I<br>bsu36I/mstII/sauI | | alwNI | | |
| 1701 | ACTCACAGTC<br>TGAGTGTCAG<br>L T V | TGGGCATCA<br>ACCCGTAGT<br>W G I K | AGCAGCTCCA<br>TCGTCGAGGT<br>Q L Q | GGCAAGAGTC<br>CCGTTCTCAG<br>A R V | CTGGCTGTGG<br>GACCGACACC<br>L A V E | AAAGATACCT<br>TTTCTATGGA<br>R Y L | AAGGGATCAA<br>TTCCCTAGTT<br>R D Q | CAGCTCCTGG<br>GTCGAGGACC<br>Q L L G | GGATTTGGGG<br>CCTAAACCCC<br>I W G | TTGCTCTGGA<br>AACGAGACCT<br>C S G |
| 568 | | | | | | | | | | |
| 1801 | AAACTCATTT<br>TTTGAGTAAA<br>K L I C | GCACCACCTC<br>CGTGGTGGAG<br>T T S | TGTGCCTTGG<br>ACACGGAACC<br>V P W | AATGCTAGTT<br>TTACGATCAA<br>N A S W | GGAGTAATAA<br>CCTCATTATT<br>S N K | ATCTCTAGAT<br>TAGAGATCTA<br>S L D | AAGATTTGGG<br>TTCTAAACCC<br>K I W D | ATAACATGAC<br>TATTGTACTG<br>N M T | CTGGATGGAG<br>GACCTACCTC<br>W M E | TGGGAAAGAG<br>ACCCTTTCTC<br>W E R E |
| 601 | | hindIII | styI bsmI | | xbaI | | | | | |
| 1901 | AAATTGAGAA<br>TTTAACTCTT<br>I E N | TTACACAAGC<br>AATGTGTTCG<br>Y T S | TTAATATACA<br>AATTATATGT<br>L I Y T | CCTTAATTGA<br>GGAATTAACT<br>L I E | AGAATCGCAG<br>TCTTAGCGTC<br>E S Q | TATATAAAAA<br>ATATATTTTT<br>Y I K I | AAAAGAATAA<br>TTTTCTTATT<br>K N K | ACAAGACTTA<br>TGTTCTGAAT<br>Q D L | TTGGAATTGG<br>AACCTTAACC<br>L E L D | ATCAATAGGC<br>TAGTTATCCG<br>Q Q A |
| 635 | | | | | sspI | | | | | |
| 2001 | AAGTTTGTGG<br>TTCAAACACC<br>S L W | AATTGGTTTA<br>TTAACCAAAT<br>N W F S | GCATAACAAA<br>CGTATTGTTT<br>I T K | ATGGCTGTGG<br>TACCGACACC<br>W L W | TATTCATAAT<br>ATAAGTATTA<br>F I M | CATTATCATT<br>GTAATAGTAA<br>L S F | GATAGTTGGA<br>CTATCAACCT<br>I V G | GGCTTGGTAG<br>CCGAACCATC<br>G L V G | GTTTAAGAAT<br>CAAATTCTTA<br>L R I | AGTTTTTGCT<br>TCAAAAACGA<br>V F A |
| 668 | scfI | | | bstYI/xhoII | | | aval | ppuMI<br>eco0109I/draII | | |
| 2101 | GTACTTTCTA<br>CATGAAAGAT<br>V L S I | TAGTGAATAG<br>ATCACTTATC<br>V N R | AGTTAGGCAG<br>TCAATCCGTC<br>V R Q | GGGTACTCAC<br>CCCATGAGTG<br>G Y S P | CATTATCATT<br>GTAATAGTAA<br>L S F | TCAGACCCGC<br>AGTCTGGGCG<br>Q T R | CTCCCAGCCC<br>GAGGGTCGGG<br>L P A P | CGAGGGGACC<br>GCTCCCCTGG<br>R G P | CGACAGGCCC<br>GCTGTCCGGG<br>D R P | AAAGGAATCG<br>TTTCCTTAGC<br>K G I E |
| 701 | | | | | | | | | | eco57I<br>earI/ksp632I |
| 2201 | AAGAGAAGG<br>TTCTTCTTCC<br>E E G | TGGAGAGCAA<br>ACCTCTCGTT<br>G E Q | GACAGGGACA<br>CTGTCCCTGT<br>D R D R | GATCCATTCG<br>CTAGGTAAGC<br>S I R | CTTAGTGGAT<br>GAATCACCTA<br>L V D | GGATTCTTAG<br>CCTAAGAATC<br>G F L A | CACTTATCTG<br>GTGAATAGAC<br>L I W | GGACCATCTA<br>CCTGGTAGAT<br>D D L | CGGAGCCTGT<br>GCCTCGGACA<br>R S L C | GCCTCTTCAG<br>CGGAGAAGTC<br>L F S |
| 735 | | | | | | | | | sspI | scfI |

TABLE 2-continued

| | | | | | | | | | |
|---|---|---|---|---|---|---|---|---|---|
| 2301 | CTACCACCGC | TTGAGAGACT | TACTCTTGAT | TGCAACGAGG | ATTGTGGAAC | TTCTGGGACG | CAGGGGGTGG | GAAGCCCTCA | AATATTGGTG | GAATCTCCTA |
| | GATGGTGGCG | AACTCTCTGA | ATGAGAACTA | ACGTTGCTCC | TAACACCTTG | AAGACCCTGC | GTCCCCCACC | CTTCGGGAGT | TTATAACCAC | CTTAGAGGAT |
| 768 | Y H R | L R D L | L L I | A T R | I V E L | L G R | R G W | E A L K | Y W W | N L L |
| | | | | | | | alwNI | | xbaI | |
| 2401 | CAGTATTGGA | TTCAGGAACT | AAAGAATAGT | GCTGTTAGCT | TGCTTAATGT | CACAGCCATA | GCAGTAGCTG | AGGGACAGA | TAGGGTTCTA | GAAGCATTGC |
| | GTCATAACCT | AAGTCCTTGA | TTTCTTATCA | CGACAATCGA | ACGAATTACA | GTGTCGGTAT | CGTCATCGAC | TCCCCTGTCT | ATCCCAAGAT | CTTCGTAACG |
| 801 | Q Y W I | Q E L | K N S | A V S L | L N V | T A I | A V A E | G T D | R V L | E A L Q |
| 2501 | AAAGAGCTTA | TAGAGCTATT | CTCCACATAC | CTACAAGAAT | AAGACAAGGC | TTGGAAAGGG | CTTTGCTATA | A | | |
| | TTTCTCGAAT | ATCTCGATAA | GAGGTGTATG | GATGTTCTTA | TTCTGTTCCG | AACCTTTCCC | CAAACGATAT | T | | |
| 835 | R A Y | R A I | L H I P | T R I | R Q G | L E R A | L L Q | | | |

>length: 2571

Table 3 illustrates the amino acid sequences for the $GNE_8$ and different $GNE_{16}$ gp120 proteins. The regions of the sequences having identical amino acid sequences are enclosed in boxes sequence gp160.SF.16.7 is a stop codon.

TABLE 3

| | | |
|---|---|---|
| gp160.8.24 | 1 | M I V K G I R K N C Q H L W R W G T M L L G M L M I C S A A E K L W V T V Y Y G V P V W K E A T T T |
| gp160.SF.16.2 | 1 | M R V K G I R R N Y Q H L W R W G T M L L G I L M I C S A A G K L W V T V Y Y G V P V W K E T T T T |
| gp160.SF.16.7 | 1 | M R V K R I R R N Y Q H L W K W G T M L L G M L M I C S A A G K L W V T V Y Y G V P V W K E T T T T |
| gp160.8.24 | 51 | L F C A S D A K A Y D T E V H N V W A T H A C V P T D P N P Q E I G L E N V T E N F N M W K N N M V |
| gp160.SF.16.2 | 51 | L F C A S D A K A Y D T E I H N V W A T H A C V P T D P N P Q E V V L E N V T E N F N M W K N N M V |
| gp160.SF.16.7 | 51 | L F C A S D A K A Y D T E I H N V W A T H A C V P T D P N P Q E V V L E N V T E N F N M W K N N M V |
| gp160.8.24 | 101 | E Q M H E D I I S L W D Q S L K P C V K L T P L C V T L N C T D L K N A T N T T S S S W G K M E R G |
| gp160.SF.16.2 | 101 | E Q M H E D I I S L W D Q S L K P C V K L T P L C V T L N C T D A G N T T N T N S S S R E K L E K G |
| gp160.SF.16.7 | 101 | E Q M H E D I I S L W D Q S L K P C V K L T P L C V T L N C T D A G N T T N T N S S S G E K L E K G |
| gp160.8.24 | 151 | E I K N C S F N V T T S I R D K M K N E Y A L F Y K L D V V P I D N D N . . . . . . . T S Y R L I S |
| gp160.SF.16.2 | 151 | E I K N C S F N I T T S V R D K M Q K E T A L F N K L D I V P I D D D D R N S T R N S T N Y R L I S |
| gp160.SF.16.7 | 151 | E I K N C S F N I T T S M R D K M Q R E T A L F N K L D I V P I D D D D R N S T R N S T N Y R L I S |
| gp160.8.24 | 194 | C N T S V I T Q A C P K V S F E P I P I H Y C A P A G F A I L K C R D K K F N G T G P C T N V S T V |
| gp160.SF.16.2 | 201 | C N T S V I T Q A C P K V S F E P I P I H F C T P A G F A L L K C N N K T F N G S G P C K N V S T V |
| gp160.SF.16.7 | 201 | C N T S V I T Q A C P K V S F E P I P I H F C T P A G F A L L K C N N E T F N G S G P C K N V S T V |
| gp160.8.24 | 244 | Q C T H G I R P V V S T Q L L L N G S L A E E E V V I R S A N F S D N A K T I I V Q L N E S V E I N |
| gp160.SF.16.2 | 251 | Q C T H G I R P V V S T Q L L L N G S L A E G E V V I R S E N F T N N A K T I I V Q L T E P V K I N |
| gp160.SF.16.7 | 251 | L C T H G I R P V V S T Q L L L N G S L A G E E V V I R S E N F T N N A K T I I V Q L K E P V K I N |
| gp160.8.24 | 294 | C T R P N N N T R R S I H I G P G R A F Y A T G E I I G D I R Q A H C N L S S T K W N N T L K Q I V |
| gp160.SF.16.2 | 301 | C T R P N N N T R K S I P I G P G R A F Y A T G D I I G N I R Q A H C N L S R T D W N N T L G Q I V |
| gp160.SF.16.7 | 301 | C T R P N N N T R K S I P I G P G R A F Y A T G D I I G N I R Q A H C N L S R T D W N N T L R Q I A |
| gp160.8.24 | 344 | T K L R E H F . N K T I V F N H S S G G D P E I V M H S F N C G G E F F Y C N T T P L F N S T W N Y |
| gp160.SF.16.2 | 351 | E K L R E Q F G N K T I I F N H S S G G D P E I V M H S F N C R G E F F Y C N T T Q L F D S T W D N |
| gp160.SF.16.7 | 351 | E K L R K Q F G N K T I I F N H S S G G D P E I V M H S F N C R G E F F Y C D T T Q L F N S T W N A |
| gp160.8.24 | 393 | T Y T W N N T E G S N D T G R N I T L Q C R I K Q I I N M W Q E V G K A M Y A P P I R G Q I R C S S |
| gp160.SF.16.2 | 401 | T K V . . S N G T S T E E N S T I T L P C R I K Q I V N M W Q E V G K A M Y A P P I R G Q I R C S S |
| gp160.SF.16.7 | 401 | N N T . . E R . N S T K E N S T I T L P C R I K Q I V N M W Q E V G K A M Y A P P I R G Q I R C S S |
| gp160.8.24 | 443 | N I T G L L L T R D G G . N N S E T E I F R P G G G D M R D N W R S E L Y K Y K V V K I E P L G V A |
| gp160.SF.16.2 | 449 | N I T G L L L T R D G G S N N S M N E T F R P G G G D M R D N W R S E L Y K Y K V V K I E P L G V A |
| gp160.SF.16.7 | 448 | N I T G L L L T R D G G S S N S M N E T F R P G G G D M R D N W R S E L Y K Y K V V K I E P L G V A |
| gp160.8.24 | 492 | P T K A K R R V M Q R E K R A . G I G A V F L G F L G A A G S T M G A A S V T L T V Q A R L L L S G |
| gp160.SF.16.2 | 499 | P T K A K R R V V Q R E K R A V G I G A V F L G F L G A A G S T M G A A S I T L T V Q A R L L L S G |
| gp160.SF.16.7 | 498 | P T K A M R R V V Q R E K R A V G I G A V F L G F L G A A G S T M G A A S I T L T V Q A R L L L S G |

TABLE 3-continued

| | | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| gp160.8.24 | 542 | I | V | Q | N | L | L | R | A | I | E | A | Q | H | L | L | Q | L | T | V | W | G | I | K | Q | L | Q | A | R | V | L | A | V | E | R | Y | L | K | D | Q | Q | L | L | G | I | W | G |
| gp160.SF.16.2 | 549 | I | V | Q | N | L | L | R | A | I | E | A | Q | H | L | L | Q | L | T | V | W | G | I | K | Q | L | Q | A | R | V | L | A | V | E | R | Y | L | R | D | Q | Q | L | L | G | I | W | G |
| gp160.SF.16.7 | 548 | I | V | Q | N | L | L | R | A | I | E | A | Q | H | L | L | Q | L | T | V | W | G | I | K | Q | L | Q | A | R | V | L | A | V | E | R | Y | L | R | D | Q | Q | L | L | G | I | W | G |
| gp160.8.24 | 592 | C | S | G | K | L | I | C | T | T | S | V | P | W | N | A | S | W | S | N | K | S | L | D | K | I | W | D | N | M | T | W | M | E | W | E | R | E | I | D | N | Y | T | S | L | I | H | E |
| gp160.SF.16.2 | 599 | C | S | G | K | L | I | C | T | T | T | V | P | W | N | A | S | W | S | N | K | S | L | D | K | I | W | D | N | M | T | W | M | E | W | E | R | E | I | E | N | Y | T | S | L | I | H | E |
| gp160.SF.16.7 | 598 | C | S | G | K | L | I | C | T | T | T | V | P | W | N | A | S | W | S | N | K | S | L | D | K | I | W | D | N | M | T | W | M | E | W | E | R | E | I | E | N | Y | T | S | L | I | H | E |
| gp160.8.24 | 642 | E | S | Q | N | N | E | K | E | L | L | E | L | D | K | W | A | S | L | W | N | W | F | D | I | T | K | W | L | W | Y | I | K | I | F | I | M | I | V | G | G | L | V | G | L | R | I |
| gp160.SF.16.2 | 649 | E | S | Q | N | N | E | K | N | L | L | E | L | D | Q | | | A | S | L | W | N | W | F | D | I | T | K | W | L | W | Y | I | K | I | F | I | M | I | V | G | G | L | V | G | L | R | I |
| gp160.SF.16.7 | 648 | E | S | Q | N | N | E | K | N | L | L | E | L | D | Q | | | A | S | L | W | N | W | F | D | I | T | K | W | L | W | Y | I | K | I | F | I | M | I | V | G | G | L | V | G | L | R | I |
| gp160.8.24 | 692 | V | F | T | V | L | S | I | V | N | R | V | R | K | G | Y | S | P | L | S | F | Q | T | H | L | P | A | P | R | G | P | D | R | P | E | G | I | E | E | G | G | E | R | D | R | D | R |
| gp160.SF.16.2 | 699 | V | F | A | V | L | S | I | V | N | R | V | R | Q | G | Y | S | P | L | S | F | Q | T | R | L | P | A | P | R | G | P | D | R | P | E | G | I | E | E | G | G | E | R | D | R | S | R |
| gp160.SF.16.7 | 698 | V | F | A | V | L | S | I | V | N | R | V | R | Q | G | Y | S | P | L | S | F | Q | T | R | L | P | A | P | R | G | P | D | R | P | E | G | I | E | E | G | G | E | R | D | R | S | R |
| gp160.8.24 | 742 | L | V | D | G | F | L | A | I | I | W | V | D | L | R | S | L | C | L | F | S | Y | H | R | L | R | D | L | L | L | I | V | E | L | L | G | R | R | G | W | E | A | L | K | Y | W | W |
| gp160.SF.16.2 | 749 | L | V | D | G | F | L | A | L | I | H | H | D | L | R | S | L | C | L | F | S | Y | H | R | L | R | D | L | L | L | I | V | H | H | V | L | L | G | R | R | G | W | E | A | L | K | Y | W |
| gp160.SF.16.7 | 748 | L | V | D | G | F | L | A | L | I | H | H | D | L | R | S | L | C | L | F | S | Y | H | R | L | R | D | L | L | L | I | V | H | H | V | L | L | G | R | R | G | W | E | A | L | K | Y | W |
| gp160.8.24 | 792 | N | L | L | Q | Y | W | I | Q | E | L | K | N | S | A | V | S | L | L | N | A | T | A | I | H | A | V | A | E | G | T | D | R | V | I | E | V | V | Q | R | A | Y | R | A | I | R | H | I |
| gp160.SF.16.2 | 799 | N | L | L | Q | Y | W | I | H | Q | E | L | K | N | S | S | L | L | N | A | T | A | I | A | V | A | E | G | T | D | R | V | I | E | V | L | Q | R | A | Y | R | A | I | H | P | T | R | I |
| gp160.SF.16.7 | 798 | N | L | L | Q | Y | W | I | H | Q | E | L | K | N | S | S | L | L | N | V | T | A | I | A | V | A | E | G | T | D | R | V | I | E | V | L | Q | R | A | Y | R | A | I | H | P | T | R | I |
| gp160.8.24 | 842 | R | Q | G | L | E | R | A | L | L | | | | | | | | | | | | | | | | | | | | | | | | | | | | | | | | | | | | | | | |
| gp160.SF.16.2 | 849 | R | Q | G | L | E | R | A | L | L | | | | | | | | | | | | | | | | | | | | | | | | | | | | | | | | | | | | | | | |
| gp160.SF.16.7 | 848 | R | Q | G | L | E | R | A | L | L | | | | | | | | | | | | | | | | | | | | | | | | | | | | | | | | | | | | | | | |

Nucleic acid sequences e coding gp120 from GNE$_8$ and GNE$_{16}$ capable of expressing gp120 can be prepared by conventional means. The nucleotide sequence can be synthesized. Alternatively, another HIV nucleic acid sequence encoding gp120 can be used as a backbone and altered at any differing residues by site directed mutagenesis as described in detail in Example 1.

In a preferred embodiment, the nucleotide sequence is present in an expression construct containing DNA encoding gp120 under the transcriptional and translational control of a promoter for expression of the encoded protein. The promoter can be a eukaryotic promoter for expression in a mammalian cell. In cases where one wishes to expand the promoter or produce gp120 in a prokaryotic host, the promoter can be a prokaryotic promoter. Usually a strong promoter is employed to provide high level transcription and expression.

The expression construct can be part of a vector capable of stable extrachromosomal maintenance in an appropriate cellular host or may be integrated into host genomes. Normally, markers are provided with the expression construct which allow for selection of a host containing the construct. The marker can be on the same or a different DNA molecule, desirably, the same DNA molecule.

The expression construct can be joined to a replication system recognized by the intended host cell. Various replication systems include viral replication systems such as retroviruses, simian virus, bovine papilloma virus, or the like. In addition, the construct may be joined to an amplifiable gene, e.g. DHFR gene, so that multiple copies of the gp120 DNA can be made. Introduction of the construct into the host will vary depending on the construct and can be achieved by any convenient means. A wide variety of prokaryotic and eukaryotic hosts can be employed for expression of the proteins.

Preferably, the gp120 is expressed in mammalian cells that provide the same glycosylation and disulfide bonds as in native gp120. Expression of gp120 and fragments of gp120 in mammalian cells as fusion proteins incorporating N-terminal sequences of Herpes Simplex Virus Type 1 (HSV-1) glycoprotein D (gD-1) is 10 described in Lasky, L. A. et al., 1986 (Neutralization of the AIDS retrovirus by antibodies to a recombinant envelope glycoprotein) Science 233: 209–212 and Haffar, O. K. et al., 1991 (The cytoplasmic tail of HIV-1 gp160 contains regions that associate with cellular membranes.) Virol. 180:439–441, respectively. A preferred method for expressing gp120 is described in Example 3. In the example, a heterologous signal sequence was used for convenient expression of the protein. However, the protein can also be expressed using the native signal sequence.

An isolated, purified $GNE_8$-gp120 and $GNE_{16}$-gp120 having the amino acid sequence illustrated in Tables 1–3 can be produced by conventional methods. For example, the proteins can be chemically synthesized. In a preferred embodiment, the proteins are expressed in mammalian cells using an expression construct of this invention. The expressed proteins can be purified by conventional means. A preferred purification procedure is described in Example 3.

gp120 Fragments

The present invention also provides gp120 fragments that are suitable for use in inducing antibodies for use in serotyping or in a vaccine formulation. A truncated gp120 sequence as used herein is a fragment of gp120 that is free from a portion of the intact gp120 sequence beginning at either the amino or carboxy terminus of gp120. A truncated gp120 sequence of this inventior is free from the C5 domain. The C5 domain of gp120 is a major immunogenic site of the molecule. However, antibodies to the region do not neutralize virus. Therefore, elimination of this portion of gp120 from immunogens used to induce antibodies for serotyping is advantageous.

In another embodiment, the truncated gp120 sequence is additionally free from the carboxy terminus region through about amino acid residue 453 of the gp120 V5 domain. The portion of the V5 domain remaining in the sequence provides a convenient restriction site for preparation of expression constructs. However, a truncated gp120 sequence that is free from the entire gp120 V5 domain is also suitable for use in inducing antibodies.

In addition, portions of the amino terminus of gp120 can also be eliminated from the truncated gp120 sequence. The truncated gp120 sequence can additionally be free from the gp120 signal sequence. The truncated gp120 sequence can be free from the amino terminus through amino acid residue 111 of the gp120 C1 domain, eliminating most of the C1 domain but preserving a convenient restriction site. However, the portion of the C1 domain through the cysteine residue that forms a disulfide bond can additionally be removed, so that the truncated gp120 sequence is free from the amino terminus through amino acid residue 117 of the gp120 C1 domain. Alternatively, the truncated gp120 sequence can be free from the amino terminus of gp120 through residue 111 of the C1 domain, preserving the V2 disulfide bond. In a preferred embodiment, the truncated gp120 sequence is free from the amino terminus of gp120 through residue Ill of the C1 domain and residue 453 through the carboxy terminus of gp120.

The truncated gp120 sequences can be produced by recombinant engineering, as described previously. Conveniently, DNA encoding the truncated gp120 sequence is joined to a heterologous DNA sequence encoding a signal sequence.

Serotypinc Method

The present invention also provides an improved serotyping method for HIV strains. The method comprises determining the serotypes of the V2, V3, and C4 domains of gp120.

HIV isolates can be serotyped by conventional immunoassay methods employing antibodies to the neutralizing epitopes in the V2, V3, and C4 domains for various strains of HIV. Preparation of the antibodies is described hereinbefore. The antibody affinity required for serotyping HIV using a particular immunoassay method does not differ from that required to detect other polypeptide analytes. The antibody composition can be polyclonal or monoclonal, preferably monoclonal.

A number of different types of immunoassay are well known using a variety of protocols and labels. The assay conditions and reagents may be any of a variety found in the prior art. The assay may be heterogeneous or homogeneous. Conveniently, an HIV isolate is adsorbed to a solid phase and detected with antibody specific for one strain of neutralizing epitope for each neutralizing epitope in the V2, V3, and C4 domain. Alternatively, supernatant or lysate from the cultured isolate which contains gp120 can be adsorbed to the solid phase. The virus or gp120 can be adsorbed by many well known nonspecific binding methods. Alternatively, an anti-gp120 antibody, preferably directed to the carboxy terminus of gp120 can be used to affix gp120 to the solid phase. A gp120 capture antibody and sandwich ELISA assay for gp120 neutralizing epitopes is described by Moore, *AIDS Res. Hum. Retroviruses* 9:209–219 (1993). Binding between the antibodies and sample can be determined in a number of ways. Complex formation can be determined by use of soluble antibodies specific for the anti-gp120 antibody. The soluble antibodies can be labeled directly or can be detected using labeled second antibodies specific for the species of the soluble antibodies. Various labels include radionuclides, enzymes, fluorescers, colloidal metals or the like. Conveniently, the anti-gp120 antibodies will be labeled directly, conveniently with an enzyme.

Alternatively, other methods for determining the neutralizing epitopes can be used. For example, fluorescent-labeled antibodies for a neutralizing epitope can be combined with cells infected by the strain of HIV to be serotyped and analyzed by fluorescence activated cell sorting.

The serotype of the HIV isolate includes the strain of the neutralizing epitopes for the V2, V3, and C4 domains.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLE 1

Identification of C4 Neutralizing Epitopes

The following reagents and methods were used in the studies described herein.

gp120 sequences and nomenclature. Amino acid residues are designated using the standard single letter code. The location of amino acids within the gp120 protein is specified using the initiator methionine residue as position 1. The designation LAI is used to describe the virus isolate from which the HIV-$1_{BH10}$, HIV-$1_{IIIB}$, HIV-$1_{BRU}$, HIV-$1_{HXB2}$, HIV-$1_{HXB3}$ and HIV-$1_{HXB10}$ substrains (molecular clones) of HIV-1 were obtained. The sequence of gp120 from IIIB substrain of HIV-$1_{LAI}$ is that determined by Muesing et al. (30).

The sequence of gp120 from MN strain of HIV-1 is given with reference to the MNgp120 clone ($MN_{GNE}$). The sequence of this clone differs by approximately 2% from that of the $MN_{1984}$ clone described by Gurgo et al. (13). The sequences of gp120 from the NY-5, JRcsf, Z6, Z321, and HXB2 strains of HIV-1 are those listed by Myers et al. (32) except where noted otherwise. The sequence of the Thai isolate A244 is that provided by McCutchan et al. (24). The variable (V) domains and conserved (C) domains of gp120 are specified according to the nomenclature of Modrow et al. (28).

Monoclonal antibody production and screening assays. Hybridomas producing monoclonal antibodies to MN-rgp120 (recombinantly produced gp120 from the MN strain of HIV) (3) were prepared and screened for CD4 blocking activity as described previously (7, 33). The binding of monoclonal antibodies to MN-rgp120 and to rgp120s from the IIIB, NY-5, Z6, Z321, JRcsf, and A244 strains of HIV-1 was assessed by enzyme linked immunoadsorbant assays (ELISA) as described previously (33).

Virus binding and neutralization assays. The ability of monoclonal antibodies to neutralize HIV-1 infectivity in vitro was assessed in a colorimetric MT-2 cell cytotoxicity assay similar to that described previously (35). MT-2 cells and H9/HTLV-$III_{MN}$ cells were obtained through the AIDS Research and Reference Reagent Program, Division of AIDS, NIAID, NIH: contributed by Drs. Douglas Richman and Robert Gallo, respectively. Briefly, serial dilutions of antibody or serum were prepared in 50 $\mu$l volumes of complete and then 50 $\mu$l of a prediluted HIV-1 stock was added to each well. After incubation for 1 hr at 4° C., 100 $\mu$l of a $4\times10^5$ MT-2 cell/ml suspension was added. After incubation of the plates for 5 days at 37° C. in 5%. $CO_2$, viable cells were measured using metabolic conversion of the formazan MTT dye. Each well received 20 $\mu$l of a 5 mg/ml MTT solution in PBS.

After a 4 hr incubation at 37° C., the dye precipitate was dissolved by removing 100 $\mu$l of the cell supernatant, adding 130 $\mu$l of 10% Triton X-100 in acid isopropanol, then pipeting until the precipitate was dissolved. The optical density of the wells was determined at 540 nm. The percentage inhibition was calculated using the formula:

$$\frac{1-(\text{virus control}-\text{experimental})}{(\text{virus control}-\text{medium control})}$$

Cell surface staining of HIV-1 infected cells with monoclonal antibodies. H9 cells ($2\times10^5$) chronically injected with the IIIB, HXB2, HXB3, and HX10 substrains of HIV-$1_{LAI}$ or with HIV-$1_{MN}$ were incubated for 30 min at room temperature with monoclonal antibodies (10 $\mu$g per ml) in 100 $\mu$l of RPMI 1640 cell culture media containing 1% FCS. Cells were washed and then incubated with 20 $\mu$g per ml of fluorescein-conjugated, affinity-purified, goat antibody to mouse IgG $(Fab')_2$ (Cappel, West Chester, Pa.) for 30 min. Cells were washed, fixed with 1% paraformaldehyde and the bound antibody was quantitated by flow cytometry using a FACSCAN (Becton-Dickenson, Fullerton, Calif.).

Fluorescence data was expressed as percentage of fluorescent cells compared to the fluorescence obtained with the second antibody alone. Fluorescence was measured as the mean intensity of the cells expressed as mean channel number plotted on a log scale.

Fragmentation of the MN-rgp120 gene. Fragments of the MN-rgp120 gene were generated using the polymerase chain reaction (PCR) (17). Briefly, forward 30-mer oligonucleotide DNA primers incorporating a Xho 1 site, and reverse 36-mer oligonucleotide DNA primers containing a stop codon followed by a Xba 1 site were synthesized and used for the polymerase chain reactions. Thirty cycles of the PCR reaction were performed using 0.3 $\mu$g of a plasmid containing the gene for gp120 from the MN strain of HIV-1 (pRKMN. D533) and 0.04 nM of a designated primers. The PCR reaction buffer consisted of 0.1 M Tris buffer (pH 8.4), 50 mM KCl, 0.2 mM 4dNTP (Pharmacia, Piscataway, N.J.), 0.15 M $MgCl_2$ and 0.5 Unit of Taq Polymerase (Perkin-Elmer Cetus, Norwalk, Conn.) and a typical PCR cycle consisted of a 60 second denaturation step at 94° C., followed by a 45 second annealing step at 55° C., and then an extension step at 72° C. for 45 seconds.

Following the PCR amplification, the PCR products were purified by phenol and chloroform extraction, and then ethanol precipitated. The purified products were then digested with the restriction endonucleases Xho1 and Xba1. The resulting PCR products were gel purified using 1% agarose (SEAKEM, FMC Bioproducts, Rockland, Me.) or 5% polyacrylamide gel electrophoresis (PAGE) and then isolated by electroelution.

Site directed mutagenesis of the MN-rgp120 C4 domain. A recombinant PCR technique (15) was utilized to introduce single amino acid substitutions at selected sites into a 600 bp Bgl II fragment of MN-rgp120 that contained the C4 domain. This method entailed the PCR amplification of overlapping regions of the C4 domain of gp120 using primers that incorporated the desired nucleotide changes. The resultant PCR products were then annealed and PCR amplified to generate the final product. For these reactions 18-mer "outside" primers encoding the wild type sequence (Bgl II sites) were amplified with 36-mer "inside" primers that contained the alanine or glutamic acid residue changes. The first PCR reaction included 1× of the Vent polymerase buffer (New England Biolabs, Beverly, Mass.), 0.2 mM of 4dNTP (Pharmacia, Piscataway, N.J.), 0.04 nM of each synthetic oligonucleotide, 0.3 µg of linearized plasmid, pRKMN.D533, which contained the MN-rgp120 gene. Thirty PCR cycles were performed consisting of the following sequence of steps: 45 seconds of denaturation at 94° C., 45 second of annealing at 55° C. and 45 seconds of extension at 72° C. Following PCR amplification, the product pairs were gel purified using a 1% solution of low melt agarose (SeaPlaque, FMC Bioproducts, Rockland, Me.).

The agarose containing PCR product was melted at 65° C. and combined with the PCR product of the overlapping pair and equilibrated to 37° C. Added to this (20 µl) was 10 µl of 10× Vent Polymerase buffer, 10 µl of 2 mM 4dNTP, 0.04 nM each of the "outside" wild type 18 mer oligonucleotides, 57 µl of $H_2O$ and 1 unit of Vent Polymerase. Thirty PCR cycles were performed as previously above.

The resulting PCR products were purified and digested with the Bgl II endonuclease. The digested PCR product was then ligated into the mammalian cell expression vector pRKMN.D533, which had been digested with Bgl II allowing for the removal of a 600 bp fragment. Colonies containing the correct insertion were identified and Sequenase 2.0 supercoil sequencing was employed to check for fidelity and the incorporation of the desired mutation.

Expression of gp120 fragments in mammalian cells. Fragments of the MN and IIIB gp120 were expressed in mammalian cells as fusion proteins incorporating N-terminal sequences of Herpes Simplex Virus Type 1 (HSV-1) glycoprotein D (gD-1) as described previously (14, 22). Briefly, isolated DNA fragments generated by the PCR reaction were ligated into a plasmid (pRK.gD-1) designed to fuse the gp120 fragments, in frame, to the 5' sequences of the glycoprotein D (gD) gene of Type 1 Herpes Simplex Virus (gD-1)and the 3' end to translational stop codons. The fragment of the gD-1 gene encoded the signal sequence and 25 amino acids of the mature form of HSV-1 protein. To allow for expression in mammalian cells, chimeric genes fragments were cloned into the pRK5 expression plasmid (8) that contained a polylinker with cloning sites and translational stop codons located between a cytomegalovirus promotor and a simian virus 40 virus polyadenylation site.

The resulting plasmids were transfected into the 293s embryonic human kidney cell line (12) using a calcium phosphate technique (11). Growth conditioned cell culture media was collected 48 hr after transfection, and the soluble proteins were detected by ELISA or by specific radioimmunoprecipitation where metabolically labeled proteins from cell culture supernatants were resolved by sodium dodecyl sulfate polyacrylamide gel electrophoresis (PAGE) and visualized by autoradiography as described previously Radioimmunoprecipitation of MN-rgp120 mutants.

Plasmids directing the expression of the MN-rgp120 C4 domain mutants were transfected into 293s cells as described above. Twenty four hours following the transfection, the cells were metabolically labeled with [$^{35}$S]-labeled methionine or cysteine as described previously (1). The labeled cell culture supernatants were then harvested and 0.5 ml aliquots were reacted with 1–5 µg of the monoclonal antibody or with 2 µl of the polyclonal rabbit antisera to MN-rgp120 and immunoprecipitated with Pansorbin (CalBiochem, La Jolla, Calif.) as described previously (1). The resulting Pansorbin complex was pelleted by centrifugation, washed twice with a solution containing PBS, 1% NP-40 and 0.05% SDS and then boiled in a PAGE sample buffer containing 1% 2-mercaptoethanol. The processed samples were the analyzed by SDS-PAGE and visualized by autoradiography (1, 18).

Assays to measure the binding of monoclonal antibodies to mutagenized MN-rgp120 polypeptides. An ELISA was developed to screen for reactivity of MN-rgp120 fragments and mutant proteins with various monoclonal antibodies. In this assay, 96 well microtiter dishes (Maxisorp, Nunc, Roskilde, Denmark) were coated overnight with mouse monoclonal antibody (5B6) to gD-1, at a concentration of 2.0 µg/ml in phosphate buffered saline (PBS). The plates were blocked in a PBS solution containing 0.5% bovine serum albumin (PBSA) and then incubated with growth conditioned cell culture medium from transfected cells expressing the recombinant gp120 variants for 2 hr at room temperature. The plates were washed three times in PBS containing 0.05% Tween 20 and then incubated with the purified, HRPO-conjugated monoclonal antibodies. Following a 1 hr incubation, the plates were washed three times and developed with the calorimetric substrate, o-phenylenediamine (sigma, St. Louis, Mo.).

The optical densities in each well were then read in a microtiter plate reading spectrophotometer at 492 nm. Each cell culture supernatant containing fragments or mutated rgp120s was normalized for expression based on the titering of its reactivity to the V3 binding monoclonal antibody 1034 or to a rabbit polyclonal antisera to MN-rgp120. Data from these experiments were expressed as a ratio of the optical densities obtained with the CD4 blocking monoclonal antibodies binding to the fragments or MN-rgp120 mutants compared with the full length wild type rgp120s.

To normalize for different concentrations of MN-rgp120-derived protein in the cell culture supernatants, the binding of the CD4 blocking monoclonal antibodies to each preparation was compared to that of an HRPO-conjugated monoclonal antibody to the V3 domain of MN-rgp120 (1034). Data from these experiments were expressed as a ratio of the optical densities obtained with the CD4 blocking monoclonal antibodies to the HRPO conjugated V3 reactive monoclonal antibody.

CD4 binding assays. The ability of monoclonal antibodies to inhibit the binding of KN-rgp120 to recombinant soluble CD4 (rsCD4) was determined in a solid phase radioimmunoassay similar to that described previously (33). The effect of single amino acid substitutions on the binding of MN-rgp120 mutants to CD4 was determined in a co-immunoprecipitation assay similar to that described previously (21). Briefly, 293 cells were metabolically labeled with $^{35}$S-methionine 24 hr after transfection with plasmids expressing MN-rgp120 variants. Growth conditioned cell culture medium (0.5 ml) was then incubated with 5.0 μg of recombinant sCD4 for 90 minutes at room temperature. Following this incubation, 5.0 μg of an anti-CD4 monoclonal antibody (465), known to bind to an epitope remote from the gp120 binding site, was added and allowed to incubate another 90 minutes at room temperature.

The gp120-CD4-antibody complexes were precipitated with Pansorbin that had been washed with PBS, preabsorbed with 0.1% bovine serum albumin and then bound with 50 μg of an affinity purified rabbit anti-mouse IgG (Cappel, West Chester, Pa.). The pellet was washed twice with PBS 1% NP-40, 0.05% SDS, and then boiled in beta mercaptoethanol containing SDS-PAGE sample buffer. The immunoprecipitation products were resolved by SDS PAGE and visualized by autoradiography as described previously (1, 21).

Antibody affinity measurements. Anti-gp120 antibodies were iodinated with Na$^{125}$I with iodogen· (Pierce, Rockford, Ill.). Briefly, 50 μg of antibody in PBS was placed in 1.5 ml polypropylene microcentrifuge tubes coated with 50 μg of Iodogen. Two millicuries of carrier free Na [$^{125}$I] was added. After 15 min., free $^{125}$I was separated from the labeled protein by chromatography on a PD-10 column (Pierce, Rockford, Ill.) pre-equilibrated in PBS containing 0.5% gelatin. Antibody concentrations following iodination were determined by ELISA to calculate specific activities.

For binding assays, 96-well microtiter plates were coated with 100 μl/well of a 10 μg/ml solution of MN-rgp120 or IIIBrgp120 in 0.1 M bicarbonate buffer, pH 9.6 and incubated for 2 hr at room temperature or overnight at 4° C. To prevent non-specific binding, plates were blocked for 1–2 hr at room temperature with 200 μl/well of a gelatin solution consisting of PBS containing 0.5% (wt/vol) gelatin and 0.02% sodium azide. Unlabeled anti-gp120 monoclonal antibody (0 to 400 nM) was titrated (in duplicate) in situ and radiolabeled antibody was added to each well at a concentration of 0.5 nM.

After a 1–2 hr incubation at room temperature, the plate was washed 10x with the PBS/0.5% gelatin/0.02% azide buffer to remove free antibody. The antibody-gp120 complexes were solubilized with 0.1 N NaOH/0.1% SDS solution and counted in a gamma counter. The data were analyzed by the method of Scatchard (40) using the Ligand analytical software program (31). $K_d$ values reported represent the means of four independent determinations.

RESULTS

Characterization of monoclonal antibodies to MN-rgp120 that block CD4 binding. Monoclonal antibodies prepared from mice immunized with MN-rgp120 (3, 33), were screened for the ability to bind to MN-rgp120 coated microtiter dishes by ELISA as described previously (33). Of the thirty five clones obtained, seven were identified (1024, 1093, 1096, 1097, 1110, 1112, and 1127) that were able to inhibit the bit the binding of MN-rgp120 to recombinant CD4 in ELISA (FIG. 1) or solid phase or cell surface radioimmunoassays (21, 33). Previous studies have shown that two distinct classes of CD4 blocking monoclonal antibodies occur: those that bind to conformation dependent (discontinuous) epitopes (16, 26, 33, 35, 45) and those that bind to conformation independent (sequential) epitopes (4, 7, 21, 33, 43).

To distinguish between these two alternatives, the binding of the monoclonal antibodies to denatured (reduced and carboxymethylated) MN-rgp120 (RCM-gp120) was measured by ELISA as described previously (33). As illustrated in Table 4, below, it was found that all of the CD4 blocking monoclonal antibodies reacted with the chemically denatured protein; indicating that they all recognized conformation independent (sequential) epitopes.

TABLE 4

Properties of monoclonal antibodies to MN-rgp120

| MAb | CD4 Inhibitors | HIV-1 mn Neutralization | HIV-1 mn V3 | CM-rgp120 | C4 Domain peptides | rg120 cross reactivity |
|---|---|---|---|---|---|---|
| 1024 | + | + | – | + | – | 2 |
| 1093 | + | + | – | + | – | 2 |
| 1096 | + | + | – | + | – | 2 |
| 1097 | + | + | – | + | – | 2 |
| 1110 | + | + | – | + | – | 2 |
| 1112 | + | + | – | + | – | 2 |
| 1127 | + | + | – | + | – | 2 |
| 1026 | – | + | + | + | – | 1,2,3,4,6 |
| 1092 | – | – | – | + | – | 1,2,3,4,5 |
| 1126 | – | – | – | + | – | 1,2,3,5,7 |
| 1086 | – | – | – | + | – | 2 |
| 13H8 | + | – | – | + | 1,3 | 1,2,3,4,5,6,7 | rgp120 cross reactivity:
1 IIIB-rg120;
2 MN-rgp120,
3 NYS-rgp120;
4 JrCSF-rgp120;
5 Z6-rgp120;
6 Z321-rgp120;
7 A244-rgp120
C4 domain peptides:
1 FINMWQEVGKAMYAPPIS (SEQ. ID. NO. 24);
2 MWQEVGKAMYAP (SEQ. ID. NO. 25);
3 GKAMYAPPIKGQIR (SEQ. ID. NO. 26)

Figure 2:
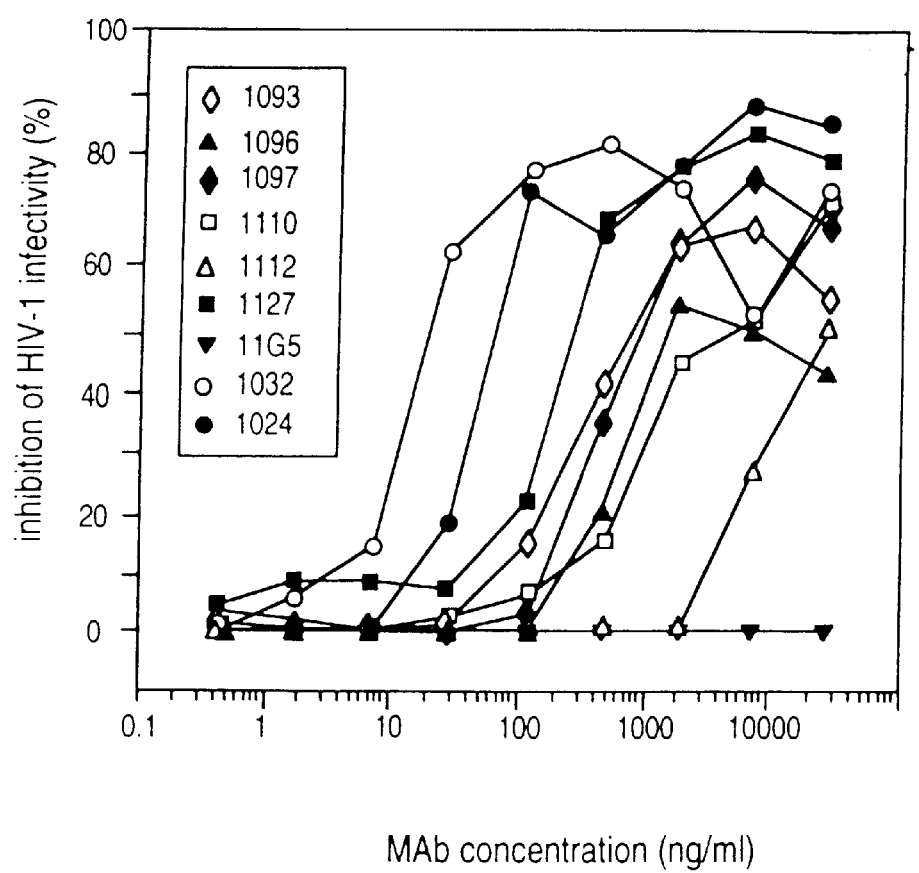
FIG. 2 shows neutralizing activity of CD4-blocking monoclonal antibodies to MN-rgp120. Monoclonal antibodies that blocked the binding of MN-rgp120 to CD4 were screened for the capacity to inhibit the infection of MT2 cells by the MN strain of HIV-1 in vitro. Cell free virus was added to wells containing serially diluted antibodies and incubated at 4° C. for 1 hr. After incubation, MT-2 cells were added to the wells and the cultures were then grown for 5 days at 37° C. Cell viability was then measured by addition of the colorimetric tetrazolium compound MTT as described in reference (35) of Example 1. The optical densities of each well were measured at 540 nm using a microtiter plate reading spectrophotometer. Inhibition of virus infectivity was calculated by dividing the mean optical densities from wells containing monoclonal antibodies by the mean value of wells that received virus alone. Monoclonal antibodies that blocked CD4 binding are the same as those indicated in Figure Legend 1. Data from the V3-directed monoclonal antibody to MN-rgp120 (1034) is provided as a positive control. Data obtained with the V3 directed monoclonal antibody, 11G5, specific for the IIIB strain of HIV-1 (33) is shown as a negative control.

The cross reactivity of these monoclonal antibodies was assessed by ELISA as described previously (33). In these experiments, the ability of the monoclonal antibodies to bind to a panel of seven rgp120s, prepared from the IIIB, MN, Z6, Z321, MY-5, A244, and JRcsf isolates of HIV-1, was measured by ELISA (33). It was found that all of the CD4 blocking noclonal antibodies were strain specific and bound only to gp120 from the MN strain of HIV-1 (Table 4). However, other antibodies from the same fusion (1026,1092, and 1126) exhibited much broader cross reactivity (Table 4, FIG. 2), as did a CD4 blocking monoclonal antibody to IIIB-rgp120 (13H8) described previously (33).

Further studies were Performed to characterize the neutralizing activity of the antibodies to MN-rgp120. In these studies, monoclonal antibodies were incubated with cell free virus (HIV-1$_{MN}$), and the resulting mixture was then used to infect MT-2 cells in microtiter plates. After 5 days, the plates were developed by addition of the calorimetric dye, MTT, and cell viability was measured spectrophotometrically. It was found (Table 4, FIG. 2) that all of the CD4 blocking monoclonal antibodies were able to inhibit viral infectivity. However the potency of the monoclonal antibodies varied considerably with some monoclonal antibodies (eg. 1024) able to inhibit infection at very low concentrations (IC$_{50}$ of 0.08 μg per ml) whereas other monoclonal antibodies (eg. 1112) required much higher concentrations (IC$_{50}$ of 30 μg per ml). In control experiments two monoclonal antibodies to MN-rgp120 from the same fusion (eg.1086,1092) were ineffective, whereas the 1026 monoclonal antibody exhibited potent neutralizing activity. Similarly, monoclonal antibodies to the V3 domain of IIIB-rgp120 (10F6, 11G5) known to neutralize the infectivity HIV-1$_{IIIB}$ (33), were unable to neutralize the HIV-1$_{MN}$ virus.

Binding studies using synthetic peptides were then performed to further localize the epitopes recognized by these monoclonal antibodies as described previously (33). When a peptide corresponding to the V3 domain (3) of MN-rgp120 was tested, it was found that none of the CD4 blocking antibodies showed any reactivity. However the epitope recognized by the non-CD4 blocking monoclonal antibody, 1026, prepared against MN-rgp120could be localized to the V3 domain by virtue of its binding to this peptide. In other experiments, three synthetic peptides from the C4 domain of gp120 that incorporated sequences recognized by the CD4 blocking, weakly neutralizing monoclonal antibodies described by McKeating et al. (26) were tested (Table 4). It was found that none of the CD4 blocking monoclonal antibodies to MN-rgp120 reacted with these peptides, however the non-neutralizing, CD4 blocking 13H8 monoclonal antibody bound to the peptides corresponding to residues 423–440 of IIIB-gp120 and residues 431–441 of MN-gp120, but not to that corresponding to residues 426–437 of IIIB-gp120. Thus the 13H8 monoclonal antibody recognized a epitope that was similar, if not identical, to that described by McKeating et al. (26). This result is consistent with the observation that the 13H8 monoclonal antibody and the monoclonal antibodies described by Cordell et al. (4) and McKeating et al. (26) exhibited considerable cross reactivity, whereas the antibodies to MN-rgp120 were highly strain specific.

CD4 blocking antibodies recognize epitopes in the C4 domain. Previously, a strain specific, CD4 blocking monoclonal antibody (5C2) raised against IIIB-rgp120 was found to recognize an epitope in the C4 domain of IIIB-rgp120 (21, 33). Although the 5C2 monoclonal antibody was able to block the binding of rgp120 to CD4, it was unable to neutralize HIV-1 infectivity in vitro (7). Affinity columns prepared from 5C2 adsorbed an 11 amino acid peptide (residues 422 to 432) from a tryptic digest of gp120 (21), however monoclonal antibody 5C2 was unable to recognize this peptide coated onto wells of microtiter dishes in an ELISA format (Nakamura et al., unpublished results).

Figure 3A:
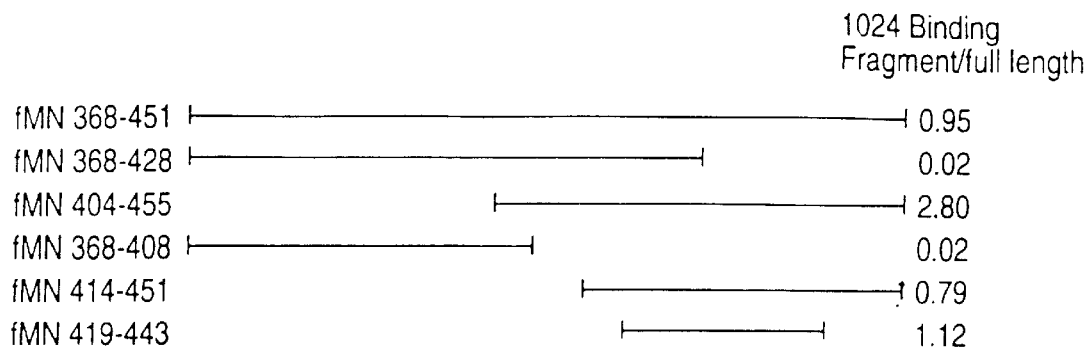
FIG. 3 is a diagram of gp120 fragments used to localize the epitopes recognized by the CD4 blocking monoclonal antibodies to MN-rgp120. A series of fragments (A) corresponding to the V4 and C4 domains (B) (SEQ. ID. NO. 14) of the gene encoding MN-rgp120 were prepared by PCR. The gp120 gene fragments were fused to a fragment of the gene encoding Herpes Simplex Virus Type 1 glycoprotein D that encoded the signal sequence and 25 amino acids from the mature amino terminus. The chimeric genes were assembled into a mammalian cell expression vector (PRK5) that provided a CMV promoter, translational stop codons and an SV40 polyadenylation site. The embryonic human kidney adenocarcinoma cell line, 293s, was transfected with the resulting plasmid and recombinant proteins were recovered from growth conditioned cell culture medium. Fragments of MN-rgp120, expressed as HSV-1 Gd fusion proteins, were produced by transient transfection of 293s cells (Example 1). To verify expression, cells were metabolically labeled with [$^{35}$S]-methionine, and the resulting growth conditioned cell culture supernatants were immunoprecipitated (C) using a monoclonal antibody, 5B6, specific for the amino terminus of HSV-1 Gd and fixed S. aureus. The immunoprecipitated proteins were resolved on 4 to 20% acrylamide gradient gels using SDS-PAGE and visualized by autoradiography. The samples were: Lane 1, FMN.368–408; lane 2, FMN.368–451; lane 3, FMN.419–443; lane 4, FMN.414–451; lane 5, MN-rgp120. The gel demonstrated that the proteins were expressed and migrated at the expected molecular weights.
Figure 3B:
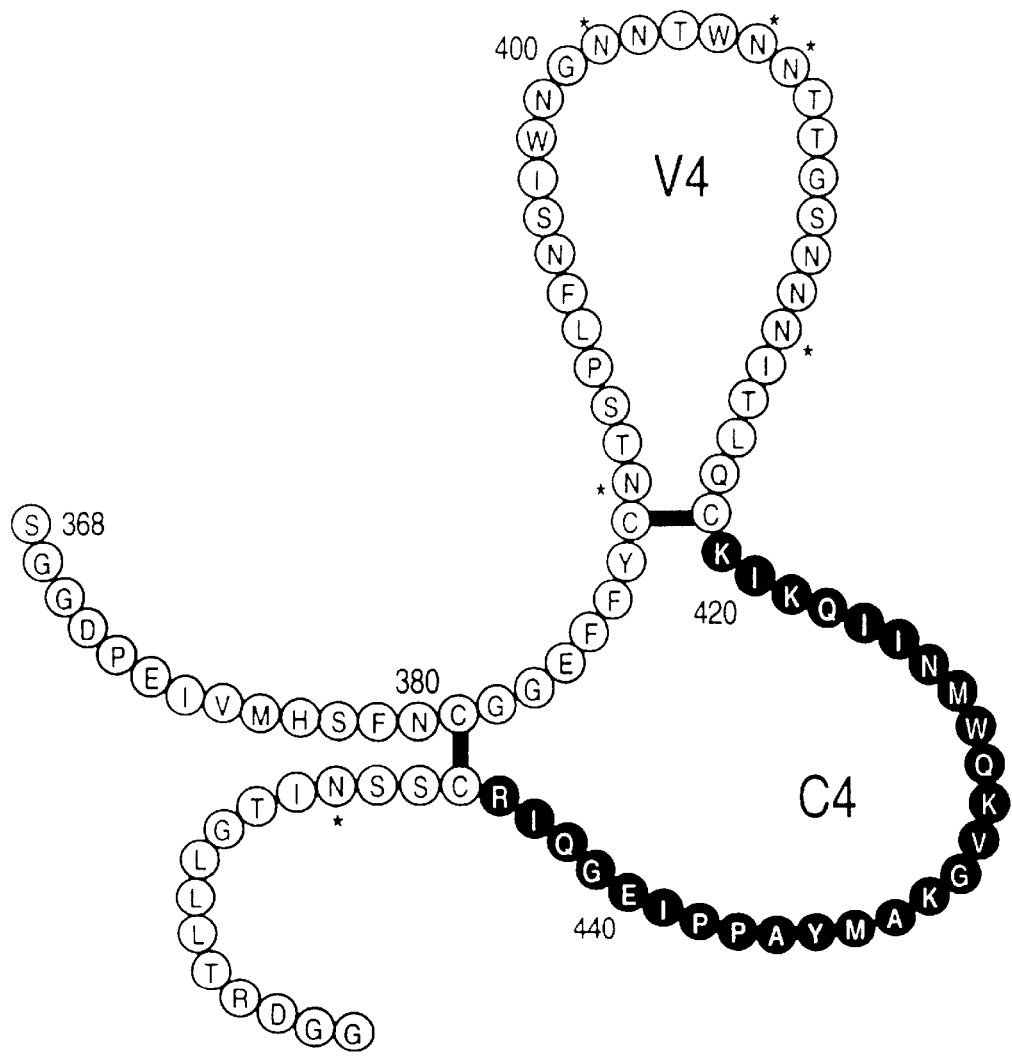
Figure 6:
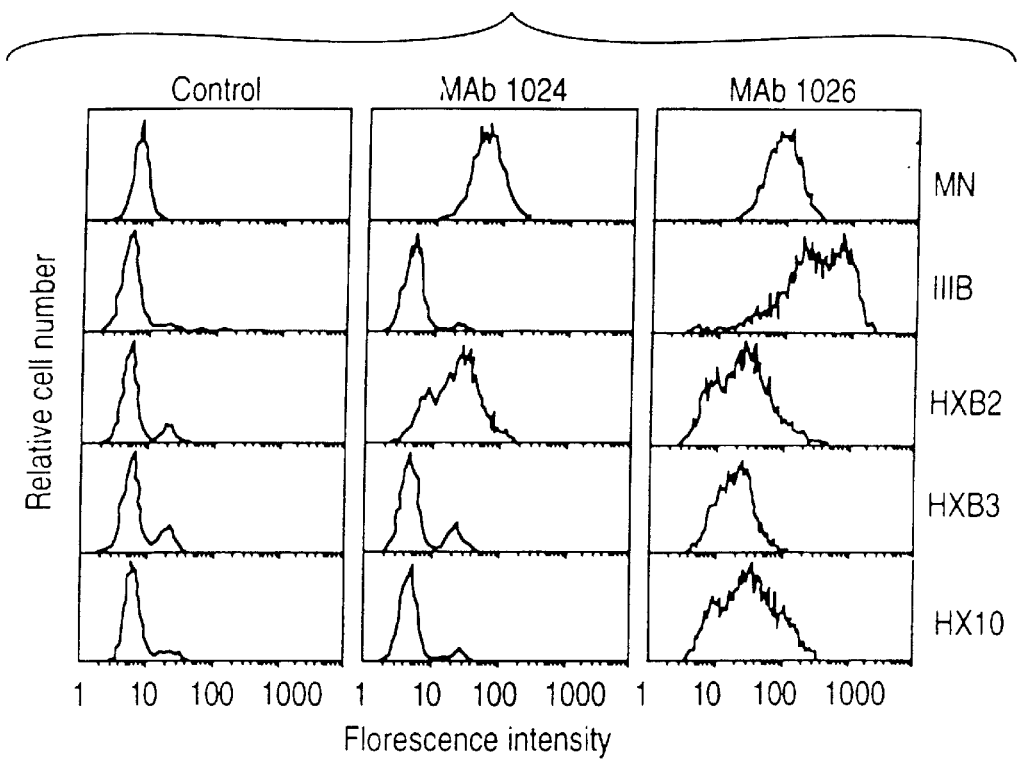
FIG. 6 illustrates the reactivity of monoclonal antibody 1024 with HIV-$1_{LAI}$ substrains. The cell surface binding of the C4 domain reactive monoclonal antibody 1024 to H9 cells chronically infected with the IIIB, HXB2, HXB3, and HXB10 substrains of HIV-1 LAI or HIV-1MN was analyzed by flow cytometry. Cultures of virus infected cells were reacted with either monoclonal antibody 1024, a nonrelevant monoclonal antibody (control), or a broadly cross reactive monoclonal antibody (1026) raised against rgp120. After washing away unbound monoclonal antibody, the cells were then labeled with fluorescein conjugated oat antibody to mouse IgG (Fab')$_2$, washed and fixed with paraformaldehyde. The resulting cells were analyzed for degree of fluorescence intensity using a FACSCAN (Becton Dickensor, Fullerton, Calif.). Fluorescence was measured as mean intensity of the cells expressed as mean channel number plotted on a log scale.
Figure 7A:
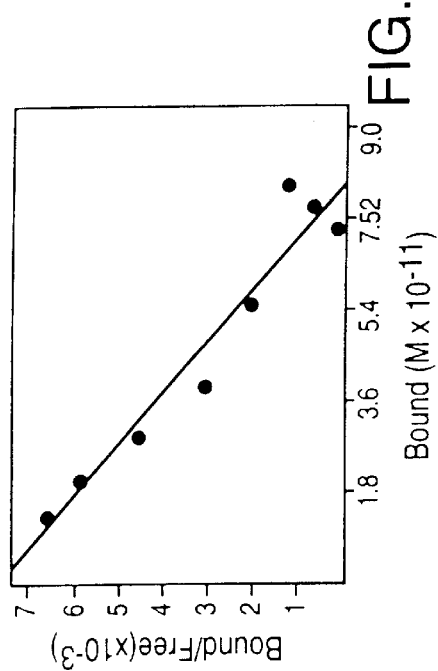
FIG. 7 shows the determination of the binding affinity of monoclonal antibodies for MN-rgp120. CD4 blocking monoclonal antibodies raised against MN-rgp120 (1024 and 1097) or IIIB-rgp120 (13H8 and 5C2) were labeled with [$^{125}$I] and binding titrations using MN-rgp120 (A and B) or IIIB-rgp120 (C and D) were carried out as described in the Example 1. A, binding of monoclonal antibody 1024; B binding of monoclonal antibody 1097; C, binding of monoclonal antibody 13H8; and D binding of monoclonal antibody 5C2.
Figure 7C:
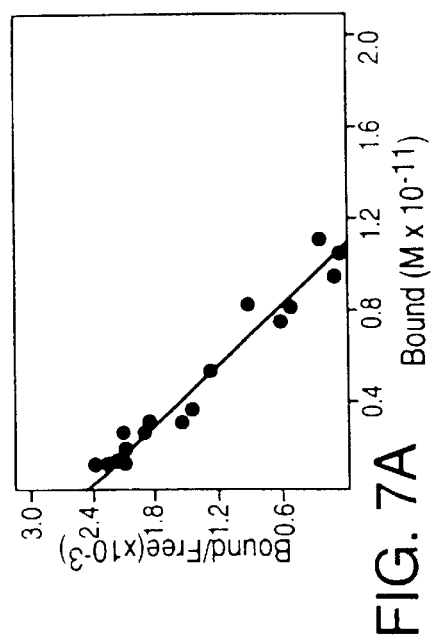
Figure 7B:
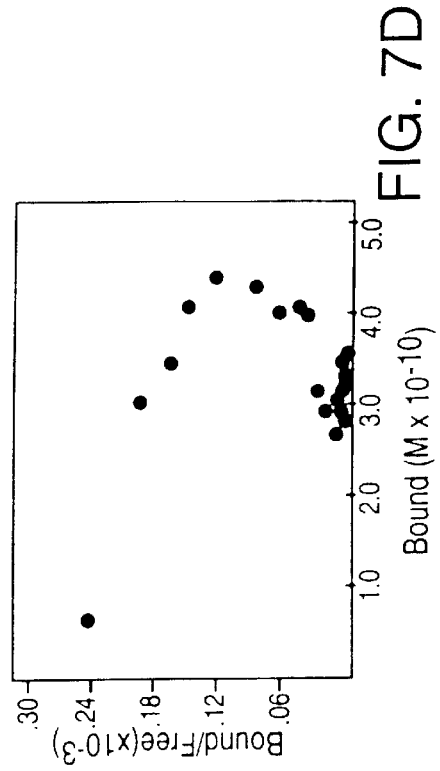
Figure 7D:
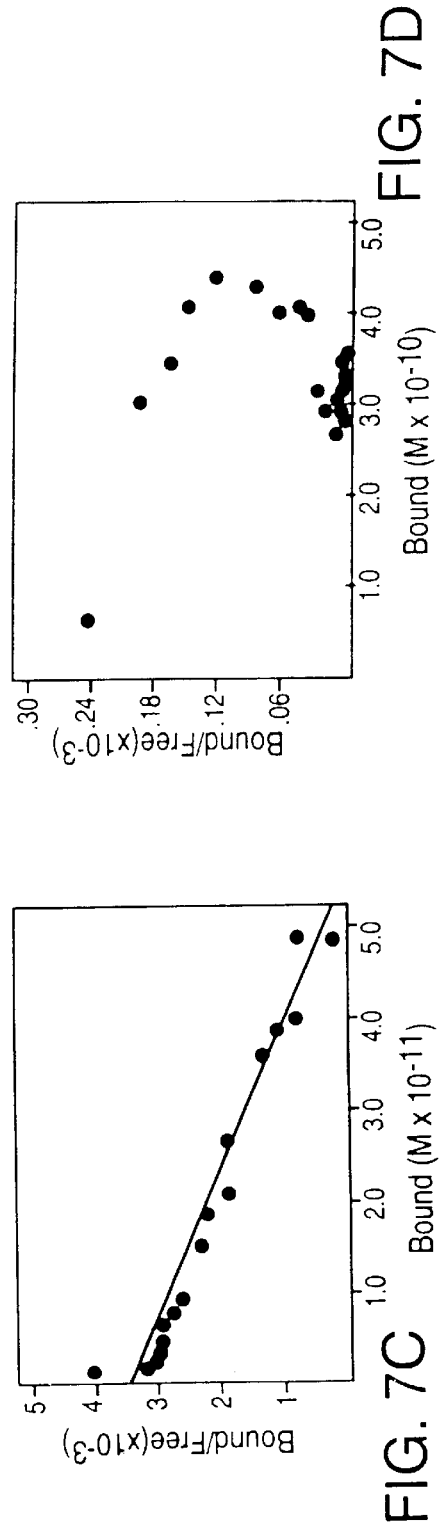

To determine whether the CD4 blocking monoclonal antibodies raised against MN-rgp120 recognized the corresponding epitope in the C4 domain of MN-rgp120, a series of overlapping fragments, spanning the V4 and C4 domains of HIV-1$_{MN}$ gp120, were prepared for expression in mammalian cells. A diagram of the fragments expressed is shown in FIGS. 3A and 3B. The C4 domain fragments were expressed as fusion proteins that incorporated the signal sequence and amino terminal 25 amino acids of HSV-1 glycoprotein D as described above.

Plasmids directing the expression of the chimeric C4 domain fragments were transfected into 293 cells, and their expression was monitored by radioimmunoprecipitation studies where a monoclonal antibody, 5B6, specific for the mature amino terminus of glycoprotein D was utilized. It was found (FIG. 3B) that all of the fragments were expressed and exhibited mobilities on SDS-PAGE gels appropriate for their size. Thus fMN.368–408 (lane 1) exhibited a mobility of 19 kD; fMN.368–451 (lane 2) exhibited a mobility of 29 kD; fMN.419–433 (lane 3) exhibited a mobility of 6 kD, and fMN.414–451 (lane 4) exhibited a mobility of 6.1 kD.

The binding of monoclonal antibody 1024 to the recombinant fragments was then determined by ELISA (as described in Example 1). It was found (FIG. 3A) that monoclonal antibody 1024 reacted with the fragments that contained the entire C4 domain of MN-rgp120 (fMN$_{368-451}$, fMN$_{404-455}$), but failed to bind to a fragment derived from the adjacent V4 domain (fMN$_{368-408}$) or to another fragment that contained V4 domain sequences and the amino terminal half of the C4 domain (fMN$_{368-428}$) The fact that 1024 bound to the fMN$_{414-451}$ and fMN$_{419-443}$ fragments demonstrated that the epitopes recognized by all of these monoclonal antibodies were contained entirely between residues 419 and 443 in the C4 domain.

Residues recognized by monoclonal antibodies that block binding of MN-rgp120 to CD4. To identify specific amino acid residues that might be part of the epitopes recognized by these monoclonal antibodies, the sequence of the C4 domain of MN-rgp120 was compared to those of the gp120s from the six other rgp120s that failed to react with the CD4 blocking monoclonal antibodies (FIG. 4). It was noted that the sequence of MN-rgp120 was unique in that K occurred at position 429 whereas the other rgp120possessed either E,G, or R at this position. Another difference was noted at position 440 where E replaced K or S. To evaluate the significance of these substitutions, a series of point mutations were introduced into the MN-rgp120 gene (FIG. 5). Plasmids expressing the mutant proteins were transfected into 293s cells, and expression was verified by radioimmunoprecipitation with a monoclonal antibody (1034) directed to the V3 domain of MN-rgp120. Cell culture supernatants were harvested and used for the monoclonal antibody binding studies shown in Table 6. To verify expression, radio-immunoprecipitation studies using cell culture supernatants from cells metabolically labeled with [$^{35}$]S-methionine were performed using the 1024 monoclonal antibody specific for the C4 domain of MN-rgp120 (A) or the 1034 monoclonal antibody specific for the V3 domain of MN-rgp120. Immune complexes were precipitated with the use of fixed *S. aureus* and the adsorbed proteins were resolved by SDS-PAGE. Proteins were visualized by autoradiography. The samples were: Lane 1, MN.419A; lane 2 MN.421A; lane 3 MN.429E; lane 4, MN.429A; lane 5, MN.432A; lane 6, MN.440A; lane 7, MN-rgp120. The immunoprecipitation study showed that 1024 antibody binds well to all the variants except 3 and 4 which are mutated at residue 429. 1034 antibody was used as a control and precipitates with anti-V3 antibodies.

The effect of these mutations on the binding of the CD4 blocking monoclonal antibodies was then evaluated by ELISA as illustrated in Table 5, below.

TABLE 5

Binding of CD4 blocking monoclonal antibodies to C4 domain mutants

| Proteins/MAbs | 1024 | 1093 | 1096 | 1097 | 1110 | 1112 | 1127 | 5C2 |
|---|---|---|---|---|---|---|---|---|
| MN-rgp120 | 1.0 | 1.0 | 1.0 | 1.0 | 1.0 | 1.0 | 1.0 | 0.05 |
| MN-419A | 1.11 | 1.10 | 0.94 | 1.21 | 0.78 | 0.95 | 1.10 | ND |
| MN-421A | 1.11 | 1.60 | 0.88 | 1.42 | 1.34 | 0.91 | 1.10 | ND |
| MN-429E | 0.03 | 0.07 | 0.11 | 0.04 | 0.10 | 0.10 | 0.02 | ND |
| MN-429A | 0.10 | 0.07 | 0.14 | 0.04 | 0.09 | 0.11 | 0.05 | ND |
| MN-432A | 0.77 | 0.15 | 0.59 | 0.08 | 0.12 | 0.24 | 0.26 | ND |
| MN-440A | 1.06 | 1.13 | 1.08 | 0.87 | 1.12 | 1.0 | 1.3 | ND |
| IIIB-rgp120 | 0.03 | ND | ND | ND | ND | ND | ND | 1.0 |
| MN-423F | ND | ND | ND | ND | ND | ND | ND | 0.45 |
| MN-423F,429E | ND | ND | ND | ND | ND | ND | ND | 1.09 |

Data represent the relative binding of MAbs to the native and mutant forms of rgp120. Values were calculated by dividing the binding (determined by ELISA) of the CD4 blocking MAbs to the proteins indicated by the values obtained for the binding of a V3 specific MAb (1034) to the same proteins (as described in Example 1).

It was found that replacement of K$_{440}$ with an A residue (MN.440A)had no effect on the binding of the 1024 monoclonal antibody or any of the other CD4 blocking monoclonal antibodies (Table 5). The significance of K at position 429 was then evaluated by substitution of either A (MN.429A) or E (MN.429E) at this location. It was found that the A for K substitution at position 429 (MN.420A) markedly reduced the binding of the 1024 monoclonal antibody and all of the other CD4 blocking monoclonal antibodies (Table 5). Similarly, the replacement of E for K (MN.429E) at this position totally abrogated the binding of the 1024 monoclonal antibody and all of the other CD4 blocking monoclonal antibodies (Table 5). Several other mutants were constructed to evaluate the role of positively charged residues in the C4 domain. It was found that A for K substitutions at positions 419 (MN.419A) and 421 (MN.421A) failed to interfere with the binding of any of the CD4 blocking monoclonal antibodies as illustrated in Table 6, below.

TABLE 6

Correlation Between Antibody Binding Affinity and Virus Neutralizing Activity

| MAb | Block | $K_d$, nM[c] | $IC_{50}$, nM[d] |
|---|---|---|---|
| 1024[e] | + | 2.7 ± 0.9 | 0.4 |
| 1086[e,f] | − | 9.7 ± 2.2 | — |
| 1093[e] | + | 9.9 ± 2.6 | 3.3 |
| 1096[e] | + | 10 ± 6 | 12 |
| 1097[e] | + | 13.4 ± 3.7 | 12 |
| 1110[e] | + | 12.1 ± 1.7 | 12 |
| 1112[e] | + | 20 ± 4.4 | 200 |
| 1127[e] | + | 9.3 ± 4 | 3.3 |
| 1086[e,f] | − | 9.7 ± 2.2 | — |
| 13H8[f,g] | +[b] | 22 ± 6 | — |

[a]Blocked binding of rgp120 MN to CD4.
[b]Blocked binding of rgp120 IIIb, not rgp120 MN, to CD4.
[c]Mean of four determinations calculated using the method of Scatchard (40).
[d]Neutralization of HIV-$1_{MN}$ infectivity in vitro.
[e]Anti-rgp120 MN antibody.
[f]Did not neutralize HIV-1 infectivity.
[g]Anti-rgp120 IIIb antibody.

However, when K at position 432 was replaced with A (MN432. A), the binding of all of the CD4 blocking antibodies was markedly reduced (Table 5). Interestingly, the binding of monoclonal antibody 1024 appeared less affected by this substitution than the other monoclonal antibodies (Table 5). Thus, these studies demonstrated that $K_{429}$ and $K_{432}$ were critical for the binding of all of the CD4 blocking monoclonal antibodies, and that $K_{419}$, $K_{421}$, and $K_{440}$ did not appear to play a role in monoclonal antibody binding.

Amino acids recognized monoclonal antibodies that block binding of IIIB-rgp120 to CD4. The identification of residues 429 and 432 as being part of the epitope recognized by the MN-rgp120 specific CD4 blocking monoclonal antibodies was particularly interesting since this region was previously found to be implicated in the binding of the 5C2 monoclonal antibody (21). The properties of the 1024 like-monoclonal antibodies and the 5C2 monoclonal antibody differed from the C4 reactive monoclonal antibodies described by other investigators (4, 43) in that the former appeared strain specific and the latter were broadly cross reactive. To account for the strain specificity of these monoclonal antibodies, the sequence of the eleven amino acid peptide of IIIB-rgp120 recognized by monoclonal antibody 5C2 was compared to the corresponding sequence of MN-rgp120. It was found that the IIIB protein differed from the MNB protein at positions 429 where K replaced E and at position 423 where I replaced F (FIG. 5). Because it was known from previous studies (33) that the 5C2 monoclonal antibody was unable to bind to gp120 from two strains (i.e., NY-5 and JRcsf) that also possessed E at position 423, it seemed unlikely that this position could account for the strain specificity of 5C2. Sequence comparison (FIG. 5) also showed that gp120 from HIV-$1_{IIIB}$ was unique in that a phenylalanine residue occurred at position 423 whereas the other six strains examined possess an I at this position.

To determine whether residues 423 and/or 429 could account for the type specificity of the 5C2 monoclonal antibody, a mutant of MN-rgp120 was constructed which incorporated an F for I replacement at position 423 (MN.423F). In addition, the MN-rgp120 mutant, MN.429E (described above) was further mutagenized to incorporate a F for I substitution at position 423 (MN.423F), thus resulting in a double mutant (MN.423F,429E) whose sequence was identical to that of IIIB-rgp120 within the 10 amino acid 5C2 epitope (FIG. 4). The expression of these mutants in 293s cells was verified by radioimmunoprecipitation using rabbit polyclonal antisera to MN-rgp120. When the binding of the 13H8 monoclonal antibody to a set of mutants incorporating substitutions at position 423 and 429 was examined, it was found that none of the replacements effected the binding of this antibody (data not shown). When the 5C2 monoclonal antibody was examined, it was found that the F for I replacement (MN.423 F) conferred partial reactivity (Table 5). When the double mutant (MN.423F,429E), containing the F for I substitution as well as the E for K substitution was tested, binding that was indistinguishable from that to IIIB-rgp120 was observed (Table 5). These results demonstrated that F at position 423 and E at position 429 both play a role in binding of the 5C2 monoclonal antibody, and suggest that the strain specificity of 5C2 can be attributed to the residues at these positions.

Examination of the sequences of gp120 from the various clones of LAI that have been analyzed revealed that several substrains of LAI differed from each other in the C4 domain. Thus the sequences of the IIIB (30), Bru (46), and HXB3 (6) clones of LAI were identical at positions 423 and 429 where F and E residues occurred respectively. However, the sequence of the HXB2 substrain (36) differed from the others at these positions where, like MN-rgp120, K replaced E and at position 423 where I replaced F (FIG. 5). Similarly, the HX10 and BH10 substrains (36, 37) differed only at position 423 where, like HIV-$1_{MN}$, I replaced F. Based on the mutagenesis experiments above, it would be predicted that monoclonal antibody 1024 should be able to bind to gp120 from the HXB2 substrain of LAI, but not the HXB3 substrain. If $I_{423}$ was important for binding, then 1024 should also bind the HX10 substrain.

To test this hypothesis, the binding of monoclonal antibody 1024 to the surface cells infected with either IIIB, HXB2, HXB3, and HX10 substrains of HIV-$1_{LAI}$ was measured by flow cytometry. It was found that monoclonal antibody 1024 was able to bind only HXB2 providing further confirmation that residues 423 and 429 were important for the binding of this antibody. The fact that monoclonal antibody 1024 did not bind to HX10 infected cells suggested that $I_{423}$ was not important for the binding of this monoclonal antibody. Thus these studies demonstrate that reactivity with the 1024 monoclonal antibody segregates with the occurrence of F and E residues at positions 423 and 429, respectively, and shows that substrains of HIV-$1_{LAI}$ differ from one another at a functionally significant epitope in the C4 domain.

Figure 8:
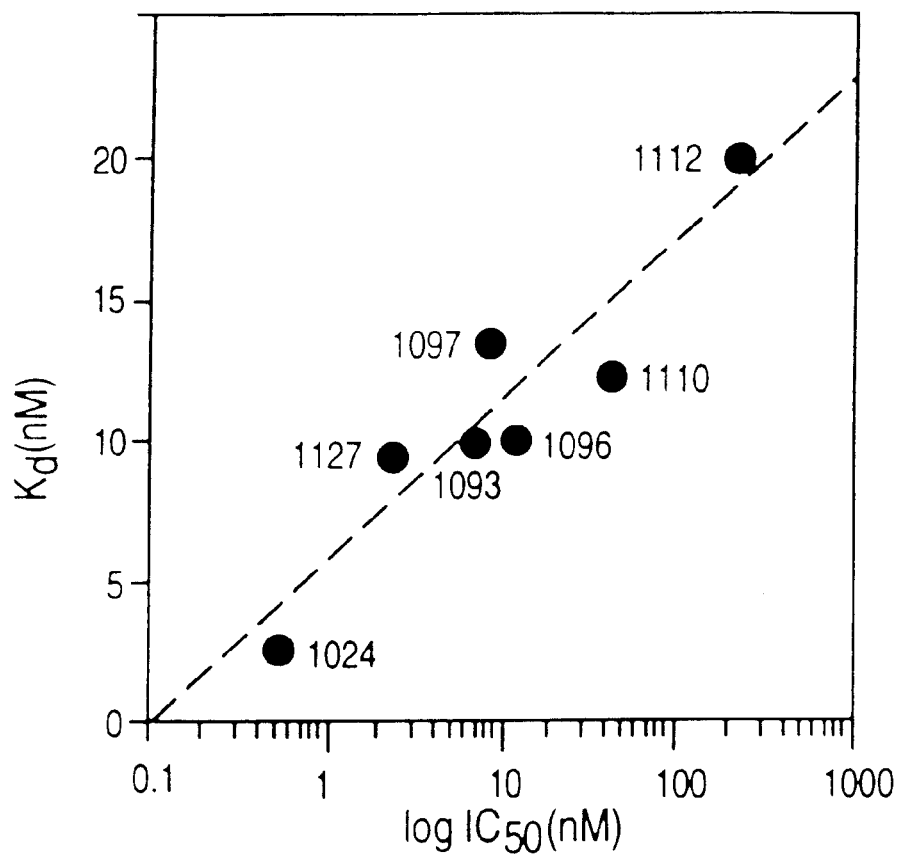
FIG. 8 shows the correlation between gp120 binding affinity ($K_d$) and neutralizing activity (IC50) of monoclonal antibodies to the C4 domain of MN-rgp120. Binding affinities of monoclonal antibodies to the C4 domain of gp120 were determined by Scatchard analysis (FIG. 9, Table 5). The resulting values were plotted as a function of the log of their neutralizing activities ($IC_{50}$) determined in FIG. 2 and Table 6.

Neutralizing activity of CD4 blocking antibodies correlates with their binding affinity. To account for the difference in virus neutralizing activity between the CD4 blocking monoclonal antibodies, their gp120 binding affinities were determined by competitive binding of [$^{125}$I]-labeled monoclonal antibody to rgp120 (Table 6). Typical Scatchard analysis of data from these assays is shown in FIG. 7 (A to C). Linear, one-site binding kinetics were observed for all the monoclonal antibodies to MN-rgp120, suggesting that only a single class of sites was recognized, and that there was no cooperativity between two combining sites of each immunoglobulin molecule. It was found (FIG. 7A, Table 6) that monoclonal antibody 1024, which exhibited the most potent virus neutralizing activity ($IC_{50}$ of 0.08 μg per ml), possessed the lowest $K_d$ (2.7 nM). In contrast (FIG. 7C, Table 6), monoclonal antibody 1112, the antibody that exhibited the weakest virus neutralizing activity ($IC_{50}$ of 30 μg per ml) possessed the highest $K_d$ (20 nM). $K_d$S for six additional CD4-blocking monoclonal antibodies raised against MN-rgp120 were also determined (Table 6). It was found that monoclonal antibodies that possessed intermediate $K_d$S similarly possessed intermediate neutralization $IC_{50}$ values. To explore the relationship between virus neutralizing activity and gp120 binding affinity, the data in Table 6 was plotted in several different ways. It was found that when the $K_d$ of the monoclonal antibodies was plotted as a function of the log of the $IC_{50}$, a linear relationship was obtained (FIG. 8). Using this analysis a correlation coefficient (r) of 0.97 was obtained. Thus, this graph demonstrates that the virus neutralizing activity of these monoclonal antibodies is directly proportional to the gp120 binding affinity, and that the threshold for neutralization at this epitope is defined by the slope of the graph in FIG. 8.

A similar analysis was performed with the non-neutralizing CD4 blocking monoclonal antibodies to IIIB-rgp120, 5C2 and 13H8. The binding curve for 13H8 (FIG. 7C) showed that it bound to a single class of sites on IIIB-rgp120 with a $K_d$ of 22 nM. The affinity of 5C2 could not be determined by this assay because at antibody concentrations greater than 5 nM, non-linear (reduced gp120 binding) was observed. This effect was suggestive steric hindrance at these concentrations or negative cooperativity between combining sites. The binding affinity was also determined for the non-neutralizing, non-CD4 blocking monoclonal antibody to MN-rgp120, 1086. The fact that this antibody exhibited a binding affinity similar (9.7 nM) to many of the neutralizing monoclonal antibodies but failed to inhibit infectivity, proves that high antibody binding affinity alone is not sufficient for neutralization.

Effect of C4 Domain Mutants on CD4 binding. Finally, the CD4 binding properties of the series of MN-rgp120 mutants, constructed to localize the C4 domain epitopes, were measured in a qualitative co-immunoprecipitation assay. In these studies the ability of the mutagenized MN-rgp120 variants to co-immunoprecipitate CD4 was evaluated as described previously (21) in a qualitative co-immunoprecipitation assay similar to that described previously (19). Briefly, 293 cells, transfected with plasmids directing the expression of MN-rgp120 variants described in FIG. 5, were metabolically labeled with [$^{35}$S]-methionine, and the growth conditioned cell culture supernatants were incubated with rsCD4. The resulting rsCD4:gp120 complexes were then immunoprecipitated by addition of the CD4 specific monoclonal antibody, 465 (A) or a positive control monoclonal antibody (1034) directed to the V3 domain of MN-rgp120 (B). The immunoprecipitated proteins were resolved by SDS-PAGE and visualized by autoradiography as described previously (3). The samples were: Lane 1, MN.419A; lane 2, MN.421A; lane 3, MN.429E; lane 4, MN.429A; lane 5, MN.432A; lane 6, MN.440A; lane 7, MN-rgp120. The gel showed that the mutants that block antibody binding do not block binding of CD4. Therefore, the antibodies do not bind to the gp120 CD4-binding contact residues. This indicates that steric hinderance may inhibit antibody binding, rather than that the antibodies bind directly to the CD4 contact residues to inhibit binding.

It was found that all of the variants in which apolar A residue was substituted for the charged K or E residues (e.g., MN.419A, MN.421A, MN.432A, and MN.440A) were still able to co-immunoprecipitate rsCD4. Similarly, the replacement of E for K at position 429 (MN.429E), the replacement of F for I at position 423 (MN.423F) or the mutant which incorporated both mutation (MN.423F,429E) also showed no reduction in their ability to co-immunoprecipitate rsCD4. Thus, radical amino acid substitutions at five positions failed to affect the binding of gp120 to CD4. These results were consistent with previous studies (5, 21, 34) where it was found that only a few of the many mutations that have been induced in this region effected CD4 binding.

This study indicates that neutralizing epitopes in the C4 domain have now been found to be located between about residues 420 and 440. In addition, the critical residues for antibody binding are residues 429 and 432.

EXAMPLE 2

Identification of V2 Neutralizing Epitopes

The procedures described in Example 1 were used to map epitopes in the V2 region of gp120. Table 7 illustrates the results of mutagenicity studies to map V2 neutralizing epitopes. In the table, the columns indicate the comparison of binding of the monoclonal antibodies with wild type (WT) gp120 in comparison to various mutations of gp120 using standard notation. For example, "G171R" indicates that the glycine (G) at residue 171 has been replaced by an arginine (R). "172A/173A" indicates that the residues at 172 and 173 have been replaced by alanine. The neutralizing monoclonal antibodies tested (MAbs) are listed in the rows. The numerical values in the table are the optical density value of an ELISA assay performed as described in Example 1 to measure the amount of antibody binding. The underlined values indicate significantly reduced binding, indicating the substituted residue is critical for binding of the antibody.

TABLE 7

| MAbs | WT | G171R, M174V | 172A/ 173A | E187V | 187V/ 188S |
|------|------|------|------|------|------|
| 6E10 | 1.00 | 0.10 | 1.28 | 0.60 | 0.25 |
| 1017 | 1.00 | 0.70 | 1.10 | 0.87 | 0.04 |
| 1022 | 1.00 | 0.80 | 1.10 | 1.00 | 0.00 |
| 1028 | 1.00 | 0.90 | 1.18 | 1.07 | 0.04 |
| 1029 | 1.00 | 0.83 | 1.16 | 1.01 | 0.16 |
| 1019 | 1.00 | 0.13 | 1.30 | 0.75 | 0.74 |
| 1027 | 1.00 | 0.00 | 1.20 | 0.80 | 0.64 |
| 1025 | 1.00 | 0.69 | 0.00 | 0.00 | 0.83 |
| 1088 | 1.00 | 0.73 | 1.12 | 0.94 | 0.03 |
| 13H8 | 1.00 | 0.77 | 0.78 | 0.48 | 0.65 |

| MAbs | WT | 177A | 172A/ 173A | 188A | 183A |
|------|------|------|------|------|------|
| 6E10 | 1.00 | 0.36 | 0.52 | 0.64 | 0.43 |
| 1017 | 1.00 | 0.77 | 0.77 | 0.76 | 0.11 |
| 1022 | 1.00 | 0.86 | 0.72 | 0.14 | 0.00 |
| 1028 | 1.00 | 0.93 | 0.78 | 0.49 | 0.04 |
| 1029 | 1.00 | 0.88 | 0.85 | 0.53 | 0.16 |
| 1019 | 1.00 | 0.16 | 0.00 | 0.41 | 0.44 |
| 1027 | 1.00 | 0.00 | 0.02 | 0.41 | 0.49 |
| 1025 | 1.00 | 0.75 | 0.0 | 0.83 | 0.72 |
| 1088 | 1.00 | 0.77 | 0.77 | 0.53 | 0.00 |
| 13H8 | 1.00 | 0.72 | 0.72 | 0.53 | 0.60 |

As illustrated in Table 7, the study demonstrated that there are a series of overlapping neutralizing epitopes from been found to be located in the V2 region (residues 163 through 200), with most of the epitopes located between residues 163 and 200. In addition, the study indicates that the critical residues in the V2 domain for antibody binding are residues 171, 173, 174, 177, 181, 183, 187, and 188.

EXAMPLE 3

Immunization Studies gp120 from the MN, $GNE_8$, and $GNE_{16}$ strains of HIV was prepared by amplifying the gene from each isolate and cloning and expressing the gene in CHO cells as described in Berman et al., *J. Virol.* 66:4464–4469 (1992). Briefly, the gp160 gene was amplified with two rounds of amplification using the following nested primers according to the protocol by Kellog et al., pp 337–347 in PCR Protocols: a guide to methods and amplification. Innis et al. (eds.) Academic Press, Inc., New York.

First round primers:
AATAATAGCAATAGTTGTGTGGWCC (W is A or T)
ATTCTTTCCCTTAYAGTAGGCCATCC (Y is T or C)
Second round primers:
GGGAATTCGGATCCAGAGCAGAAGACAGT-GGCAATGA
GTCAAGAATTCTTATAGCAAAGCCCTTTCCAA The primers are SEQ. ID. NOs. 31–34. Each gene is then digested with the restriction endonucleases KpnI and AccI. The resulting fragment was subcloned into the Bluescript (+) phagemid M13 vector (Stratagene, Inc.) and sequenced by the dideoxynucleotide method (Sanger et al., *Proc. Natl. Acad. Sci.* USA 74:5463–5467 (1977)).

A fragment of the gp120 coding region was then used to construct a chimeric gene for expression in mammalian cells, as described in Lasky et al., Science 223:209–212 (1986). The 5' end was fused to a polylinker adjacent to a simian virus 40 (SV40) promoter and the 3' end was fused to a polylinker adjacent to the 3' untranslated sequences containing an SV40 polyadenylation signal. The expression vector (MN-rgp120) was co-transfected in CHO cells deficient in production of the enzyme dihydrofolate reductase, along with a plasmid (pSVdhfr) containing a cDNA encoding the selectable marker, dihydrofolate reductase. Cell lines expressing MN-rgp120 were isolated as described in Lasky et al., *Science* 223:209–212 (1986). The recombinant glycoprotein was purified from growth-corditioned cell culture medium by immunoaffinity and ion exchange chromatography as described in Leonard et al., *J. Biol. Chem.* 265:10373–10382 (1990).

gp120 from the $GNE_8$ and $GNE_{16}$ strains or HIV is prepared in the same manner as described for the MN isolate.

MN-rgp120 (300 µg/injection), $GNE_8$-rgp120 (300 µg/injection), and $GNE_{16}$-rgp120 (300 µg/injection) are prepared in an aluminum hydroxide adjuvant (as described in Cordonnier et al., *Nature* 340:571–574 (1989)). Six chimpanzees are injected at 0, 4, and 32 weeks. Sera are collected and assayed for neutralizing antibody to each strain of HIV at the time of each immunization and three weeks thereafter. At 35 weeks, each of the chimpanzees has significant levels of neutralizing antibodies to each strain.

At 35 weeks, the chimpanzees are randomly assigned to three groups. Each group is challenged with about 10 50% chimpanzee-infectious doses ($CID_{50}$) each of one of the vaccine isolates. One unimmunized chimpanzee (control) is also injected with the same amount of virus as the immunized chimpanzees for each vaccine strain.

Sera are drawn every two weeks throughout the study and assayed for antibodies to HIV core proteins and for the presence of HIV by PCR amplification and co-cultivation of peripheral blood mononuclear cells (PBMCs) from the chimpanzee together with activated human or chimpanzee PBMCs. The presence of antibodies to core proteins indicates the presence of viral infection as does the detection of amplified viral DNA or viral infection of co-cultivated cells.

The presence of virus is detected by PCR and co-cultivation methods in each unimmunized control animal between weeks 2 and 4 post challenge. Antibodies to core proteins appear in the control chimpanzees at six weeks post challenge. Neither virus nor antibodies are at detectable levels in any of the immunized chimpanzees at one year post challenge, indicating that the vaccine effectively protects the chimpanzees from infection from each of the challenge strains.

REFERENCES

1. Berman, P. W. et al., 1989. Expression and immunogenicity of the extracellular domain of the human immunodeficiency virus type 1 envelope glycoprotein, gp160. J. Virol. 63:3489–3498.
2. Berman, P. W. et al., 1990. Protection of chimpanzees from infection by HIV-1 after vaccination with gp120 but not gp160. Nature 345:622–625.
3. Berman, P. W. et al., 1992. Neutralization of multiple laboratory and clinical isolates of HIV-1 by antisera raised against gp120 from the MN isolate of HIV-1. J. Virol. 7:4464–4469.
4. Cordell, J. et al., 1991. Rat monoclonal antibodies to non-overlapping epitopes of human immunodeficiency virus type 1 gp120 block CD4 binding in vitro. Virology 185:72–79.
5. Cordonnier, A. et al., 1989. Single amino acid changes in HIV envelope affect viral tropism and receptor binding. Nature 340:571–574.
6. Crowl, R. et al., 1985. HTLV-III env gene products synthesized in *E. coli* are recognized by antibodies present in the sera of AIDS patients. Cell 41:979–986.
7. Dowbenko, D. et al., 1988. Epitope mapping of the human immunodeficiency virus type 1 gp120 with monoclonal antibodies. J. Virol. 62:4703–4711.
8. Eaton, D. et al., 1986. Construction and characterization of an active factor VIII lacking the central one-third of the molecule. Biochemistry 291:8343–8347.
9. Fouchier, R. A. M. et al., 1992. Phenotype-associated sequence variation in the third variable domain of the human immunodeficiency virus type 1 gp120 molecule. J. Virol. 66: 3183–3187.
10. Goudsmit, J. et al., 1988. Human immunodeficiency virus type 1 neutralization epitope with conserved architecture elicits early type-specific antibodies in experimentally infected chimpanzees. Proc. Natl. Acad. Sci. U.S.A. 85:4478–4482.
11. Graham, F. et al., 1973. A new technique for the assay of infectivity of human adenovirus 5 DNA. Virology 52:456–467.
12. Graham, F. L. et al., 1977. Characteristics of a human cell line transformed by the human adenovirus type 5. J. Gen. Virol. 36:59–77.
13. Gurgo, C. et al., 1988. Envelope sequences of two new United States HIV-1 isolates. Virol. 164: 531–536.
14. Haffar, O. K. et al., 1991. The cytoplasmic tail of HIV-1 gp160 contains regions that associate with cellular membranes. Virol. 180:439–441.

15. Higuchi, R. 1990. Recombinant PCR. p.177–183. In M. A. Innis et al. (eds.), *PCR Protocols A Guide to Methods and Applications*, Academic Press, Inc., New York.
16. Ho, D. D. et al., 1991. Conformational epitope on gp120 important in CD4 binding and human immunodeficiency virus type 1 neutralization identified by a human monoclonal antibody. J. Virol. 65:489–493.
17. Kellog, D. E. et al., 1990. Detection of Human Immunodeficiency Virus, p. 337–347. In M. A. Innis et al. (eds.), *PCR Protocols A Guide to Methods and Applications*, Academic Press, Inc., New York.
18. Laemmli, U. K. 1970. Cleavage of structural proteins during the assembly of the head of bacteriophage T4. Nature 227:680–685.
19. Langedijk, J. P. M. et al., 1991. Neutralizing activity of anti-peptide antibodies against the principal neutralization domain of human immunodeficiency virus type 1. J. Gen. Virol. 72:2519–2526.
20. LaRosa, G. J. et al., 1990. Conserved sequences and structural elements in the HIV-1 principal neutralizing determinant. Science 249:932–935.
21. Lasky, L. A. et al., 1987. Delineation of a region of the human immunodeficiency virus gp120 glycoprotein critical for interaction with the CD4 receptor. Cell 50:975–985.
22. Lasky, L. A. et al., 1986. Neutralization of the AIDS retrovirus by antibodies to a recombinant envelope glycoprotein. Science 233: 209–212.
23. Matsushita, S. et al., 1988. Characterization of a human immunodeficiency virus neutralizing monoclonal antibody and mapping of a neutralizing epitope. J. Virol. 62:2107–2114.
24. McCutchan, F. E. et al., 1992. Genetic Variants of HIV-1 in Thailand. AIDS Res. and Human Retroviruses 8:1887–1895.
25. McKeating, J. et al., 1991. Recombinant CD4-selected human immunodeficiency virus type 1 variants with reduced gp120 affinity for CD4 and increased cell fusion capacity. J. Virol. 65: 4777–4785.
26. McKeating, J. A. et al., 1992. Monoclonal antibodies to the C4 region of human immunodeficiency virus type 1 gp120: use in topological analysis of a CD4 binding site. AIDS Research and Human Retroviruses. 8: 451–459.
27. McNearney, T. et al., 1992. Relationship of human immunodeficiency virus type 1 sequence heterogeneity to stage of disease. Proc. Natl. Acad. Sci. U.S.A. 89:10247–10251.
28. Modrow, S. et al., 1987. Computer-assisted analysis of envelope protein sequences of seven human immunodeficiency virus isolates: predictions of antigenic epitopes in conserved and variable regions. J. Virol. 61:570–578.
29. Moore, J. P. 1990. Simple methods for monitoring HIV-1 and HIV-2 gp120 binding to sCD4 by ELISA: HIV-1 has a 25 fold lower affinity than HIV-1 for sCD4. AIDS 3:297–305.
30. Muesing, M. A. et al., 1985. Nucleic acid structure and expression of the human AIDS/lymphadenopathy retrovirus. *Nature* 313:450–458.
31. Munson, P. J. et al. 1983. LIGAND: a computerized analysis of ligand binding data. Methods Enzymol. 92:543.
32. Myers, G. et al., 1992. Human Retroviruses and AIDS. A compilation and analysis of nucleic acid and amino acid sequences. Los Alamos National Laboratory, Los Alamos, N. Mex.
33. Nakamura, G. et al., 1992. Monoclonal antibodies to the extracellular domain of HIV-1$_{IIIB}$ gp160 that neutralize infectivity, block binding to CD4, and react with diverse isolates. AIDS and Human Retroviruses 8:1875–1885.
34. Olshevsky V. et al., 1990. Identification of individual human immunodeficiency virus type 1 gp120 amino acids important for CD4 receptor binding. J. Virol. 64:5701–5707.
35. Posner, M. R. et al., 1991. An IgG human monoclonal antibody which reacts with HIV-1/GP120, inhibits virus binding to cells and neutralizes infection. J. Immunol. 146:4325–4332.
36. Ratner, L. et al., 1987. Complete nucleotide sequences of functional clones of the AIDS virus. AIDS Res. and Human Retroviruses 3:57–69.
37. Ratner, L. et al., 1985. Complete nucleotide sequence of the AIDS virus, HTLV-III. Nature 313:277–284.
38. Reitz, M. S. Jr. et al., 1992. On the historical origins of HIV-1 (MN) and (RF). AIDS Research and Human Retroviruses 9: 1539–1541.
39. Rusche, J. R. et al., 1988. Antibodies that inhibit fusion of human immunodeficiency virus-infected cells bind to a 24-amino acid sequence of the viral envelope, gp120. Proc. Natl. Acad. Sci. USA. 85:3198–3202.
40. Scatchard, G. 1949. The attractions proteins for small molecules and ions. Ann. N. Y. Acad. Sci. 51: 660–672.
41. Schnittman, S. M. et al., 1988. Characterization of gp120 binding to CD4 and an assay that measures ability of sera to inhibit this binding. J. Immunol. 141:4181–4186.
42. Scott, C. F. Jr. et al., 1990. Human monoclonal antibody that recognizes the V3 region of human immunodeficiency virus gp120 and neutralizes the human T-lymphotropic virus type III$_{MN}$ strain. Proc. Natl. Acad. Sci. U.S.A. 87:8597–8601.
43. Sun, N. C. et al., 1989. Generation and characterization of monoclonal antibodies to the putative CD4-binding domain of human immunodeficiency virus type 1 gp120. J. Virol. 63:3579–3585.
44. Tersmette, M. R. A. et al., 1989. Evidence for a role of virulent human immunodeficiency virus (HIV) variants in the pathogenesis of AIDS obtained from studies on a panel of sequential HIV isolates. J. Virol. 63: 2118–2125.
45. Tilley, S. A. et al., 1991. A human monoclonal-antibody against the CD4-binding site of HIV-1 GP120 exhibits potent, broadly neutralizing activity. Res. Virology 142:247–259.
46. Wain Hobson, S. et al., 1985. Nucleotide sequence of the AIDS virus, LAV. Cell 40:9–17.
47. Weiss, R. A. et al., 1986. Variable and conserved neutralizing antigen of human immunodeficiency virus. Nature 324:572–575.

What is claimed is:

1. A multivalent HIV subunit gp120 immunogenic composition wherein gp120 present in the immunogenic composition is from at least two isolates and the isolates:
   a. have different reutralizing epitopes in the principal neutralizing domain of gp 120;
   b. have different neutralizing epitopes in the V2 domain of gp120 and the neutralizing epitopes are present in at least about 5% of the isolates in a geographic region; or
   c. have different neutralizing epitopes in the C4 domain of gp120 and the neutralizing epitopes are present in at least about 5% of the isolates in a geographic region.

2. The immunogenic composition of claim 1 wherein gp120 present in the immunogenic composition is from at least two HIV isolates which have different neutralizing epitopes in the V2 domain of gp120 and the neutralizing epitopes are present in at least about 5% of the isolates in a geographic region.

3. The immunogenic composition of claim 1 wherein gp120 present in the immunogenic composition is from at least two HIV isolates which have different neutralizing epitopes in the principal neutralizing domain of gp120.

4. The immunogenic composition of claim 1 wherein each isolate has a different neutralizing epitope in the C4 domain of gp120 and the neutralizing epitopes are present in at least about 5% of the isolates in a geographic region.

5. The immunogenic composition of claim 1 wherein gp120 present in the immunogenic composition is from the MN and GNE$_8$ strain of HIV.

6. The immunogenic composition of claim 5 wherein gp120 from the GNE$_{16}$ strain of HIV is also present in the immunogenic composition.

7. An improved serotyping method for HIV strains comprising determining the serotypes of the V2, V3, and C4 domains of gp120.

8. A method for making a composition that is capable of eliciting antibodies to HIV, said method comprising:
   a. determining neutralizing epitopes for one or more domains of gp120 from HIV isolates from a geographic region;
   b. selecting a plurality of HIV isolates having different neutralizing epitopes in at least one domain of gp120, wherein each of said different neutralizing epitopes is present in at least about 5 percent of isolates in the geographic region; and
   b. selecting a plurality of HIV isolates having different neutralizing epitopes in at least one domain of gp120, wherein each of said different neutralizing epitopes is present in at least about 5 percent of isolates in the geographic region; and
   c. making a composition capable of eliciting antibodies that bind to said different neutralizing epitopes.

9. The method of claim 8 wherein the composition comprises gp120 or a fragment thereof.

10. The method of claim 8 wherein the composition comprises DNA capable of expressing gp 120 or fragment thereof.

11. The method claim 8 wherein at least one of said different neutralizing epitopes is present in at least about 20 percent of isolates in the geographic region.

12. The method of claim 11 wherein at least one of said different neutralizing epitopes is present in at least about 40 percent of isolates in the geographic region.

13. The method of claim 8 wherein said plurality of different neutralizing epitopes constitutes at least about 50 percent of the epitopes for said domain of gp120 in the isolates in said geographic region.

14. The method of claim 13 wherein said plurality of different neutralizing epitopes constitutes at least about 70 percent the epitopes for said domain of gp120 in the isolates in said geographic region.

15. The method of claim 14 wherein said plurality of different neutralizing epitopes constitutes at least about 90 percent of the epitopes for said domain of gp120 in the isolates in said geographic region.

16. The immunogenic composition of claim 1 wherein the combination of different neutralizing epitopes constitutes at least about 50% of the population of a selected geographic region.

17. A multivalent HIV gp120 subunit immunogenic composition wherein gp120 present in the immunogenic composition is from at least two HIV isolates that have different amino acid residues at a position selected from 171, 173 and 429, as numbered from the N-terminal methionine of gp120 from the MN strain of HIV.

18. The immunogenic composition of claim 1 wherein gp120 present in the immunogenic composition is from the MN and A244 (Thai) strains of HIV.

19. The immunogenic composition of claim 1 wherein at least one of said HIV strains is a primary isolate.

20. An HIV gp120 subunit immunogenic composition comprising an isolated $MN_{GNE}$-gp120 polypeptide comprising the $MN_{GNE}$-gp120 amino acid sequence designated SEQ ID NO:1.

21. An HIV gp120 subunit immunogenic composition comprising a polypeptide comprising a truncated gp120 sequence comprising the V2, V3, and C4 domains of gp120, which sequence is from a gp120 polypeptide selected from the group consisting of $MN_{GNE}$-gp120, $GNE_8$-gp120, and $GNE_{16}$-gp120, wherein said polypeptide lacks the gp120 signal sequence.

22. The immunogenic composition of claim 21, wherein the truncated gp120 sequence is joined to a heterologous signal sequence.

23. The immunogenic composition of claim 22, wherein the heterologous signal sequence is joined to amino acid residue 41 of said truncated gp120 sequence, as numbered from the N-terminal methionine of gp120 from the MN strain of HIV.

24. The immunogenic composition of claim 22, wherein the heterologous signal sequence is derived from the herpes simplex glycoprotein gD1.

25. The immunogenic composition of claim 24, wherein the heterologous signal sequence is joined to amino acid residue 41 of said truncated gp120, as numbered from the N-terminal methionine of gp120 from the MN strain of HIV.

26. The immunogenic composition of claim 25, wherein the heterologous signal sequence is joined to amino acid residue 41 of said truncated gp120 via a sequence derived from the herpes simplex glycoprotein gD-1.

27. The immunogenic composition of claim 21, wherein the truncated gp120 sequence is joined to a heterologous sequence derived from the herpes simplex glycoprotein gD-1.

28. A composition comprising DNA that expresses gp120, or a fragment thereof, that is capable of eliciting antibodies to HIV, wherein the gp120 is from at least two isolates and the isolates:

a. have different neutralizing epitopes in the principal neutralizing domain of gp120;

b. have different neutralizing epitopes in the V2 domain of gp120 and the neutralizing epitopes are present in at least about 5% of the isolates in a geographic region; or c. have different neutralizing epitopes in the C4 domain of gp120 and the neutralizing epitopes are present in at least about 5% of the isolates in a geographic region.

29. The composition of claim 28 wherein the at least two HIV isolates have different neutralizing epitopes in the V2 domain of gp120 and the neutralizing epitopes are present in at least about 5% of the isolates in a geographic region.

30. The composition of claim 28 wherein the at least two HIV isolates have different neutralizing epitopes in the principal neutralizing domain of gp120.

31. The composition of claim 28 wherein the at least two HIV isolates have different neutralizing epitopes in the C4 domain of gp120 and the neutralizing epitopes are present in at least about 5% of the isolates in a geographic region.

32. The composition of claim 28 wherein the at least two HIV isolates are the MN and $GNE_8$ strains of HIV.

33. The composition of claim 32 wherein DNA capable of expressing gp120, or a fragment thereof, from the $GNE_{16}$ strain of HIV is also present in the composition.

34. The composition of claim 28 wherein the combination of different neutralizing epitopes constitutes at least about 50% of the population of a selected geographic region.

35. A composition comprising DNA that expresses gp120, or a fragment thereof, that is capable of eliciting antibodies to HIV, wherein the gp120 is from at least two HIV isolates that have different amino acid residues at a position selected from 171, 173 and 429, as numbered from the N-terminal methionine of gp120 from the MN strain of HIV.

36. The composition of claim 28 wherein the at least two HIV isolates are the MN and A244 (Thai) strains of HIV.

37. The immunogenic composition of claim 28 wherein at least one of said at least two HIV strains is a primary isolate.

38. A composition comprising DNA that expresses a $MN_{GNE}$-gp120 polypeptide comprising the $MN_{GNE}$-gp120 amino acid sequence designated SEQ ID NO:1.

39. A composition comprising DNA that expresses a polypeptide comprising a truncated gp120 sequence comprising the V2, V3, and C4 domains of gp120, which sequence is from a gp120polypeptide selected from the group consisting of $MN_{GNE}$-gp120, $GNE_8$-gp120, and $GNE_{16}$-gp120, wherein said polypeptide lacks the gp120 signal sequence.

40. The composition of claim 39, wherein the truncated gp120 sequence is joined to a heterologous signal sequence.

41. The composition of claim 40, wherein the heterologous signal sequence is joined to amino acid residue 41 of said truncated gp120 sequence, as numbered from the N-terminal methionine of gp120 from the MN strain of HIV.

42. The composition of claim 40, wherein the heterologous signal sequence is derived from the herpes simplex glycoprotein gD1.

43. The composition of claim 42, wherein the heterologous signal sequence is joined to amino acid residue 41 of said truncated gp120, as numbered from the N-terminal methionine of gp120 from the MN strain of HIV.

44. The composition of claim 43, wherein the heterologous signal sequence is joined to amino acid residue 41 of said truncated gp120 via a sequence derived from the herpes simplex glycoprotein gD-1.

45. The composition of claim 39, wherein the truncated gp120 sequence is joined to a heterologous sequence derived from the herpes simplex glycoprotein gD-1.

* * * * *

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
       (A) LENGTH: 511 amino acids
       (B) TYPE: amino acid
       (C) STRANDEDNESS: single
       (D) TOPOLOGY: linear (xi) SEQUENCE DESCRIPTION: SEQ ID NO: 1:

```
Met Arg Val Lys Gly Ile Arg Arg Asn Tyr Gln His Trp Trp Gly Arg
1               5                   10                  15

Gly Thr Met Leu Leu Gly Leu Leu Met Ile Cys Ser Ala Thr Glu Lys
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Ala
        50                  55                  60

His Asn Val Trp Ala Thr His Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Arg Asn Thr Thr Asn Thr Asn Asn Ser Thr Asp
130                 135                 140

Asn Asn Asn Ser Lys Ser Glu Gly Thr Ile Lys Gly Gly Glu Met Lys
145                 150                 155                 160

Asn Cys Ser Phe Asn Ile Thr Thr Ser Ile Gly Asp Lys Met Gln Lys
                165                 170                 175

Glu Tyr Ala Leu Leu Tyr Lys Leu Asp Ile Glu Pro Ile Asp Asn Asp
            180                 185                 190

Ser Thr Ser Tyr Arg Leu Ile Ser Cys Asn Thr Ser Val Ile Thr Gln
            195                 200                 205

Ala Cys Pro Lys Ile Ser Phe Glu Pro Ile Pro Ile His Tyr Cys Ala
        210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asp Phe Thr Asp Asn Ala Lys Thr
            275                 280                 285

Ile Ile Val His Leu Lys Glu Ser Val Gln Ile Asn Cys Thr Arg Pro
        290                 295                 300

Asn Tyr Asn Lys Arg Lys Arg Ile His Ile Gly Pro Gly Arg Ala Phe
305                 310                 315                 320

Tyr Thr Thr Lys Asn Ile Lys Gly Thr Ile Arg Gln Ala His Cys Ile
```

-continued

```
                325                 330                 335
Ile Ser Arg Ala Lys Trp Asn Asp Thr Leu Arg Gln Ile Val Ser Lys
            340                 345                 350

Leu Lys Glu Gln Phe Lys Asn Lys Thr Ile Val Phe Asn Pro Ser Ser
            355                 360                 365

Gly Gly Asp Pro Glu Ile Val Met His Ser Phe Asn Cys Gly Gly Glu
            370                 375                 380

Phe Phe Tyr Cys Asn Thr Ser Pro Leu Phe Asn Ser Ile Trp Asn Gly
385                 390                 395                 400

Asn Asn Thr Trp Asn Asn Thr Thr Gly Ser Asn Asn Ile Thr Leu
            405                 410                 415

Gln Cys Lys Ile Lys Gln Ile Ile Asn Met Trp Gln Lys Val Gly Lys
            420                 425                 430

Ala Met Tyr Ala Pro Pro Ile Glu Gly Gln Ile Arg Cys Ser Ser Asn
            435                 440                 445

Ile Thr Gly Leu Leu Thr Arg Asp Gly Gly Glu Asp Thr Asp Thr
            450                 455                 460

Asn Asp Thr Glu Ile Phe Arg Pro Gly Gly Gly Asp Met Arg Asp Asn
465                 470                 475                 480

Trp Arg Ser Glu Leu Tyr Lys Tyr Lys Val Val Thr Ile Glu Pro Leu
            485                 490                 495

Gly Val Ala Pro Thr Lys Ala Lys Arg Arg Val Val Gln Arg Glu
            500                 505                 510

(2) INFORMATION FOR SEQ ID NO: 2:

(i) SEQUENCE CHARACTERISTICS:
        (A) LENGTH: 501 amino acids
        (B) TYPE: amino acid
        (C) STRANDEDNESS: single
        (D) TOPOLOGY: linear (xi) SEQUENCE DESCRIPTION: SEQ ID NO: 2:

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Leu Glu Val Pro
            20                  25                  30

Val Trp Lys Glu Ala Thr Thr Thr Leu Phe Cys Ala Ser Asp Ala Lys
            35                  40                  45

Ala Tyr Asp Thr Glu Ala His Asn Val Trp Ala Thr His Ala Cys Val
            50                  55                  60

Pro Thr Asp Pro Asn Pro Gln Glu Val Glu Leu Val Asn Val Thr Glu
65                  70                  75                  80

Asn Phe Asn Met Trp Lys Asn Asn Met Val Glu Gln Met His Glu Asp
            85                  90                  95

Ile Ile Ser Leu Trp Asp Gln Ser Leu Lys Pro Cys Val Lys Leu Thr
            100                 105                 110

Pro Leu Cys Val Thr Leu Asn Cys Thr Asp Leu Arg Asn Thr Thr Asn
            115                 120                 125

Thr Asn Asn Ser Thr Asp Asn Asn Ser Lys Ser Glu Gly Thr Ile
            130                 135                 140

Lys Gly Gly Glu Met Lys Asn Cys Ser Phe Asn Ile Thr Thr Ser Ile
145                 150                 155                 160

Gly Asp Lys Met Gln Lys Glu Tyr Ala Leu Leu Tyr Lys Leu Asp Ile
            165                 170                 175
```

```
Glu Pro Ile Asp Asn Asp Ser Thr Ser Tyr Arg Leu Ile Ser Cys Asn
            180                 185                 190

Thr Ser Val Ile Thr Gln Ala Cys Pro Lys Ile Ser Phe Glu Pro Ile
        195                 200                 205

Pro Ile His Tyr Cys Ala Pro Ala Gly Phe Ala Ile Leu Lys Cys Asn
    210                 215                 220

Asp Lys Lys Phe Ser Gly Lys Gly Ser Cys Lys Asn Val Ser Thr Val
225                 230                 235                 240

Gln Cys Thr His Gly Ile Arg Pro Val Val Ser Thr Gln Leu Leu Leu
            245                 250                 255

Asn Gly Ser Leu Ala Glu Glu Glu Val Val Ile Arg Ser Glu Asp Phe
            260                 265                 270

Thr Asp Asn Ala Lys Thr Ile Ile Val His Leu Lys Glu Ser Val Gln
            275                 280                 285

Ile Asn Cys Thr Arg Pro Asn Tyr Asn Lys Arg Lys Arg Ile His Ile
            290                 295                 300

Gly Pro Gly Arg Ala Phe Tyr Thr Thr Lys Asn Ile Lys Gly Thr Ile
305                 310                 315                 320

Arg Gln Ala His Cys Ile Ile Ser Arg Ala Lys Trp Asn Asp Thr Leu
            325                 330                 335

Arg Gln Ile Val Ser Lys Leu Lys Glu Gln Phe Lys Asn Lys Thr Ile
            340                 345                 350

Val Phe Asn Pro Ser Ser Gly Gly Asp Pro Glu Ile Val Met His Ser
            355                 360                 365

Phe Asn Cys Gly Gly Glu Phe Phe Tyr Cys Asn Thr Ser Pro Leu Phe
            370                 375                 380

Asn Ser Ile Trp Asn Gly Asn Asn Thr Trp Asn Asn Thr Thr Gly Ser
385                 390                 395                 400

Asn Asn Asn Ile Thr Leu Gln Cys Lys Ile Lys Gln Ile Ile Asn Met
                405                 410                 415

Trp Gln Lys Val Gly Lys Ala Met Tyr Ala Pro Pro Ile Glu Gly Gln
            420                 425                 430

Ile Arg Cys Ser Ser Asn Ile Thr Gly Leu Leu Leu Thr Arg Asp Gly
            435                 440                 445

Gly Glu Asp Thr Asp Thr Asn Asp Thr Glu Ile Phe Arg Pro Gly Gly
450                 455                 460

Gly Asp Met Arg Asp Asn Trp Arg Ser Glu Leu Tyr Lys Tyr Lys Val
465                 470                 475                 480

Val Thr Ile Glu Pro Leu Gly Val Ala Pro Thr Lys Ala Lys Arg Arg
            485                 490                 495

Val Val Gln Arg Glu
            500

(2) INFORMATION FOR SEQ ID NO: 3:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 3:

Cys Lys Ile Lys Gln Ile Ile Asn Met Trp Gln Lys Val Gly Lys Ala
1               5                   10                  15

Met Tyr Ala Pro Pro Ile Glu Gly Gln Ile Arg Cys
            20                  25
```

(2) INFORMATION FOR SEQ ID NO: 4:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 4:

```
Cys Arg Ile Lys Gln Phe Ile Asn Met Trp Gln Glu Val Gly Lys Ala
 1               5                  10                  15

Met Tyr Ala Pro Pro Ile Ser Gly Gln Ile Arg Cys
             20                  25
```

(2) INFORMATION FOR SEQ ID NO: 5:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 5:

```
Cys Arg Ile Lys Gln Ile Ile Asn Met Trp Gln Glu Val Gly Lys Ala
 1               5                  10                  15

Met Tyr Ala Pro Pro Ile Lys Gly Gln Ile Arg Cys
             20                  25
```

(2) INFORMATION FOR SEQ ID NO: 6:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 6:

```
Cys Arg Ile Lys Gln Ile Ile Asn Met Trp Gln Gly Val Gly Lys Ala
 1               5                  10                  15

Met Tyr Ala Pro Pro Ile Glu Gly Gln Ile Asn Cys
             20                  25
```

(2) INFORMATION FOR SEQ ID NO: 7:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 7:

```
Cys Arg Ile Lys Gln Ile Ile Asn Arg Trp Gln Glu Val Gly Lys Ala
 1               5                  10                  15

Ile Tyr Ala Pro Pro Ile Ser Gly Gln Ile Arg Cys
             20                  25
```

(2) INFORMATION FOR SEQ ID NO: 8:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 8:

```
Cys Arg Ile Lys Gln Ile Val Asn Met Trp Gln Arg Val Gly Gln Ala
1               5                   10                  15

Met Tyr Ala Pro Pro Ile Lys Gly Val Ile Lys Cys
            20                  25
```

(2) INFORMATION FOR SEQ ID NO: 9:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 9:

```
Cys Lys Ile Lys Gln Ile Ile Asn Met Trp Gln Gly Ala Gly Gln Ala
1               5                   10                  15

Met Tyr Ala Pro Pro Ile Ser Gly Thr Ile Asn Cys
            20                  25
```

(2) INFORMATION FOR SEQ ID NO: 10:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 10:

```
Cys Arg Ile Lys Gln Phe Ile Asn Met Trp Gln Glu Val Gly Lys Ala
1               5                   10                  15

Met Tyr Ala Pro Pro Ile Ser Gly Gln Ile Arg Cys
            20                  25
```

(2) INFORMATION FOR SEQ ID NO: 11:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 11:

```
Cys Lys Ile Lys Gln Ile Ile Asn Met Trp Gln Lys Val Gly Lys Ala
1               5                   10                  15

Met Tyr Ala Pro Pro Ile Ser Gly Gln Ile Arg Cys
            20                  25
```

(2) INFORMATION FOR SEQ ID NO: 12:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 12:

```
Cys Arg Ile Lys Gln Ile Ile Asn Met Trp Gln Glu Val Gly Lys Ala
1               5                   10                  15

Met Tyr Ala Pro Pro Ile Ser Gly Gln Ile Arg Cys
            20                  25
```

(2) INFORMATION FOR SEQ ID NO: 13:

(i) SEQUENCE CHARACTERISTICS:

(A) LENGTH: 28 amino acids
(B) TYPE: amino acid
(C) STRANDEDNESS: single
(D) TOPOLOGY: linear (xi) SEQUENCE DESCRIPTION: SEQ ID NO: 13:

Cys Lys Ile Lys Gln Ile Ile Asn Met Trp Gln Glu Val Gly Lys Ala
1               5                   10                  15

Met Tyr Ala Pro Pro Ile Glu Gly Gln Ile Arg Cys
            20                  25

(2) INFORMATION FOR SEQ ID NO: 14:

(i) SEQUENCE CHARACTERISTICS:
       (A) LENGTH: 92 amino acids
       (B) TYPE: amino acid
       (C) STRANDEDNESS: single
       (D) TOPOLOGY: linear (xi) SEQUENCE DESCRIPTION: SEQ ID NO: 14:

Ser Gly Gly Asp Pro Glu Ile Val Met His Ser Phe Asn Cys Gly Gly
1               5                   10                  15

Glu Phe Phe Tyr Cys Asn Thr Ser Pro Leu Phe Asn Ser Ile Trp Asn
                20                  25                  30

Gly Asn Asn Thr Trp Asn Asn Thr Thr Gly Ser Asn Asn Asn Ile Thr
            35                  40                  45

Leu Gln Cys Lys Ile Lys Gln Ile Ile Asn Met Trp Gln Lys Val Gly
        50                  55                  60

Lys Ala Met Tyr Ala Pro Pro Ile Glu Gly Gln Ile Arg Cys Ser Ser
65                  70                  75                  80

Asn Ile Thr Gly Leu Leu Leu Thr Arg Asp Gly Gly
                85                  90

(2) INFORMATION FOR SEQ ID NO: 15:

(i) SEQUENCE CHARACTERISTICS:
       (A) LENGTH: 28 amino acids
       (B) TYPE: amino acid
       (C) STRANDEDNESS: single
       (D) TOPOLOGY: linear (xi) SEQUENCE DESCRIPTION: SEQ ID NO: 15:

Cys Lys Ile Lys Gln Ile Ile Asn Met Trp Gln Glu Val Gly Lys Ala
1               5                   10                  15

Met Tyr Ala Pro Pro Ile Glu Gly Gln Ile Arg Cys
            20                  25

(2) INFORMATION FOR SEQ ID NO: 16:

(i) SEQUENCE CHARACTERISTICS:
       (A) LENGTH: 28 amino acids
       (B) TYPE: amino acid
       (C) STRANDEDNESS: single
       (D) TOPOLOGY: linear (xi) SEQUENCE DESCRIPTION: SEQ ID NO: 16:

Cys Lys Ile Lys Gln Ile Ile Asn Met Trp Gln Ala Val Gly Lys Ala
1               5                   10                  15

Met Tyr Ala Pro Pro Ile Glu Gly Gln Ile Arg Cys
            20                  25

(2) INFORMATION FOR SEQ ID NO: 17:

(i) SEQUENCE CHARACTERISTICS:
    (A) LENGTH: 28 amino acids
    (B) TYPE: amino acid
    (C) STRANDEDNESS: single
    (D) TOPOLOGY: linear (xi) SEQUENCE DESCRIPTION: SEQ ID NO: 17:

Cys Ala Ile Lys Gln Ile Ile Asn Met Trp Gln Lys Val Gly Lys Ala
1               5                   10                  15

Met Tyr Ala Pro Pro Ile Glu Gly Gln Ile Arg Cys
            20                  25

(2) INFORMATION FOR SEQ ID NO: 18:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 18:

Cys Lys Ile Ala Gln Ile Ile Asn Met Trp Gln Lys Val Gly Lys Ala
1               5                   10                  15

Met Tyr Ala Pro Pro Ile Glu Gly Gln Ile Arg Cys
            20                  25

(2) INFORMATION FOR SEQ ID NO: 19:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 19:

Cys Lys Ile Lys Gln Ile Ile Asn Met Trp Gln Lys Val Gly Ala Ala
1               5                   10                  15

Met Tyr Ala Pro Pro Ile Glu Gly Gln Ile Arg Cys
            20                  25

(2) INFORMATION FOR SEQ ID NO: 20:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 20:

Cys Lys Ile Lys Gln Ile Ile Asn Met Trp Gln Lys Val Gly Lys Ala
1               5                   10                  15

Met Tyr Ala Pro Pro Ile Ala Gly Gln Ile Arg Cys
            20                  25

(2) INFORMATION FOR SEQ ID NO: 21:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 21:

Cys Arg Ile Lys Gln Phe Ile Asn Met Trp Gln Glu Val Gly Lys Ala
1               5                   10                  15

```
Met Tyr Ala Pro Pro Ile Ser Gly Gln Ile Arg Cys
            20                  25
```

(2) INFORMATION FOR SEQ ID NO: 22:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 22:

```
Cys Lys Ile Lys Gln Phe Ile Asn Met Trp Gln Lys Val Gly Lys Ala
 1               5                  10                  15
Met Tyr Ala Pro Pro Ile Glu Gly Gln Ile Arg Cys
            20                  25
```

(2) INFORMATION FOR SEQ ID NO: 23:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 23:

```
Cys Lys Ile Lys Gln Phe Ile Asn Met Trp Gln Glu Val Gly Lys Ala
 1               5                  10                  15
Met Tyr Ala Pro Pro Ile Glu Gly Gln Ile Arg Cys
            20                  25
```

(2) INFORMATION FOR SEQ ID NO: 24:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 24:

```
Phe Ile Asn Met Trp Gln Glu Val Gly Lys Ala Met Tyr Ala Pro Pro
 1               5                  10                  15
Ile Ser
```

(2) INFORMATION FOR SEQ ID NO: 25:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 25:

```
Met Trp Gln Glu Val Gly Lys Ala Met Tyr Ala Pro
 1               5                  10
```

(2) INFORMATION FOR SEQ ID NO: 26:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 26:

```
Gly Lys Ala Met Tyr Ala Pro Pro Ile Lys Gly Gln Ile Arg
```

(2) INFORMATION FOR SEQ ID NO: 27:

(i) SEQUENCE CHARACTERISTICS:
        (A) LENGTH: 2552 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2552

(xi) SEQUENCE DESCRIPTION: SEQ ID NO: 27:

```
ATG ATA GTG AAG GGG ATC AGG AAG AAT TGT CAG CAC TTG TGG AGA TGG       48
Met Ile Val Lys Gly Ile Arg Lys Asn Cys Gln His Leu Trp Arg Trp
 1               5                  10                  15

GGC ACC ATG CTC CTT GGG ATG TTG ATG ATC TGT AGT GCT GCA GAA AAA       96
Gly Thr Met Leu Leu Gly Met Leu Met Ile Cys Ser Ala Ala Glu Lys
             20                  25                  30

TTG TGG GTC ACA GTC TAT TAT GGG GTA CCT GTG TGG AAA GAA GCA ACC      144
Leu Trp Val Thr Val Tyr Tyr Gly Val Pro Val Trp Lys Glu Ala Thr
         35                  40                  45

ACC ACT CTA TTT TGT GCA TCA GAT GCT AAA GCA TAT GAT ACA GAG GTA      192
Thr Thr Leu Phe Cys Ala Ser Asp Ala Lys Ala Tyr Asp Thr Glu Val
     50                  55                  60

CAT AAT GTT TGG GCC ACA CAT GCC TGT GTA CCC ACA GAC CCC AAC CCA      240
His Asn Val Trp Ala Thr His Ala Cys Val Pro Thr Asp Pro Asn Pro
 65                  70                  75                  80

CAA GAA ATA GGA TTG GAA AAT GTA ACA GAA AAT TTT AAC ATG TGG AAA      288
Gln Glu Ile Gly Leu Glu Asn Val Thr Glu Asn Phe Asn Met Trp Lys
                 85                  90                  95

AAT AAC ATG GTA GAA CAG ATG CAT GAG GAT ATA ATC AGT TTA TGG GAT      336
Asn Asn Met Val Glu Gln Met His Glu Asp Ile Ile Ser Leu Trp Asp
            100                 105                 110

CAA AGC TTA AAG CCA TGT GTA AAA TTA ACC CCA CTA TGT GTT ACT TTA      384
Gln Ser Leu Lys Pro Cys Val Lys Leu Thr Pro Leu Cys Val Thr Leu
        115                 120                 125

AAT TGC ACT GAT TTG AAA AAT GCT ACT AAT ACC ACT AGT AGC AGC TGG      432
Asn Cys Thr Asp Leu Lys Asn Ala Thr Asn Thr Thr Ser Ser Ser Trp
    130                 135                 140

GGA AAG ATG GAG AGA GGA GAA ATA AAA AAC TGC TCT TTC AAT GTC ACC      480
Gly Lys Met Glu Arg Gly Glu Ile Lys Asn Cys Ser Phe Asn Val Thr
145                 150                 155                 160

ACA AGT ATA AGA GAT AAG ATG AAG AAT GAA TAT GCA CTT TTT TAT AAA      528
Thr Ser Ile Arg Asp Lys Met Lys Asn Glu Tyr Ala Leu Phe Tyr Lys
                165                 170                 175

CTT GAT GTA GTA CCA ATA GAT AAT GAT AAT ACT AGC TAT AGG TTG ATA      576
Leu Asp Val Val Pro Ile Asp Asn Asp Asn Thr Ser Tyr Arg Leu Ile
            180                 185                 190

AGT TGT AAC ACC TCA GTC ATT ACA CAG GCC TGT CCA AAG GTG TCC TTT      624
Ser Cys Asn Thr Ser Val Ile Thr Gln Ala Cys Pro Lys Val Ser Phe
        195                 200                 205

GAG CCA ATT CCC ATA CAT TAT TGT GCC CCG GCT GGT TTT GCG ATT CTA      672
Glu Pro Ile Pro Ile His Tyr Cys Ala Pro Ala Gly Phe Ala Ile Leu
    210                 215                 220

AAG TGT AGA GAT AAA AAG TTC AAT GGA ACA GGA CCA TGT ACA AAT GTC      720
Lys Cys Arg Asp Lys Lys Phe Asn Gly Thr Gly Pro Cys Thr Asn Val
225                 230                 235                 240
```

```
AGC ACA GTA CAA TGT ACA CAT GGA ATT AGG CCA GTA GTA TCA ACT CAA        768
Ser Thr Val Gln Cys Thr His Gly Ile Arg Pro Val Val Ser Thr Gln
            245                 250                 255

CTG CTG TTA AAT GGC AGT TTA GCA GAA GAA GAA GTA GTA ATT AGA TCT        816
Leu Leu Leu Asn Gly Ser Leu Ala Glu Glu Glu Val Val Ile Arg Ser
                260                 265                 270

GCC AAT TTC TCG GAC AAT GCT AAA ACC ATA ATA GTA CAG CTG AAC GAA        864
Ala Asn Phe Ser Asp Asn Ala Lys Thr Ile Ile Val Gln Leu Asn Glu
                    275                 280                 285

TCT GTA GAA ATT AAT TGT ACA AGA CCC AAC AAC AAT ACA AGA AGA AGT        912
Ser Val Glu Ile Asn Cys Thr Arg Pro Asn Asn Asn Thr Arg Arg Ser
        290                 295                 300

ATA CAT ATA GGA CCA GGG AGA GCA TTT TAT GCA ACA GGA GAA ATA ATA        960
Ile His Ile Gly Pro Gly Arg Ala Phe Tyr Ala Thr Gly Glu Ile Ile
305                 310                 315                 320

GGA GAC ATA AGA CAA GCA CAT TGT AAC CTT AGT AGC ACA AAA TGG AAT       1008
Gly Asp Ile Arg Gln Ala His Cys Asn Leu Ser Ser Thr Lys Trp Asn
                325                 330                 335

AAT ACT TTA AAA CAG ATA GTT ACA AAA TTA AGA GAA CAT TTT AAT AAA       1056
Asn Thr Leu Lys Gln Ile Val Thr Lys Leu Arg Glu His Phe Asn Lys
                    340                 345                 350

ACA ATA GTC TTT AAT CAC TCC TCA GGA GGG GAC CCA GAA ATT GTA ATG       1104
Thr Ile Val Phe Asn His Ser Ser Gly Gly Asp Pro Glu Ile Val Met
        355                 360                 365

CAC AGT TTT AAT TGT GGA GGG GAA TTT TTC TAC TGT AAT ACA ACA CCA       1152
His Ser Phe Asn Cys Gly Gly Glu Phe Phe Tyr Cys Asn Thr Thr Pro
            370                 375                 380

CTG TTT AAT AGT ACT TGG AAT TAT ACT TAT ACT TGG AAT AAT ACT GAA       1200
Leu Phe Asn Ser Thr Trp Asn Tyr Thr Tyr Thr Trp Asn Asn Thr Glu
385                 390                 395                 400

GGG TCA AAT GAC ACT GGA AGA AAT ATC ACA CTC CAA TGC AGA ATA AAA       1248
Gly Ser Asn Asp Thr Gly Arg Asn Ile Thr Leu Gln Cys Arg Ile Lys
                405                 410                 415

CAA ATT ATA AAC ATG TGG CAG GAA GTA GGA AAA GCA ATG TAT GCC CCT       1296
Gln Ile Ile Asn Met Trp Gln Glu Val Gly Lys Ala Met Tyr Ala Pro
                    420                 425                 430

CCC ATA AGA GGA CAA ATT AGA TGC TCA TCA AAT ATT ACA GGG CTG CTA       1344
Pro Ile Arg Gly Gln Ile Arg Cys Ser Ser Asn Ile Thr Gly Leu Leu
        435                 440                 445

TTA ACA AGA GAT GGT GGT AAT AAC AGC GAA ACC GAG ATC TTC AGA CCT       1392
Leu Thr Arg Asp Gly Gly Asn Asn Ser Glu Thr Glu Ile Phe Arg Pro
            450                 455                 460

GGA GGA GGA GAT ATG AGG GAC AAT TGG AGA AGT GAA TTA TAT AAA TAT       1440
Gly Gly Gly Asp Met Arg Asp Asn Trp Arg Ser Glu Leu Tyr Lys Tyr
465                 470                 475                 480

AAA GTA GTA AAA ATT GAA CCA TTA GGA GTA GCA CCC ACC AAG GCA AAG       1488
Lys Val Val Lys Ile Glu Pro Leu Gly Val Ala Pro Thr Lys Ala Lys
                485                 490                 495

AGA AGA GTG ATG CAG AGA GAA AAA AGA GCA GTG GGA ATA GGA GCT GTG       1536
Arg Arg Val Met Gln Arg Glu Lys Arg Ala Val Gly Ile Gly Ala Val
                    500                 505                 510

TTC CTT GGG TTC TTG GGA GCA GCA GGA AGC ACT ATG GGC GCA GCG TCA       1584
Phe Leu Gly Phe Leu Gly Ala Ala Gly Ser Thr Met Gly Ala Ala Ser
        515                 520                 525

GTG ACG CTG ACG GTA CAG GCC AGA CTA TTA TTG TCT GGT ATA GTG CAA       1632
Val Thr Leu Thr Val Gln Ala Arg Leu Leu Leu Ser Gly Ile Val Gln
            530                 535                 540

CAG CAG AAC AAT TTG CTG AGG GCT ATT GAG GCC GAA CAG CAT CTG TTG       1680
Gln Gln Asn Asn Leu Leu Arg Ala Ile Glu Ala Glu Gln His Leu Leu
545                 550                 555                 560
```

```
CAA CTC ACA GTC TGG GGC ATC AAG CAG CTC CAG GCA AGA GTC CTG GCT      1728
Gln Leu Thr Val Trp Gly Ile Lys Gln Leu Gln Ala Arg Val Leu Ala
              565                 570                 575

GTG GAG AGA TAC CTA AAG GAT CAA CAG CTC CTG GGG ATT TGG GGT TGC      1776
Val Glu Arg Tyr Leu Lys Asp Gln Gln Leu Leu Gly Ile Trp Gly Cys
          580                 585                 590

TCT GGA AAA CTC ATC TGC ACC ACT GCT GTG CCT TGG AAT GCT AGT TGG      1824
Ser Gly Lys Leu Ile Cys Thr Thr Ala Val Pro Trp Asn Ala Ser Trp
      595                 600                 605

AGT AAT AAA TCT CTG GAT AAG ATT TGG GAT AAC ATG ACC TGG ATG GAG      1872
Ser Asn Lys Ser Leu Asp Lys Ile Trp Asp Asn Met Thr Trp Met Glu
  610                 615                 620

TGG GAA AGA GAA ATT GAC AAT TAC ACA AGC TTA ATA TAC AGC TTA ATT      1920
Trp Glu Arg Glu Ile Asp Asn Tyr Thr Ser Leu Ile Tyr Ser Leu Ile
625                 630                 635                 640

GAA GAA TCG CAG AAC CAA CAA GAA AAA AAT GAA CAA GAA TTA TTG GAA      1968
Glu Glu Ser Gln Asn Gln Gln Glu Lys Asn Glu Gln Glu Leu Leu Glu
              645                 650                 655

TTA GAT AAA TGG GCA AGT TTG TGG AAT TGG TTT GAC ATA ACA AAA TGG      2016
Leu Asp Lys Trp Ala Ser Leu Trp Asn Trp Phe Asp Ile Thr Lys Trp
          660                 665                 670

CTG TGG TAT ATA AAA ATA TTC ATA ATG ATA GTA GGA GGC TTG GTA GGT      2064
Leu Trp Tyr Ile Lys Ile Phe Ile Met Ile Val Gly Gly Leu Val Gly
      675                 680                 685

TTA AGA ATA GTT TTT ACT GTA CTT TCT ATA GTG AAT AGA GTT AGG AAG      2112
Leu Arg Ile Val Phe Thr Val Leu Ser Ile Val Asn Arg Val Arg Lys
  690                 695                 700

GGA TAC TCA CCA TTA TCG TTC CAG ACC CAC CTC CCA GCC CCG AGG GGA      2160
Gly Tyr Ser Pro Leu Ser Phe Gln Thr His Leu Pro Ala Pro Arg Gly
705                 710                 715                 720

CTC GAC AGG CCC GAA GGA ACC GAA GAA GAA GGT GGA GAG CGA GAC AGA      2208
Leu Asp Arg Pro Glu Gly Thr Glu Glu Glu Gly Gly Glu Arg Asp Arg
              725                 730                 735

GAC AGA TCC AGT CGA TTA GTG GAT GGA TTC TTA GCA ATT GTC TGG GTC      2256
Asp Arg Ser Ser Arg Leu Val Asp Gly Phe Leu Ala Ile Val Trp Val
          740                 745                 750

GAC CTG CGG AGC CTG TGC CTC TTC AGC TAC CAC CGC TTG AGA GAC TTA      2304
Asp Leu Arg Ser Leu Cys Leu Phe Ser Tyr His Arg Leu Arg Asp Leu
      755                 760                 765

CTC TTG ATT GCA GCG AGG ATT GTG GAA CTT CTG GGA CGC AGG GGG TGG      2352
Leu Leu Ile Ala Ala Arg Ile Val Glu Leu Leu Gly Arg Arg Gly Trp
  770                 775                 780

GAA GCC CTC AAA TAT TGG TGG AAT CTC CTA CAG TAT TGG ATT CAG GAA      2400
Glu Ala Leu Lys Tyr Trp Trp Asn Leu Leu Gln Tyr Trp Ile Gln Glu
785                 790                 795                 800

CTA AAG AAT AGT GCT GTT AGC TTG CTC AAT GCC ACA GCC ATA GCA GTA      2448
Leu Lys Asn Ser Ala Val Ser Leu Leu Asn Ala Thr Ala Ile Ala Val
              805                 810                 815

GCT GAG GGA ACA GAT AGG GTT ATA GAA ATA GTA CAA AGA GCT TAT AGA      2496
Ala Glu Gly Thr Asp Arg Val Ile Glu Ile Val Gln Arg Ala Tyr Arg
          820                 825                 830

GCT ATT CTC CAC ATA CCC ACA CGA ATA AGA CAG GGC TTG GAA AGG GCT      2544
Ala Ile Leu His Ile Pro Thr Arg Ile Arg Gln Gly Leu Glu Arg Ala
      835                 840                 845

TTG CTA TA                                                            2552
Leu Leu
    850

(2) INFORMATION FOR SEQ ID NO: 28:
```

(i) SEQUENCE CHARACTERISTICS:
    (A) LENGTH: 850 amino acids
    (B) TYPE: amino acid
    (C) STRANDEDNESS: single
    (D) TOPOLOGY: linear (xi) SEQUENCE DESCRIPTION: SEQ ID NO: 28:

Met Ile Val Lys Gly Ile Arg Lys Asn Cys Gln His Leu Trp Arg Trp
1               5                   10                  15

Gly Thr Met Leu Leu Gly Met Leu Met Ile Cys Ser Ala Ala Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Ile Gly Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Lys Asn Ala Thr Asn Thr Thr Ser Ser Ser Trp
        130                 135                 140

Gly Lys Met Glu Arg Gly Glu Ile Lys Asn Cys Ser Phe Asn Val Thr
145                 150                 155                 160

Thr Ser Ile Arg Asp Lys Met Lys Asn Glu Tyr Ala Leu Phe Tyr Lys
                165                 170                 175

Leu Asp Val Val Pro Ile Asp Asn Asp Asn Thr Ser Tyr Arg Leu Ile
                180                 185                 190

Ser Cys Asn Thr Ser Val Ile Thr Gln Ala Cys Pro Lys Val Ser Phe
            195                 200                 205

Glu Pro Ile Pro Ile His Tyr Cys Ala Pro Ala Gly Phe Ala Ile Leu
        210                 215                 220

Lys Cys Arg Asp Lys Lys Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Val Val Ile Arg Ser
                260                 265                 270

Ala Asn Phe Ser Asp Asn Ala Lys Thr Ile Ile Val Gln Leu Asn Glu
            275                 280                 285

Ser Val Glu Ile Asn Cys Thr Arg Pro Asn Asn Asn Thr Arg Arg Ser
        290                 295                 300

Ile His Ile Gly Pro Gly Arg Ala Phe Tyr Ala Thr Gly Glu Ile Ile
305                 310                 315                 320

Gly Asp Ile Arg Gln Ala His Cys Asn Leu Ser Ser Thr Lys Trp Asn
                325                 330                 335

Asn Thr Leu Lys Gln Ile Val Thr Lys Leu Arg Glu His Phe Asn Lys
                340                 345                 350

Thr Ile Val Phe Asn His Ser Ser Gly Gly Asp Pro Glu Ile Val Met
            355                 360                 365

His Ser Phe Asn Cys Gly Gly Glu Phe Phe Tyr Cys Asn Thr Thr Pro

-continued

```
            370                 375                 380
Leu Phe Asn Ser Thr Trp Asn Tyr Thr Tyr Thr Trp Asn Asn Thr Glu
385                 390                 395                 400

Gly Ser Asn Asp Thr Gly Arg Asn Ile Thr Leu Gln Cys Arg Ile Lys
                405                 410                 415

Gln Ile Ile Asn Met Trp Gln Glu Val Gly Lys Ala Met Tyr Ala Pro
                420                 425                 430

Pro Ile Arg Gly Gln Ile Arg Cys Ser Ser Asn Ile Thr Gly Leu Leu
                435                 440                 445

Leu Thr Arg Asp Gly Gly Asn Asn Ser Glu Thr Glu Ile Phe Arg Pro
450                 455                 460

Gly Gly Gly Asp Met Arg Asp Asn Trp Arg Ser Glu Leu Tyr Lys Tyr
465                 470                 475                 480

Lys Val Val Lys Ile Glu Pro Leu Gly Val Ala Pro Thr Lys Ala Lys
                485                 490                 495

Arg Arg Val Met Gln Arg Glu Lys Arg Ala Val Gly Ile Gly Ala Val
                500                 505                 510

Phe Leu Gly Phe Leu Gly Ala Ala Gly Ser Thr Met Gly Ala Ala Ser
                515                 520                 525

Val Thr Leu Thr Val Gln Ala Arg Leu Leu Leu Ser Gly Ile Val Gln
                530                 535                 540

Gln Gln Asn Asn Leu Leu Arg Ala Ile Glu Ala Glu Gln His Leu Leu
545                 550                 555                 560

Gln Leu Thr Val Trp Gly Ile Lys Gln Leu Gln Ala Arg Val Leu Ala
                565                 570                 575

Val Glu Arg Tyr Leu Lys Asp Gln Gln Leu Leu Gly Ile Trp Gly Cys
                580                 585                 590

Ser Gly Lys Leu Ile Cys Thr Thr Ala Val Pro Trp Asn Ala Ser Trp
                595                 600                 605

Ser Asn Lys Ser Leu Asp Lys Ile Trp Asp Asn Met Thr Trp Met Glu
                610                 615                 620

Trp Glu Arg Glu Ile Asp Asn Tyr Thr Ser Leu Ile Tyr Ser Leu Ile
625                 630                 635                 640

Glu Glu Ser Gln Asn Gln Gln Glu Lys Asn Glu Gln Glu Leu Leu Glu
                645                 650                 655

Leu Asp Lys Trp Ala Ser Leu Trp Asn Trp Phe Asp Ile Thr Lys Trp
                660                 665                 670

Leu Trp Tyr Ile Lys Ile Phe Ile Met Ile Val Gly Gly Leu Val Gly
                675                 680                 685

Leu Arg Ile Val Phe Thr Val Leu Ser Ile Val Asn Arg Val Arg Lys
                690                 695                 700

Gly Tyr Ser Pro Leu Ser Phe Gln Thr His Leu Pro Ala Pro Arg Gly
705                 710                 715                 720

Leu Asp Arg Pro Glu Gly Thr Glu Glu Gly Gly Glu Arg Asp Arg
                725                 730                 735

Asp Arg Ser Ser Arg Leu Val Asp Gly Phe Leu Ala Ile Val Trp Val
                740                 745                 750

Asp Leu Arg Ser Leu Cys Leu Phe Ser Tyr His Arg Leu Arg Asp Leu
                755                 760                 765

Leu Leu Ile Ala Ala Arg Ile Val Glu Leu Leu Gly Arg Arg Gly Trp
                770                 775                 780

Glu Ala Leu Lys Tyr Trp Trp Asn Leu Leu Gln Tyr Trp Ile Gln Glu
785                 790                 795                 800
```

```
Leu Lys Asn Ser Ala Val Ser Leu Leu Asn Ala Thr Ala Ile Ala Val
                805                 810                 815

Ala Glu Gly Thr Asp Arg Val Ile Glu Ile Val Gln Arg Ala Tyr Arg
            820                 825                 830

Ala Ile Leu His Ile Pro Thr Arg Ile Arg Gln Gly Leu Glu Arg Ala
        835                 840                 845

Leu Leu
    850

(2) INFORMATION FOR SEQ ID NO: 29:

(i) SEQUENCE CHARACTERISTICS:
        (A) LENGTH: 2573 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2573

(xi) SEQUENCE DESCRIPTION: SEQ ID NO: 29:

ATG AGA GTG AAG GGG ATC AGG AGG AAT TAT CAG CAC TTG TGG AGA TGG        48
Met Arg Val Lys Gly Ile Arg Arg Asn Tyr Gln His Leu Trp Arg Trp
 1               5                  10                  15

GGC ACC ATG CTC CTT GGG ATA TTG ATG ATC TGT AGT GCT GCA GGG AAA        96
Gly Thr Met Leu Leu Gly Ile Leu Met Ile Cys Ser Ala Ala Gly Lys
                20                  25                  30

TTG TGG GTC ACA GTC TAT TAT GGG GTA CCT GTG TGG AAA GAA ACA ACC       144
Leu Trp Val Thr Val Tyr Tyr Gly Val Pro Val Trp Lys Glu Thr Thr
            35                  40                  45

ACC ACT CTA TTT TGT GCA TCA GAT GCT AAA GCA TAT GAT ACA GAG ATA       192
Thr Thr Leu Phe Cys Ala Ser Asp Ala Lys Ala Tyr Asp Thr Glu Ile
        50                  55                  60

CAT AAT GTT TGG GCC ACA CAT GCC TGT GTA CCC ACA GAC CCC AAC CCA       240
His Asn Val Trp Ala Thr His Ala Cys Val Pro Thr Asp Pro Asn Pro
 65                 70                  75                  80

CAA GAA GTA GTA TTG GAA AAT GTG ACA GAA AAT TTT AAC ATG TGG AAA       288
Gln Glu Val Val Leu Glu Asn Val Thr Glu Asn Phe Asn Met Trp Lys
                85                  90                  95

AAT AAC ATG GTG GAA CAG ATG CAT GAG GAT ATA ATC AGT TTA TGG GAT       336
Asn Asn Met Val Glu Gln Met His Glu Asp Ile Ile Ser Leu Trp Asp
            100                 105                 110

CAA AGT TTA AAG CCA TGT GTA AAA TTA ACC CCA CTC TGT GTT ACT TTA       384
Gln Ser Leu Lys Pro Cys Val Lys Leu Thr Pro Leu Cys Val Thr Leu
        115                 120                 125

AAT TGC ACT GAT GCG GGG AAT ACT ACT AAT ACC AAT AGT AGT AGC AGG       432
Asn Cys Thr Asp Ala Gly Asn Thr Thr Asn Thr Asn Ser Ser Ser Arg
    130                 135                 140

GAA AAG CTG GAG AAA GGA GAA ATA AAA AAC TGC TCT TTC AAT ATC ACC       480
Glu Lys Leu Glu Lys Gly Glu Ile Lys Asn Cys Ser Phe Asn Ile Thr
145                 150                 155                 160

ACA AGC GTG AGA GAT AAG ATG CAG AAA GAA ACT GCA CTT TTT AAT AAA       528
Thr Ser Val Arg Asp Lys Met Gln Lys Glu Thr Ala Leu Phe Asn Lys
                165                 170                 175

CTT GAT ATA GTA CCA ATA GAT GAT GAT GAT AGG AAT AGT ACT AGG AAT       576
Leu Asp Ile Val Pro Ile Asp Asp Asp Asp Arg Asn Ser Thr Arg Asn
            180                 185                 190

AGT ACT AAC TAT AGG TTG ATA AGT TGT AAC ACC TCA GTC ATT ACA CAG       624
```

```
                                                           -continued

Ser Thr Asn Tyr Arg Leu Ile Ser Cys Asn Thr Ser Val Ile Thr Gln
        195                 200                 205

GCC TGT CCA AAG GTA TCA TTT GAG CCA ATT CCC ATA CAT TTC TGT ACC        672
Ala Cys Pro Lys Val Ser Phe Glu Pro Ile Pro Ile His Phe Cys Thr
210                 215                 220

CCG GCT GGT TTT GCG CTT CTA AAG TGT AAT AAT AAG ACG TTC AAT GGA        720
Pro Ala Gly Phe Ala Leu Leu Lys Cys Asn Asn Lys Thr Phe Asn Gly
225                 230                 235                 240

TCA GGA CCA TGC AAA AAT GTC AGC ACA GTA CAA TGT ACA CAT GGA ATT        768
Ser Gly Pro Cys Lys Asn Val Ser Thr Val Gln Cys Thr His Gly Ile
                245                 250                 255

AGG CCA GTA GTA TCA ACT CAA CTG CTG TTA AAT GGC AGT CTA GCA GAA        816
Arg Pro Val Val Ser Thr Gln Leu Leu Leu Asn Gly Ser Leu Ala Glu
                260                 265                 270

GGA GAG GTA GTA ATT AGA TCT GAA AAT TTC ACG AAC AAT GCT AAA ACC        864
Gly Glu Val Val Ile Arg Ser Glu Asn Phe Thr Asn Asn Ala Lys Thr
                275                 280                 285

ATA ATA GTA CAG CTG ACA GAA CCA GTA AAA ATT AAT TGT ACA AGA CCC        912
Ile Ile Val Gln Leu Thr Glu Pro Val Lys Ile Asn Cys Thr Arg Pro
290                 295                 300

AAC AAC AAT ACA AGA AAA AGT ATA CCT ATA GGA CCA GGG AGA GCA TTT        960
Asn Asn Asn Thr Arg Lys Ser Ile Pro Ile Gly Pro Gly Arg Ala Phe
305                 310                 315                 320

TAT GCA ACA GGA GAC ATA ATA GGA AAT ATA AGA CAA GCA CAT TGT AAC       1008
Tyr Ala Thr Gly Asp Ile Ile Gly Asn Ile Arg Gln Ala His Cys Asn
                325                 330                 335

CTT AGT AGA ACA GAC TGG AAT AAC ACT TTA GGA CAG ATA GTT GAA AAA       1056
Leu Ser Arg Thr Asp Trp Asn Asn Thr Leu Gly Gln Ile Val Glu Lys
                340                 345                 350

TTA AGA GAA CAA TTT GGG AAT AAA ACA ATA ATC TTT AAT CAC TCC TCA       1104
Leu Arg Glu Gln Phe Gly Asn Lys Thr Ile Ile Phe Asn His Ser Ser
                355                 360                 365

GGA GGG GAC CCA GAA ATT GTA ATG CAC AGT TTT AAT TGT AGA GGG GAA       1152
Gly Gly Asp Pro Glu Ile Val Met His Ser Phe Asn Cys Arg Gly Glu
370                 375                 380

TTT TTC TAC TGT AAT ACA ACA CAA TTG TTT GAC AGT ACT TGG GAT AAT       1200
Phe Phe Tyr Cys Asn Thr Thr Gln Leu Phe Asp Ser Thr Trp Asp Asn
385                 390                 395                 400

ACT AAA GTG TCA AAT GGC ACT AGC ACT GAA GAG AAT AGC ACA ATC ACA       1248
Thr Lys Val Ser Asn Gly Thr Ser Thr Glu Glu Asn Ser Thr Ile Thr
                405                 410                 415

CTC CCA TGC AGA ATA AAG CAA ATT GTA AAC ATG TGG CAG GAA GTA GGA       1296
Leu Pro Cys Arg Ile Lys Gln Ile Val Asn Met Trp Gln Glu Val Gly
                420                 425                 430

AAA GCA ATG TAT GCC CCT CCC ATC AGA GGA CAA ATT AGA TGT TCA TCA       1344
Lys Ala Met Tyr Ala Pro Pro Ile Arg Gly Gln Ile Arg Cys Ser Ser
                435                 440                 445

AAT ATT ACA GGG TTG CTA TTA ACA AGA GAT GGA GGT AGT AAC AAC AGC       1392
Asn Ile Thr Gly Leu Leu Leu Thr Arg Asp Gly Gly Ser Asn Asn Ser
450                 455                 460

ATG AAT GAG ACC TTC AGA CCT GGA GGA GGA GAT ATG AGG GAC AAT TGG       1440
Met Asn Glu Thr Phe Arg Pro Gly Gly Gly Asp Met Arg Asp Asn Trp
465                 470                 475                 480

AGA AGT GAA TTA TAC AAA TAT AAA GTA GTA AAA ATT GAA CCA TTA GGA       1488
Arg Ser Glu Leu Tyr Lys Tyr Lys Val Val Lys Ile Glu Pro Leu Gly
                485                 490                 495

GTA GCA CCC ACC AAG GCA AAG AGA AGA GTG GTG CAG AGA GAA AAA AGA       1536
Val Ala Pro Thr Lys Ala Lys Arg Arg Val Val Gln Arg Glu Lys Arg
                500                 505                 510
```

```
GCA GTG GGA ATA GGA GCT GTG TTC CTT GGG TTC TTA GGA GCA GCA GGA       1584
Ala Val Gly Ile Gly Ala Val Phe Leu Gly Phe Leu Gly Ala Ala Gly
        515                 520                 525

AGC ACT ATG GGC GCA GCG TCA ATA ACG CTG ACG GTA CAG GCC AGA CTA       1632
Ser Thr Met Gly Ala Ala Ser Ile Thr Leu Thr Val Gln Ala Arg Leu
        530                 535                 540

TTA TTG TCT GGT ATA GTG CAA CAG CAG AAC AAT TTG CTG AGG GCT ATT       1680
Leu Leu Ser Gly Ile Val Gln Gln Gln Asn Asn Leu Leu Arg Ala Ile
545                 550                 555                 560

GAG GCG CAA CAG CAT CTG TTG CAA CTC ATA GTC TGG GGC ATC AAG CAG       1728
Glu Ala Gln Gln His Leu Leu Gln Leu Ile Val Trp Gly Ile Lys Gln
                565                 570                 575

CTC CAG GCA AGA GTC CTG GCT GTG GAA AGA TAC CTA AGG GAT CAA CAG       1776
Leu Gln Ala Arg Val Leu Ala Val Glu Arg Tyr Leu Arg Asp Gln Gln
        580                 585                 590

CTC CTG GGG ATT TGG GGT TGC TCT GGA AAA CTC ATT TGC ACC ACC TCA       1824
Leu Leu Gly Ile Trp Gly Cys Ser Gly Lys Leu Ile Cys Thr Thr Ser
        595                 600                 605

GTG CCT TGG AAT GCT AGT TGG AGT AAT AAA TCT CTA GAT AAG ATT TGG       1872
Val Pro Trp Asn Ala Ser Trp Ser Asn Lys Ser Leu Asp Lys Ile Trp
        610                 615                 620

GAT AAC ATG ACC TGG ATG GAG TGG GAA AGA GAA ATT GAG AAT TAC ACA       1920
Asp Asn Met Thr Trp Met Glu Trp Glu Arg Glu Ile Glu Asn Tyr Thr
625                 630                 635                 640

AGC TTA ATA TAC ACC TTA ATT GAA GAA TCG CAG AAC CAA CAA GAA AAG       1968
Ser Leu Ile Tyr Thr Leu Ile Glu Glu Ser Gln Asn Gln Gln Glu Lys
                645                 650                 655

AAT GAA CAA GAC TTA TTG GAA TTG GAT CAA TGG GCA AGT CTG TGG AAT       2016
Asn Glu Gln Asp Leu Leu Glu Leu Asp Gln Trp Ala Ser Leu Trp Asn
                660                 665                 670

TGG TTT AGC ATA ACA AAA TGG CTG TGG TAT ATA AAA ATA TTC ATA ATG       2064
Trp Phe Ser Ile Thr Lys Trp Leu Trp Tyr Ile Lys Ile Phe Ile Met
        675                 680                 685

ATA GTT GGA GGC TTG GTA GGT TTA AGA ATA GTT TTT GCT GTA CTT TCT       2112
Ile Val Gly Gly Leu Val Gly Leu Arg Ile Val Phe Ala Val Leu Ser
        690                 695                 700

ATA GTG AAT AGA GTT AGG CAG GGA TAC TCA CCA TTA TCG TTT CAG ACC       2160
Ile Val Asn Arg Val Arg Gln Gly Tyr Ser Pro Leu Ser Phe Gln Thr
705                 710                 715                 720

CGC CTC CCA GCC CCG AGG AGA CCC GAC AGG CCC GAA GGA ATC GAA GAA       2208
Arg Leu Pro Ala Pro Arg Arg Pro Asp Arg Pro Glu Gly Ile Glu Glu
                725                 730                 735

GAA GGT GGA GAG CAA GGC AGA GAC AGA TCC ATT CGC TTA GTG GAT GGA       2256
Glu Gly Gly Glu Gln Gly Arg Asp Arg Ser Ile Arg Leu Val Asp Gly
                740                 745                 750

TTC TTA GCA CTT ATC TGG GAC GAC CTA CGG AGC CTG TGC CTC TTC AGC       2304
Phe Leu Ala Leu Ile Trp Asp Asp Leu Arg Ser Leu Cys Leu Phe Ser
        755                 760                 765

TAC CAC CGC TTG AGA GAC TTA CTC TTG ATT GCA ACG AGG ATT GTG GAA       2352
Tyr His Arg Leu Arg Asp Leu Leu Leu Ile Ala Thr Arg Ile Val Glu
770                 775                 780

CTT CTG GGA CGC AGG GGG TGG GAA GCC CTC AAA TAT TGG TGG AAT CTC       2400
Leu Leu Gly Arg Arg Gly Trp Glu Ala Leu Lys Tyr Trp Trp Asn Leu
785                 790                 795                 800

CTA CAG TAT TGG ATT CAG GAA CTA AAG AAT AGT GCT GTT AGC TTG CTT       2448
Leu Gln Tyr Trp Ile Gln Glu Leu Lys Asn Ser Ala Val Ser Leu Leu
                805                 810                 815

AAT GTC ACA GCC ATA GCA GTA GCT GAG GGG ACA GAT AGG GTT TTA GAA       2496
Asn Val Thr Ala Ile Ala Val Ala Glu Gly Thr Asp Arg Val Leu Glu
        820                 825                 830
```

```
GTA TTA CAA AGA GCT TAT AGA GCT ATT CTC CAC ATA CCT ACA AGA ATA          2544
Val Leu Gln Arg Ala Tyr Arg Ala Ile Leu His Ile Pro Thr Arg Ile
    835                 840                 845

AGA CAG GGC TTG GAA AGG GCT TTG CTA TA                                   2573
Arg Gln Gly Leu Glu Arg Ala Leu Leu
    850                 855
```

(2) INFORMATION FOR SEQ ID NO: 30:

(i) SEQUENCE CHARACTERISTICS:
        (A) LENGTH: 857 amino acids
        (B) TYPE: amino acid
        (C) STRANDEDNESS: single
        (D) TOPOLOGY: linear (xi) SEQUENCE DESCRIPTION: SEQ ID NO: 30:

```
Met Arg Val Lys Gly Ile Arg Arg Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Thr Thr
        35                  40                  45

Thr Thr Leu Phe Cys Ala Ser Asp Ala Lys Ala Tyr Asp Thr Glu Ile
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Ala Gly Asn Thr Thr Asn Thr Asn Ser Ser Ser Arg
    130                 135                 140

Glu Lys Leu Glu Lys Gly Glu Ile Lys Asn Cys Ser Phe Asn Ile Thr
145                 150                 155                 160

Thr Ser Val Arg Asp Lys Met Gln Lys Glu Thr Ala Leu Phe Asn Lys
                165                 170                 175

Leu Asp Ile Val Pro Ile Asp Asp Asp Arg Asn Ser Thr Arg Asn
            180                 185                 190

Ser Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Phe Cys Thr
    210                 215                 220

Pro Ala Gly Phe Ala Leu Leu Lys Cys Asn Asn Lys Thr Phe Asn Gly
225                 230                 235                 240

Ser Gly Pro Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Gly Glu Val Val Ile Arg Ser Glu Asn Phe Thr Asn Asn Ala Lys Thr
        275                 280                 285

Ile Ile Val Gln Leu Thr Glu Pro Val Lys Ile Asn Cys Thr Arg Pro
    290                 295                 300

Asn Asn Asn Thr Arg Lys Ser Ile Pro Ile Gly Pro Gly Arg Ala Phe
305                 310                 315                 320
```

-continued

```
Tyr Ala Thr Gly Asp Ile Ile Gly Asn Ile Arg Gln Ala His Cys Asn
                325                 330                 335

Leu Ser Arg Thr Asp Trp Asn Asn Thr Leu Gly Gln Ile Val Glu Lys
            340                 345                 350

Leu Arg Glu Gln Phe Gly Asn Lys Thr Ile Ile Phe Asn His Ser Ser
        355                 360                 365

Gly Gly Asp Pro Glu Ile Val Met His Ser Phe Asn Cys Arg Gly Glu
    370                 375                 380

Phe Phe Tyr Cys Asn Thr Thr Gln Leu Phe Asp Ser Thr Trp Asp Asn
385                 390                 395                 400

Thr Lys Val Ser Asn Gly Thr Ser Thr Glu Glu Asn Ser Thr Ile Thr
                405                 410                 415

Leu Pro Cys Arg Ile Lys Gln Ile Val Asn Met Trp Gln Glu Val Gly
            420                 425                 430

Lys Ala Met Tyr Ala Pro Pro Ile Arg Gly Gln Ile Arg Cys Ser Ser
        435                 440                 445

Asn Ile Thr Gly Leu Leu Leu Thr Arg Asp Gly Gly Ser Asn Asn Ser
    450                 455                 460

Met Asn Glu Thr Phe Arg Pro Gly Gly Gly Asp Met Arg Asp Asn Trp
465                 470                 475                 480

Arg Ser Glu Leu Tyr Lys Tyr Lys Val Val Lys Ile Glu Pro Leu Gly
                485                 490                 495

Val Ala Pro Thr Lys Ala Lys Arg Arg Val Val Gln Arg Glu Lys Arg
            500                 505                 510

Ala Val Gly Ile Gly Ala Val Phe Leu Gly Phe Leu Gly Ala Ala Gly
        515                 520                 525

Ser Thr Met Gly Ala Ala Ser Ile Thr Leu Thr Val Gln Ala Arg Leu
    530                 535                 540

Leu Leu Ser Gly Ile Val Gln Gln Gln Asn Asn Leu Leu Arg Ala Ile
545                 550                 555                 560

Glu Ala Gln Gln His Leu Leu Gln Leu Ile Val Trp Gly Ile Lys Gln
                565                 570                 575

Leu Gln Ala Arg Val Leu Ala Val Glu Arg Tyr Leu Arg Asp Gln Gln
            580                 585                 590

Leu Leu Gly Ile Trp Gly Cys Ser Gly Lys Leu Ile Cys Thr Thr Ser
        595                 600                 605

Val Pro Trp Asn Ala Ser Trp Ser Asn Lys Ser Leu Asp Lys Ile Trp
    610                 615                 620

Asp Asn Met Thr Trp Met Glu Trp Glu Arg Glu Ile Glu Asn Tyr Thr
625                 630                 635                 640

Ser Leu Ile Tyr Thr Leu Ile Glu Glu Ser Gln Asn Gln Gln Glu Lys
                645                 650                 655

Asn Glu Gln Asp Leu Leu Glu Leu Asp Gln Trp Ala Ser Leu Trp Asn
            660                 665                 670

Trp Phe Ser Ile Thr Lys Trp Leu Trp Tyr Ile Lys Ile Phe Ile Met
        675                 680                 685

Ile Val Gly Gly Leu Val Gly Leu Arg Ile Val Phe Ala Val Leu Ser
    690                 695                 700

Ile Val Asn Arg Val Arg Gln Gly Tyr Ser Pro Leu Ser Phe Gln Thr
705                 710                 715                 720

Arg Leu Pro Ala Pro Arg Arg Pro Asp Arg Pro Glu Gly Ile Glu Glu
                725                 730                 735
```

-continued

```
Glu Gly Gly Glu Gln Gly Arg Asp Arg Ser Ile Arg Leu Val Asp Gly
            740                 745                 750

Phe Leu Ala Leu Ile Trp Asp Asp Leu Arg Ser Leu Cys Leu Phe Ser
            755                 760                 765

Tyr His Arg Leu Arg Asp Leu Leu Ile Ala Thr Arg Ile Val Glu
770                 775                 780

Leu Leu Gly Arg Arg Gly Trp Glu Ala Leu Lys Tyr Trp Asn Leu
785                 790                 795                 800

Leu Gln Tyr Trp Ile Gln Glu Leu Lys Asn Ser Ala Val Ser Leu Leu
            805                 810                 815

Asn Val Thr Ala Ile Ala Val Ala Glu Gly Thr Asp Arg Val Leu Glu
            820                 825                 830

Val Leu Gln Arg Ala Tyr Arg Ala Ile Leu His Ile Pro Thr Arg Ile
            835                 840                 845

Arg Gln Gly Leu Glu Arg Ala Leu Leu
    850                 855
```

(2) INFORMATION FOR SEQ ID NO: 31:

(i) SEQUENCE CHARACTERISTICS:
        (A) LENGTH: 2570 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2570

(xi) SEQUENCE DESCRIPTION: SEQ ID NO: 31:

```
ATG AGA GTG AAG AGG ATC AGG AGG AAT TAT CAG CAC TTG TGG AAA TGG        48
Met Arg Val Lys Arg Ile Arg Arg Asn Tyr Gln His Leu Trp Lys Trp
1               5                   10                  15

GGC ACC ATG CTC CTT GGG ATG TTG ATG ATC TGT AGT GCT GCA GGA AAA        96
Gly Thr Met Leu Leu Gly Met Leu Met Ile Cys Ser Ala Ala Gly Lys
                20                  25                  30

TTG TGG GTC ACA GTC TAT TAT GGG GTA CCT GTG TGG AAA GAA ACA ACC       144
Leu Trp Val Thr Val Tyr Tyr Gly Val Pro Val Trp Lys Glu Thr Thr
            35                  40                  45

ACC ACT CTA TTT TGT GCA TCA GAT GCT AAA GCA TAT GAT ACA GAG ATA       192
Thr Thr Leu Phe Cys Ala Ser Asp Ala Lys Ala Tyr Asp Thr Glu Ile
        50                  55                  60

CAT AAT GTT TGG GCC ACA CAT GCC TGT GTA CCC ACA GAC CCC AAC CCA       240
His Asn Val Trp Ala Thr His Ala Cys Val Pro Thr Asp Pro Asn Pro
65                  70                  75                  80

CAA GAA GTA GTA TTG GAA AAT GTG ACA GAA AAT TTT AAC ATG TGG AAA       288
Gln Glu Val Val Leu Glu Asn Val Thr Glu Asn Phe Asn Met Trp Lys
                85                  90                  95

AAT AAC ATG GTG GAA CAG ATG CAT GAG GAT ATA ATC AGT TTA TGG GAT       336
Asn Asn Met Val Glu Gln Met His Glu Asp Ile Ile Ser Leu Trp Asp
            100                 105                 110

CAA AGT CTA AAG CCA TGT GTA AAA TTA ACC CCA CTC TGT GTT ACT TTA       384
Gln Ser Leu Lys Pro Cys Val Lys Leu Thr Pro Leu Cys Val Thr Leu
        115                 120                 125

AAT TGC ACT GAT GCG GGG AAT ACT ACT AAT ACC AAT AGT AGT AGC GGG       432
Asn Cys Thr Asp Ala Gly Asn Thr Thr Asn Thr Asn Ser Ser Ser Gly
    130                 135                 140

GAA AAG CTG GAG AAA GGA GAA ATA AAA AAC TGC TCT TTC AAT ATC ACC       480
Glu Lys Leu Glu Lys Gly Glu Ile Lys Asn Cys Ser Phe Asn Ile Thr
```

```
                    145                 150                 155                 160
ACA AGC ATG AGA GAT AAG ATG CAG AGA GAA ACT GCA CTT TTT AAT AAA         528
Thr Ser Met Arg Asp Lys Met Gln Arg Glu Thr Ala Leu Phe Asn Lys
                    165                 170                 175

CTT GAT ATA GTA CCA ATA GAT GAT GAT AGG AAT AGT ACT AGG AAT             576
Leu Asp Ile Val Pro Ile Asp Asp Asp Arg Asn Ser Thr Arg Asn
                180                 185                 190

AGT ACT AAC TAT AGG TTG ATA AGT TGT AAC ACC TCA GTC ATT ACA CAG         624
Ser Thr Asn Tyr Arg Leu Ile Ser Cys Asn Thr Ser Val Ile Thr Gln
                    195                 200                 205

GCC TGT CCA AAG GTA TCA TTT GAG CCA ATT CCC ATA CAT TTC TGT ACC         672
Ala Cys Pro Lys Val Ser Phe Glu Pro Ile Pro Ile His Phe Cys Thr
        210                 215                 220

CCG GCT GGT TTT GCG CTT CTA AAG TGT AAT AAT GAG ACG TTC AAT GGA         720
Pro Ala Gly Phe Ala Leu Leu Lys Cys Asn Asn Glu Thr Phe Asn Gly
225                 230                 235                 240

TCA GGA CCA TGC AAA AAT GTC AGC ACA GTA CTA TGT ACA CAT GGA ATT         768
Ser Gly Pro Cys Lys Asn Val Ser Thr Val Leu Cys Thr His Gly Ile
                245                 250                 255

AGG CCA GTA GTA TCA ACT CAA CTG CTG TTA AAT GGC AGT CTA GCA GGA         816
Arg Pro Val Val Ser Thr Gln Leu Leu Leu Asn Gly Ser Leu Ala Gly
                260                 265                 270

GAA GAG GTA GTA ATT AGA TCT GAA AAT TTC ACG AAC AAT GCT AAA ACC         864
Glu Glu Val Val Ile Arg Ser Glu Asn Phe Thr Asn Asn Ala Lys Thr
                    275                 280                 285

ATA ATA GTA CAG CTC AAA GAA CCA GTA AAA ATT AAT TGT ACA AGA CCC         912
Ile Ile Val Gln Leu Lys Glu Pro Val Lys Ile Asn Cys Thr Arg Pro
        290                 295                 300

AAC AAC AAT ACA AGA AAA AGT ATA CCT ATA GGA CCA GGG AGA GCA TTT         960
Asn Asn Asn Thr Arg Lys Ser Ile Pro Ile Gly Pro Gly Arg Ala Phe
305                 310                 315                 320

TAT GCA ACA GGC GAC ATA ATA GGA AAT ATA AGA CAA GCA CAT TGT AAC        1008
Tyr Ala Thr Gly Asp Ile Ile Gly Asn Ile Arg Gln Ala His Cys Asn
                325                 330                 335

CTT AGT AGA ACA GAC TGG AAT AAC ACT TTA AGA CAG ATA GCT GAA AAA        1056
Leu Ser Arg Thr Asp Trp Asn Asn Thr Leu Arg Gln Ile Ala Glu Lys
                340                 345                 350

TTA AGA AAA CAA TTT GGG AAT AAA ACA ATA ATC TTT AAT CAC TCC TCA        1104
Leu Arg Lys Gln Phe Gly Asn Lys Thr Ile Ile Phe Asn His Ser Ser
        355                 360                 365

GGA GGG GAC CCA GAA ATT GTA ATG CAC AGT TTT AAT TGT AGA GGG GAA        1152
Gly Gly Asp Pro Glu Ile Val Met His Ser Phe Asn Cys Arg Gly Glu
370                 375                 380

TTT TTC TAC TGT GAT ACA ACA CAA TTG TTT AAC AGT ACT TGG AAT GCA        1200
Phe Phe Tyr Cys Asp Thr Thr Gln Leu Phe Asn Ser Thr Trp Asn Ala
385                 390                 395                 400

AAT AAC ACT GAA AGG AAT AGC ACT AAA GAG AAT AGC ACA ATC ACA CTC        1248
Asn Asn Thr Glu Arg Asn Ser Thr Lys Glu Asn Ser Thr Ile Thr Leu
                405                 410                 415

CCA TGC AGA ATA AAA CAA ATT GTA AAC ATG TGG CAG GAA GTA GGA AAA        1296
Pro Cys Arg Ile Lys Gln Ile Val Asn Met Trp Gln Glu Val Gly Lys
                420                 425                 430

GCA ATG TAT GCC CCT CCC ATC AGA GGA CAA ATT AGA TGT TCA TCA AAT        1344
Ala Met Tyr Ala Pro Pro Ile Arg Gly Gln Ile Arg Cys Ser Ser Asn
                435                 440                 445

ATT ACA GGG TTG CTA TTA ACA AGA GAT GGA GGT AGT AGC AAC AGC ATG        1392
Ile Thr Gly Leu Leu Leu Thr Arg Asp Gly Gly Ser Ser Asn Ser Met
        450                 455                 460

AAT GAG ACC TTC AGA CCT GGA GGA GGA GAT ATG AGG GAC AAT TGG AGA        1440
```

```
                Asn Glu Thr Phe Arg Pro Gly Gly Gly Asp Met Arg Asp Asn Trp Arg
                465                 470                 475                 480

AGT GAA TTA TAC AAA TAT AAA GTA GTA AAA ATT GAA CCA TTA GGA GTA                  1488
Ser Glu Leu Tyr Lys Tyr Lys Val Val Lys Ile Glu Pro Leu Gly Val
                    485                 490                 495

GCA CCC ACC AAG GCA ATG AGA AGA GTG GTG CAG AGA GAA AAA AGA GCA                  1536
Ala Pro Thr Lys Ala Met Arg Arg Val Val Gln Arg Glu Lys Arg Ala
                500                 505                 510

GTG GGA ATA GGA GCT GTG TTC CTT GGG TTC TTA GGA GCA GCA GGA AGC                  1584
Val Gly Ile Gly Ala Val Phe Leu Gly Phe Leu Gly Ala Ala Gly Ser
            515                 520                 525

ACT ATG GGC GCA GCG TCA ATA ACG CTG ACG GTA CAG GCC AGA CTA TTA                  1632
Thr Met Gly Ala Ala Ser Ile Thr Leu Thr Val Gln Ala Arg Leu Leu
        530                 535                 540

TTG TCT GGT ATA GTG CAA CAG CAG AAC AAT TTG CTG AGG GCT ATT GAG                  1680
Leu Ser Gly Ile Val Gln Gln Gln Asn Asn Leu Leu Arg Ala Ile Glu
545                 550                 555                 560

GCG CAA CAG CAT CTG TTG CAA CTC ACA GTC TGG GGC ATC AAG CAG CTC                  1728
Ala Gln Gln His Leu Leu Gln Leu Thr Val Trp Gly Ile Lys Gln Leu
                565                 570                 575

CAG GCA AGA GTC CTG GCT GTG GAA AGA TAC CTA AGG GAT CAA CAG CTC                  1776
Gln Ala Arg Val Leu Ala Val Glu Arg Tyr Leu Arg Asp Gln Gln Leu
                580                 585                 590

CTG GGG ATT TGG GGT TGC TCT GGA AAA CTC ATT TGC ACC ACC TCT GTG                  1824
Leu Gly Ile Trp Gly Cys Ser Gly Lys Leu Ile Cys Thr Thr Ser Val
            595                 600                 605

CCT TGG AAT GCT AGT TGG AGT AAT AAA TCT CTA GAT AAG ATT TGG GAT                  1872
Pro Trp Asn Ala Ser Trp Ser Asn Lys Ser Leu Asp Lys Ile Trp Asp
        610                 615                 620

AAC ATG ACC TGG ATG GAG TGG GAA AGA GAA ATT GAG AAT TAC ACA AGC                  1920
Asn Met Thr Trp Met Glu Trp Glu Arg Glu Ile Glu Asn Tyr Thr Ser
625                 630                 635                 640

TTA ATA TAC ACC TTA ATT GAA GAA TCG CAG AAC CAA CAA GAA AAG AAT                  1968
Leu Ile Tyr Thr Leu Ile Glu Glu Ser Gln Asn Gln Gln Glu Lys Asn
                645                 650                 655

AAA CAA GAC TTA TTG GAA TTG GAT CAA TAG GCA AGT TTG TGG AAT TGG                  2016
Lys Gln Asp Leu Leu Glu Leu Asp Gln  *  Ala Ser Leu Trp Asn Trp
                660                 665                 670

TTT AGC ATA ACA AAA TGG CTG TGG TAT ATA AAA ATA TTC ATA ATG ATA                  2064
Phe Ser Ile Thr Lys Trp Leu Trp Tyr Ile Lys Ile Phe Ile Met Ile
            675                 680                 685

GTT GGA GGC TTG GTA GGT TTA AGA ATA GTT TTT GCT GTA CTT TCT ATA                  2112
Val Gly Gly Leu Val Gly Leu Arg Ile Val Phe Ala Val Leu Ser Ile
        690                 695                 700

GTG AAT AGA GTT AGG CAG GGG TAC TCA CCA TTA TCA TTT CAG ACC CGC                  2160
Val Asn Arg Val Arg Gln Gly Tyr Ser Pro Leu Ser Phe Gln Thr Arg
705                 710                 715                 720

CTC CCA GCC CCG AGG GGA CCC GAC AGG CCC AAA GGA ATC GAA GAA GAA                  2208
Leu Pro Ala Pro Arg Gly Pro Asp Arg Pro Lys Gly Ile Glu Glu Glu
                725                 730                 735

GGT GGA GAG CAA GAC AGG GAC AGA TCC ATT CGC TTA GTG GAT GGA TTC                  2256
Gly Gly Glu Gln Asp Arg Asp Arg Ser Ile Arg Leu Val Asp Gly Phe
                740                 745                 750

TTA GCA CTT ATC TGG GAC GAT CTA CGG AGC CTG TGC CTC TTC AGC TAC                  2304
Leu Ala Leu Ile Trp Asp Asp Leu Arg Ser Leu Cys Leu Phe Ser Tyr
            755                 760                 765

CAC CGC TTG AGA GAC TTA CTC TTG ATT GCA ACG AGG ATT GTG GAA CTT                  2352
His Arg Leu Arg Asp Leu Leu Leu Ile Ala Thr Arg Ile Val Glu Leu
        770                 775                 780
```

-continued

```
CTG GGA CGC AGG GGG TGG GAA GCC CTC AAA TAT TGG TGG AAT CTC CTA      2400
Leu Gly Arg Arg Gly Trp Glu Ala Leu Lys Tyr Trp Trp Asn Leu Leu
785                 790                 795                 800

CAG TAT TGG ATT CAG GAA CTA AAG AAT AGT GCT GTT AGC TTG CTT AAT      2448
Gln Tyr Trp Ile Gln Glu Leu Lys Asn Ser Ala Val Ser Leu Leu Asn
                805                 810                 815

GTC ACA GCC ATA GCA GTA GCT GAG GGG ACA GAT AGG GTT CTA GAA GCA      2496
Val Thr Ala Ile Ala Val Ala Glu Gly Thr Asp Arg Val Leu Glu Ala
            820                 825                 830

TTG CAA AGA GCT TAT AGA GCT ATT CTC CAC ATA CCT ACA AGA ATA AGA      2544
Leu Gln Arg Ala Tyr Arg Ala Ile Leu His Ile Pro Thr Arg Ile Arg
        835                 840                 845

CAA GGC TTG GAA AGG GCT TTG CTA TA                                   2570
Gln Gly Leu Glu Arg Ala Leu Leu
    850                 855
```

(2) INFORMATION FOR SEQ ID NO: 32:

(i) SEQUENCE CHARACTERISTICS:
        (A) LENGTH: 665 amino acids
        (B) TYPE: amino acid
        (C) STRANDEDNESS: single
        (D) TOPOLOGY: linear (xi) SEQUENCE DESCRIPTION: SEQ ID NO: 32:

```
Met Arg Val Lys Arg Ile Arg Arg Asn Tyr Gln His Leu Trp Lys Trp
1               5                   10                  15

Gly Thr Met Leu Leu Gly Met Leu Met Ile Cys Ser Ala Ala Gly Lys
            20                  25                  30

Leu Trp Val Thr Val Tyr Tyr Gly Val Pro Val Trp Lys Glu Thr Thr
        35                  40                  45

Thr Thr Leu Phe Cys Ala Ser Asp Ala Lys Ala Tyr Asp Thr Glu Ile
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Ala Gly Asn Thr Thr Asn Thr Asn Ser Ser Ser Gly
    130                 135                 140

Glu Lys Leu Glu Lys Gly Glu Ile Lys Asn Cys Ser Phe Asn Ile Thr
145                 150                 155                 160

Thr Ser Met Arg Asp Lys Met Gln Arg Glu Thr Ala Leu Phe Asn Lys
                165                 170                 175

Leu Asp Ile Val Pro Ile Asp Asp Asp Arg Asn Ser Thr Arg Asn
            180                 185                 190

Ser Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Phe Cys Thr
    210                 215                 220

Pro Ala Gly Phe Ala Leu Leu Lys Cys Asn Asn Glu Thr Phe Asn Gly
225                 230                 235                 240

Ser Gly Pro Cys Lys Asn Val Ser Thr Val Leu Cys Thr His Gly Ile
                245                 250                 255
```

```
Arg Pro Val Val Ser Thr Gln Leu Leu Leu Asn Gly Ser Leu Ala Gly
            260                 265                 270

Glu Glu Val Val Ile Arg Ser Glu Asn Phe Thr Asn Ala Lys Thr
            275                 280                 285

Ile Ile Val Gln Leu Lys Glu Pro Val Lys Ile Asn Cys Thr Arg Pro
            290                 295                 300

Asn Asn Asn Thr Arg Lys Ser Ile Pro Ile Gly Pro Gly Arg Ala Phe
305                 310                 315                 320

Tyr Ala Thr Gly Asp Ile Ile Gly Asn Ile Arg Gln Ala His Cys Asn
                    325                 330                 335

Leu Ser Arg Thr Asp Trp Asn Asn Thr Leu Arg Gln Ile Ala Glu Lys
                340                 345                 350

Leu Arg Lys Gln Phe Gly Asn Lys Thr Ile Ile Phe Asn His Ser Ser
            355                 360                 365

Gly Gly Asp Pro Glu Ile Val Met His Ser Phe Asn Cys Arg Gly Glu
    370                 375                 380

Phe Phe Tyr Cys Asp Thr Thr Gln Leu Phe Asn Ser Thr Trp Asn Ala
385                 390                 395                 400

Asn Asn Thr Glu Arg Asn Ser Thr Lys Glu Asn Ser Thr Ile Thr Leu
            405                 410                 415

Pro Cys Arg Ile Lys Gln Ile Val Asn Met Trp Gln Glu Val Gly Lys
            420                 425                 430

Ala Met Tyr Ala Pro Pro Ile Arg Gly Gln Ile Arg Cys Ser Ser Asn
            435                 440                 445

Ile Thr Gly Leu Leu Leu Thr Arg Asp Gly Gly Ser Ser Asn Ser Met
    450                 455                 460

Asn Glu Thr Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Met Arg Arg Val Val Gln Arg Glu Lys Arg Ala
            500                 505                 510

Val Gly Ile Gly Ala Val Phe Leu Gly Phe Leu Gly Ala Ala Gly Ser
    515                 520                 525

Thr Met Gly Ala Ala Ser Ile Thr Leu Thr Val Gln Ala Arg Leu Leu
    530                 535                 540

Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Ser Val
            595                 600                 605

Pro Trp Asn Ala Ser Trp Ser Asn Lys Ser Leu Asp Lys Ile Trp Asp
    610                 615                 620

Asn Met Thr Trp Met Glu Trp Glu Arg Glu Ile Glu Asn Tyr Thr Ser
625                 630                 635                 640

Leu Ile Tyr Thr Leu Ile Glu Glu Ser Gln Asn Gln Gln Glu Lys Asn
                645                 650                 655

Lys Gln Asp Leu Leu Glu Leu Asp Gln
            660                 665
```

-continued (2) INFORMATION FOR SEQ ID NO: 33:

(i) SEQUENCE CHARACTERISTICS:
(A) LENGTH: 190 amino acids
(B) TYPE: amino acid
(C) STRANDEDNESS: single
(D) TOPOLOGY: linear (xi) SEQUENCE DESCRIPTION: SEQ ID NO: 33:

```
Ala Ser Leu Trp Asn Trp Phe Ser Ile Thr Lys Trp Leu Trp Tyr Ile
 1           5                  10                  15

Lys Ile Phe Ile Met Ile Val Gly Gly Leu Val Gly Leu Arg Ile Val
            20                  25                  30

Phe Ala Val Leu Ser Ile Val Asn Arg Val Arg Gln Gly Tyr Ser Pro
             35                  40                  45

Leu Ser Phe Gln Thr Arg Leu Pro Ala Pro Arg Gly Pro Asp Arg Pro
 50                  55                  60

Lys Gly Ile Glu Glu Glu Gly Gly Glu Gln Asp Arg Asp Arg Ser Ile
 65                  70                  75                  80

Arg Leu Val Asp Gly Phe Leu Ala Leu Ile Trp Asp Asp Leu Arg Ser
                 85                  90                  95

Leu Cys Leu Phe Ser Tyr His Arg Leu Arg Asp Leu Leu Leu Ile Ala
                100                 105                 110

Thr Arg Ile Val Glu Leu Leu Gly Arg Arg Gly Trp Glu Ala Leu Lys
            115                 120                 125

Tyr Trp Trp Asn Leu Leu Gln Tyr Trp Ile Gln Glu Leu Lys Asn Ser
    130                 135                 140

Ala Val Ser Leu Leu Asn Val Thr Ala Ile Ala Val Ala Glu Gly Thr
145                 150                 155                 160

Asp Arg Val Leu Glu Ala Leu Gln Arg Ala Tyr Arg Ala Ile Leu His
                165                 170                 175

Ile Pro Thr Arg Ile Arg Gln Gly Leu Glu Arg Ala Leu Leu
            180                 185                 190
```